United States Patent [19]

Bridges et al.

[11] Patent Number: 5,679,683
[45] Date of Patent: Oct. 21, 1997

[54] TRICYCLIC COMPOUNDS CAPABLE OF INHIBITING TYROSINE KINASES OF THE EPIDERMAL GROWTH FACTOR RECEPTOR FAMILY

[75] Inventors: Alexander James Bridges, Saline, Mich.; William Alexander Denny, Pakuranga, New Zealand; David Fry, Ypsilanti, Mich.; Alan Kraker; Robert Frederick Meyer, both of Ann Arbor, Mich.; Gordon William Rewcastle, Manurewa; Andrew Mark Thompson, Mount Eden, both of New Zealand; Howard Daniel Hollis Showalter, Ann Arbor, Mich.

[73] Assignee: Warner-Lambert Company, Morris Plains, N.J.

[21] Appl. No.: 358,352

[22] Filed: Dec. 23, 1994

Related U.S. Application Data

[63] Continuation-in-part of Ser. No. 186,735, Jan. 25, 1994, abandoned, and Ser. No. 186,745, Jan. 25, 1994, abandoned.

[51] Int. Cl.$^6$ .................... A61K 31/505; C07D 487/00
[52] U.S. Cl. ................................. 514/267; 544/250
[58] Field of Search .......................... 544/234, 250; 514/267

[56] References Cited

U.S. PATENT DOCUMENTS

| | | | |
|---|---|---|---|
| 3,634,427 | 1/1972 | Schweizer et al. | 260/256.5 |
| 3,749,355 | 7/1973 | Bourgau et al. | 260/534 |
| 3,755,583 | 8/1973 | De Angelis et al. | 424/251 |
| 5,141,941 | 8/1992 | Fujii et al. | 514/256 |

FOREIGN PATENT DOCUMENTS

| | | |
|---|---|---|
| 0404355 | 12/1990 | European Pat. Off. . |
| 0414386 | 2/1991 | European Pat. Off. . |
| 0537463 | 4/1993 | European Pat. Off. . |
| 0602851 | 6/1994 | European Pat. Off. . |
| 1934172 | 1/1970 | Germany . |
| 2725019 | 12/1977 | Germany . |
| 157280 | 5/1984 | India . |
| 6041134 | 2/1994 | Japan . |
| 6220059 | 8/1994 | Japan . |
| 9307124 | 4/1993 | WIPO . |
| 9413677 | 6/1994 | WIPO . |
| 9421613 | 9/1994 | WIPO . |

OTHER PUBLICATIONS

*Physiology and Biochemistry of Cytokinins in Plants*, Symposium at Liblice, Czech, 1990, pp. 205–209, Nishikawa et al.
*J. Med. Chem.*, vol. 26, No. 6, 1993, pp. 838–844, Iwamura et al.
*Phytochemistry*, vol. 18, 1979, pp. 217–222, Iwamura et al.
*Chemical Abstracts*, vol. 118, 1993, abstract No. 249833e.
Registry No. 144511-80-8, *Chem. Abstr.*, 1993.
Registry No. 144511-78-4, *Chem. Abstr.*, 1993.
Registry No. 144511-72-8, *Chem. Abstr.*, 1993.
Registry No. 144511-66-0, *Chem. Abstr.*, 1993.
Registry No. 144511-65-9, *Chem. Abstr.*, 1993.
Registry No. 144511-64-8, *Chem. Abstr.*, 1993.
Registry No. 144511-63-7, *Chem. Abstr.*, 1993.
Registry No. 144511-62-6, *Chem. Abstr.*, 1993.
Registry No. 144511-49-9, *Chem. Abstr.*, 1993.
Registry No. 144511-48-8, *Chem. Abstr.*, 1993.
Registry No. 144511-45-5, *Chem. Abstr.*, 1993.
Registry No. 144511-41-1, *Chem. Abstr.*, 1993.
Registry No. 144511-40-0, *Chem. Abstr.*, 1993.
Registry No. 142716-71-0, *Chem. Abstr.*, 1993.
Registry No. 114984-45-1, *Chem. Abstr.*, 1993.
Registry No. 111243-63-1, *Chem. Abstr.*, 1993.
Registry No. 111218-85-0, *Chem. Abstr.*, 1993.
Registry No. 111218-84-9, *Chem. Abstr.*, 1993.
Registry No. 111218-82-7, *Chem. Abstr.*, 1993.
Registry No. 111218-81-6, *Chem. Abstr.*, 1993.
Registry No. 111218-79-2, *Chem. Abstr.*, 1993.
Registry No. 111218-78-1, *Chem. Abstr.*, 1993.
Registry No. 111218-77-0, *Chem. Abstr.*, 1993.
Registry No. 108799-95-7, *Chem. Abstr.*, 1993.
Registry No. 102932-27-4, *Chem. Abstr.*, 1993.
Registry No. 99272-99-8, *Chem. Abstr.*, 1993.
Registry No. 86414-79-1, *Chem. Abstr.*, 1993.
Registry No. 65962-89-2, *Chem. Abstr.*, 1993.
Registry No. 65962-88-1, *Chem. Abstr.*, 1993.
Registry No. 152358-89-9, *Chem. Abstr.*, 1993.
Registry No. 70026-96-9, *Chem. Abstr.*, 1993.
Registry No. 105217-91-2, *Chem. Abstr.*, 1993.
Registry No. 134999-86-3, *Chem. Abstr.*, 1993.
Registry No. 105217-93-4, *Chem. Abstr.*, 1993.
Registry No. 105217-92-3, *Chem. Abstr.*, 1993.
Registry No. 135000-27-0, *Chem. Abstr.*, 1993.
Registry No. 152358-87-7, *Chem. Abstr.*, 1993.
Registry No. 101901-01-3, *Chem. Abstr.*, 1993.
Registry No. 135034-87-6, *Chem. Abstr.*, 1993.
Registry No. 152358-90-2, *Chem. Abstr.*, 1993.
Registry No. 152358-86-6, *Chem. Abstr.*, 1993.
Registry No. 134999-80-7, *Chem. Abstr.*, 1993.
Registry No. 135000-29-2, *Chem. Abstr.*, 1993.
Registry No. 152358-88-8, *Chem. Abstr.*, 1993.
Registry No. 101900-99-6, *Chem. Abstr.*, 1993.
Registry No. 134999-92-1, *Chem. Abstr.*, 1993.
PCT International Search Report, PCT/US 94/00911, 1995.
*Monatshefte für Chemie*, vol. 96, 1965, pp. 542–547, Dymek et al.

(List continued on next page.)

*Primary Examiner*—Shean C. Wu
*Attorney, Agent, or Firm*—Francis J. Tinney

[57] ABSTRACT

Novel 4-substituted amino benzothieno[3,2-d]pyrimidine and 4-substituted amino[2,3-d]pyrimidine inhibitors of epidermal growth factor receptor family of tyrosine kinases are described, as well as pharmaceutical compositions of the same, which are useful in treating proliferative diseases such as cancer, synovial pannus invasion in arthritis, psoriasis, vascular restenosis and angiogenesis and additionally useful in the treatment of pancreatitis and kidney disease as well as a contraceptive agent.

2 Claims, 9 Drawing Sheets

OTHER PUBLICATIONS

*J. Chem. Soc.*, 1974, pp. 1970–1975, Bacon et al.
*J. Chem. Soc. Perkin Trans I*, 1992, pp. 2789–2811, Al–Shaar et al.
*Chemical Abstracts*, vol. 106, No. 11, 1987, abstract No. 84629e.
*Chemical Abstracts*, vol. 94, No. 17, 1981, abstract No. 139732z.
*Arch. Pharm. (Weinheim)*, vol. 326, No. 11, 1993, pp. 879–885, Monge et al.
*Tetrahedron*, vol. 48, No. 36, 1992, pp. 7689–7702, Athmani et al.
*Chemical Abstracts*, vol. 113, No. 7, 1990, abstract No. 59093n.
*Chemical Abstracts*, vol. 92, No. 17, 1980, abstract No. 146648p.
*Chemical Abstracts*, vol. 86, No. 23, 1977, abstract No. 171368f.
*Chemical Abstracts*, vol. 114, No. 17, 1991, abstract No. 164140u.
*J. Het. Chem.*, vol. 17, No. 198, 1980, pp. 923–928, Robba et al.
*Indian J. Chem.*, vol. 16B, 1978, pp. 627–629, Sangapure et al.
*Indian J. Chem.*, vol. 15B, 1977, pp. 485–487, Sangapure et al.

TRICYCLIC COMPOUNDS CAPABLE OF INHIBITING TYROSINE KINASES OF THE EPIDERMAL GROWTH FACTOR RECEPTOR FAMILY

CROSS-REFERENCE TO RELATED APPLICATIONS

This application is a continuation-in-part of U.S. application Ser. No. 186,735, filed Jan. 25, 1994 and U.S. application Ser. No. 186,745, filed Jan. 25, 1994, both of which are hereby incorporated by reference both now abandoned.

TECHNICAL FIELD

The present invention relates to tricyclic heteroaromatic compounds which inhibit the epidermal growth factor receptor and related receptors and, in particular, their tyrosine kinase enzymic activity.

BACKGROUND ART

Cancer is generally a disease of the intracellular signalling system, or signal transduction mechanism. Cells receive instructions from many extracellular sources, instructing them to either proliferate or not to proliferate. The purpose of the signal transduction system is to receive these and other signals at the cell surface, get them into the cell, and then pass the signals on to the nucleus, the cytoskeleton, and transport and protein synthesis machinery. The most common cause of cancer is a series of defects, either in these proteins, when they are mutated, or in the regulation of the quantity of the protein in the cell such that it is over or under produced. Most often, there are key lesions in the cell which lead to a constitutive state whereby the cell nucleus receives a signal to proliferate, when this signal is not actually present. This can occur through a variety of mechanisms. Sometimes the cell may start to produce an authentic growth factor for its own receptors when it should not, the so-called autocrine loop mechanism. Mutations to the cell surface receptors, which usually signal into the cell by means of tyrosine kinases, can lead to activation of the kinase in the absence of ligand, and passing of a signal which is not really there. Alternatively, many surface kinases can be overexpressed on the cell surface leading to an inappropriately strong response to a weak signal. There are many levels inside the cell at which mutation or overexpression can lead to the same spurious signal arising in the cell, and there are many other kinds of signalling defect involved in cancer. This invention touches upon cancers which are driven by the three mechanisms just described, and which involve cell surface receptors of the epidermal growth factor receptor tyrosine kinase family (EGFR). This family consists of the EGF receptor (also known as Erb-B1), the Erb-B2 receptor, and its constituitively active oncoprotein mutant Neu, the Erb-B3 receptor and the Erb-B4 receptor. Additionally, other biological processes driven through members of the EGF family of receptors can also be treated by compounds of the invention described below.

The EGFR has as its two most important ligands Epidermal Growth Factor (EGF) and Transforming Growth Factor alpha (TGFalpha). The receptors appear to have only minor functions in adult humans, but are apparently implicated in the disease process of a large portion of all cancers, especially colon and breast cancer. The closely related Erb-B2 Erb-B3 and Erb-B4 receptors have a family of Heregulins as their major ligands, and receptor overexpression and mutation have been unequivocally demonstrated as the major risk factor in poor prognosis breast cancer. Additionally, it has been demonstrated that all four of the members of this family of receptors can form heterodimeric signalling complexes with other members of the family, and that this can lead to synergistic transforming capacity if more than one member of the family is overexpressed in a malignancy. Overexpression of more than one family member has been shown to be relatively common in human malignancies.

The proliferative skin disease psoriasis has no good cure at present. It is often treated by anti-cancer agents such as methotrexate, which have very serious side effects, and which are not very effective at the toxicity-limited doses which have to be used. It is believed that TGFalpha is the major growth factor overproduced in psoriasis, since 50% of transgenic mice which overexpress TGF alpha develop psoriasis. This suggests that a good inhibitor of EGFR signalling could be used as an antipsoriatic agent, preferably, but not necessarily, by topical dosing.

EGF is a potent mitogen for renal tubule cells. Fourfold increases in both EGF urinary secretion and EGF mRNA have been noted in mice with early stage streptozoicin-induced diabetes. In addition increased expression of the EGFR has been noted in patients with proliferative glomerulonephritis (Roychaudhury et al. *Pathology* 1993, 25, 327). The compounds of the current invention should be useful in treating both proliferative glomerulonephritis and diabetes-induced renal disease.

Chronic pancreatitis in patients has been reported to correlate with large increases in expression for both EGFR and TGF alpha. (Korc et al. *Gut* 1994, 35, 1468). In patients showing a more severe form of the disease, typified by an enlargement of the head of the pancreas, there was also shown to be overexpression of the erb-B2 receptor (Friess et al. *Ann. Surg.* 1994, 220, 183). The compounds of the current invention should prove useful in the treatment of pancreatitis.

In the processes of blastocyte maturation, blastocyte implantation into the uterine endometrium, and other peri-implantation events, uterine tissues produce EGF and TGF alpha (*Taga Nippon Sanka Fujinka Gakkai Zasshi* 1992, 44, 939), have elevated levels of EGFR (Brown et al. *Endocrinology*, 1989, 124, 2882), and may well be induced to produce heparin-binding EGF by the proximity of the developing, but not arrested, blastocyte (Das et al. *Development* 1994, 120, 1071). In turn the blastocyte has quite a high level of TGF alpha and EGFR expression (Adamson *Mol. Reprod. Dev.* 1990, 27, 16). Surgical removal of the submandibular glands, the major site of EGF secretion in the body, and treatment with anti-EGFR monoclonal antibodies both greatly reduce fertility in mice (Tsutsumi et al. *J. Endocrinology* 1993, 138, 437), by reducing successful blastocyte implantation. Therefore, compounds of the current invention should prove to have useful contraceptive properties.

PCT patent application Nos. WO92/07844 published May 14, 1992 and WO92/14716 published Sep. 3, 1992 describe 2,4-diaminoquinazoline as potentiators of chemotherapeutic agents in the treatment of cancer.

PCT published application No. WO92/20642 published Nov. 26, 1992 discloses bismono- and bicyclic aryl and heteroaryl compounds which inhibit EGF and/or PDGF receptor tyrosine kinase.

It is an object of the present invention to inhibit the mitogenic effects of epidermal growth factor utilizing an effective amount of tricyclic pyrimidine derivatives, in particular fused heterocyclic pyrimidine derivatives.

It is another object of the present invention to describe tricyclic pyrimidine derivatives, in particular fused heterocyclic pyrimidine derivatives, as inhibitors of the EGF, Erb-B2 and Erb-B4 receptor tyrosine kinases.

It is yet another object of the present invention to describe tricyclic pyrimidine derivatives, in particular fused heterocyclic pyrimidine derivatives, that are useful at low dosages as inhibitors of EGF-induced mitogenesis. This therefore leads to a further object of compounds having extremely low cytotoxicity.

It is a further object of the present invention to describe tricyclic pyrimidine derivatives, in particular fused heterocyclic pyrimidine derivatives, that are useful in suppressing tumors, especially breast cancers, where mitogenesis is heavily driven by EGFR family members.

It is another object of the present invention to describe tricyclic pyrimidine derivatives, in particular fused heterocyclic pyrimidine derivatives, that have utility as chronic therapy as inhibitors of EGF-induced responses.

It is another object of the current invention to describe tricyclic pyrimidine derivatives, in particular fused heterocyclic pyrimidine derivatives, that have utility as therapeutic agents against proliferative overgrowth diseases, including but not limited to, synovial pannus invasion in arthritis, vascular restenosis and angiogenesis. Additional utility of these materials is for pancreatitis and kidney disease as well as contraception.

SUMMARY OF THE INVENTION

Described is a method to inhibit epidermal growth factor by treating, with an effective inhibiting amount, a mammal, in need thereof, a compound of the following formula:

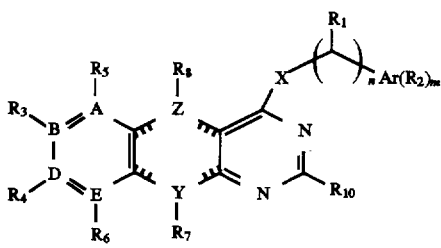

wherein: 1) Y and Z are both C (carbon), both N or one N and the other C, in which case the ring structure is a linearly fused 6,6 (5 or 6) tricycle, or 2) one of Y and Z is C=C, C=N whereupon the other one of Y or Z is simply a bond between the two aromatic rings, then the ring structure is a nonlinear 6,6 (5 or 6) tricycle, or 3) one of Y and Z is N, O or S, whereupon the other one of Y or Z is simply a bond between the two aromatic rings, then the ring structure is a fused 6,5 (5 or 6) tricycle;

A, B, D and E can all be carbon, or up to two of them can be nitrogen, whereupon the remaining atoms must be carbon, or any two contiguous positions in A–E can be a single heteroatom, N, O or S, forming a five membered fused ring, in which case one of the two remaining atoms must be carbon, and the other can be either carbon or nitrogen, except that the case where A and B taken together, and D and E taken separately are all three nitrogen atoms;

X=O, S, NH or $NR^9$, such that $R^9$=lower alkyl (1–4 carbon atoms), OH, $NH_2$, lower alkoxy (1–4 carbon atoms) or lower monoalkylamino (1–4 carbon atoms);

$R^1$=H or lower alkyl;

n=0, 1 or 2;

if n=2, $R^1$ can be independently H or lower alkyl on either linking carbon atom, and both R and S stereocentres on either linker are included;

$R^2$ is lower alkyl (1–4 carbon atoms), cycloalkyl (3–8 carbon atoms), lower alkoxy (1–4 carbon atoms), cycloalkoxy (3–8 carbon atoms), nitro, halo, lower perfluoroalkyl (1–4 carbon atoms), hydroxy, lower acyloxy (1–4 carbon atoms; —O—C(O)—R), amino, lower mono or dialkylamino (1–4 carbon atoms), lower mono or dicycloalkylamino (3–8 carbon atoms), hydroxymethyl, lower acyl (1–4 carbon atoms; —C(O) R), cyano, lower thioalkyl (1–4 carbon atoms), lower sulfinylalkyl alkyl (1–4 carbon atoms), lower sulfonylalkyl (1–4 carbon atoms), thiocycloalkyl (3–8 carbon atoms), sulfinylcycloalkyl (3–8 carbon atoms), sulfonylcycloalkyl (3–8 carbon atoms), mercapto, lower alkoxycarbonyl (1–4 carbon atoms), cycloalkoxycarbonyl (3–8 carbon atoms), lower alkenyl (2–4 carbon atoms), cycloalkenyl (4–8 carbon atoms), lower alkynyl (2–4 carbon atoms), or two $R^2$ taken together can form a carbocyclic ring of 5–7 members; and m=0–3, wherein Ar is phenyl, thienyl, furanyl, pyrrolyl, pyridyl, pyrimidyl, imidazoyl, pyrazinyl, oxazolyl, thiazolyl, naphthyl, benzothienyl, benzofuranyl, indolyl, quinolinyl, isoquinolinyl and quinazolinyl;

$R^3$, $R^4$, $R^5$ and $R^6$ are independently, not present, H, lower alkyl (1–4 carbon atoms), cycloalkyl (3–8 carbon atoms), lower alkoxy (1–4 carbon atoms), cycloalkoxy (3–8 carbon atoms), hydroxy, lower acyloxy (1–4 carbon atoms), amino, lower mono or dialkylamino (1–4 carbon atoms), lower mono or dicycloalkylamino (3–8 carbon atoms), lower alkyl (1–4 carbon atoms) or cycloalkyl (3–8 carbon atoms), carbonato (—OC(O) OR) where R is alkyl of from 1–4 carbon atoms or cycloalkyl alkyl of from 3–8 carbon atoms;

or ureido or thioureido or N— or O— linked urethane any one of which is optionally substituted by mono or di-lower alkyl (1–4 carbon atoms) or cycloalkyl alkyl (3–8 carbon atoms);

lower thioalkyl (1–4 carbon atoms), thiocycloalkyl (3–8 carbon atoms), mercapto, lower alkenyl (2–4 carbon atoms), hydrazino, N— and/or N'— mono- or di lower alkylhydrazino (1–4 carbon atoms), lower acylamino (1–4 carbon atoms), hydroxylamino, N— and/or O— mono- or di lower alkylhydroxylamino (1–4 carbon atoms), or taken together can be methylene-, ethylene- or propylenedioxy, or taken together form a fused pyrrolidine, tetrahydrofuranyl, piperidinyl, piperazinyl, morpholino or thiomorpholino ring;

$R^7$ and $R^8$ can be independently as appropriate, lone pairs of electrons, H, or lower alkyl;

any lower alkyl group substituent on any of the substituents in $R^3$–$R^8$ which contain such a moiety can be optionally substituted with one or more of hydroxy, amino, lower monoalkylamino, lower dialkylamino, N-pyrrolidyl, N-piperidinyl, N-pyridinium, N-morpholino, N-thiomorpholino or N-piperazino groups;

if one or two of A through E are N, then if any of $R^3$–$R^6$ is on a neighboring C atom to one of the N atoms, that substituent cannot be either OH or SH; and $R^{10}$ is H or lower alkyl (1–4 carbon atoms), amino or lower mono- or dialkylamino (1–4 carbon atoms);

if any of the substitutents $R^1$, $R^2$, $R^3$ or $R^4$ contain chiral centers, or in the case of $R^1$ create chiral centers on the linking atoms, then all stereoisomers thereof both separately and as racemic and/or diastereoisomeric mixtures are included;

or a pharmaceutical salt or hydrate thereof.

The invention pertains to the compounds, per se:

with the proviso that the ring containing A–E is aromatic;

and with the proviso that if A and B taken together and E are nitrogen, and if neither Y nor Z is a heteroatom, and if X=NH, and n=1, and $R^1$=H and Ar=Ph, then one of the imidazole nitrogen atoms must have a substituent from the $R^3$–$R^6$ group other than lone pair or hydrogen;

and with the proviso that if A–E are carbon, and Y is a bond, and Z is sulfur, and X=NH, and n=0, then Ar cannot be unsubstituted phenyl, unsubstituted or substituted pyridyl or unsubstituted or substituted pyrimidyl.

Preferably, the compounds are subject to additional provisos:

with the proviso that if A–E are carbon, Y and Z cannot be both carbon or one ethylidene and the other a bond, unless at least one of $R^3$–$R^6$ is not hydrogen;

with the proviso that if A–E are carbon one of Y and Z cannot be nitrogen, substituted with hydrogen, and the other a bond.

DESCRIPTION OF PREFERRED EMBODIMENTS

Nomenclature and Numbering as used Herein

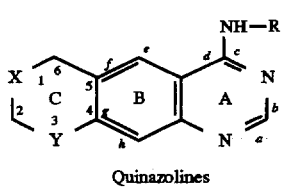

Quinazolines

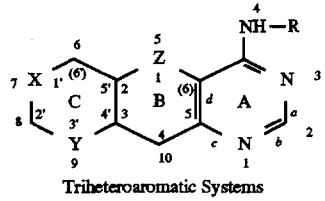

Triheteroaromatic Systems

Figure 1:
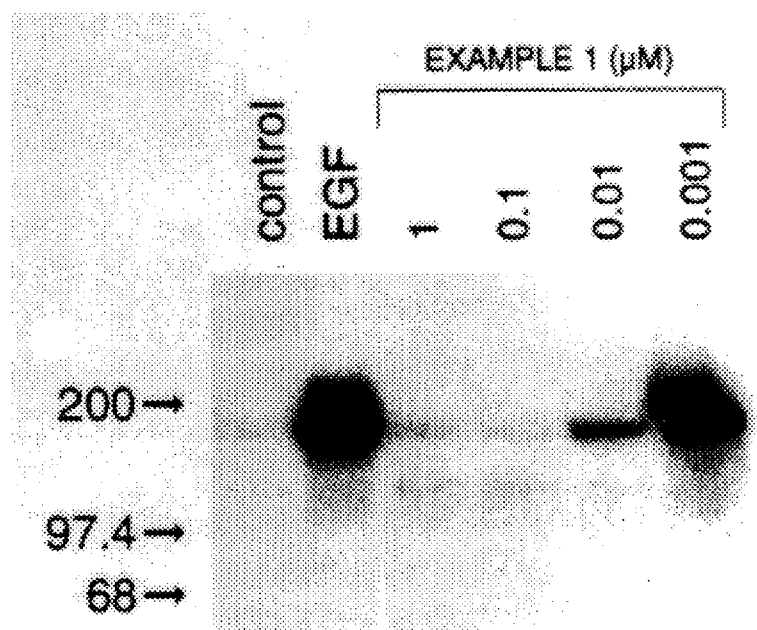
FIG. 1 is an effect of Example 1 on EGF receptor autophosphorylation in A431 human epidermoid carcinoma.
Figure 2:
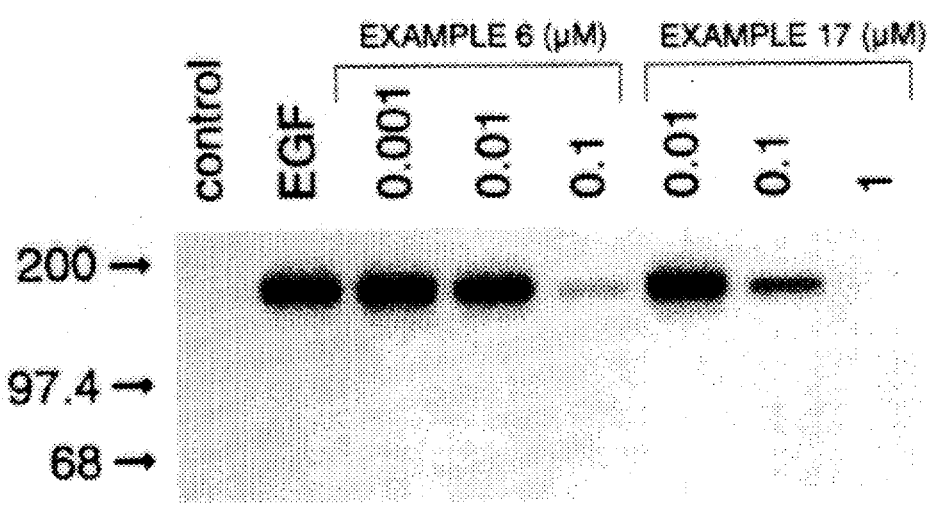
FIG. 2 is an effect of Examples 6 and 17 on EGF receptor autophosphorylation in A431 human epidermoid carcinoma.
Figure 3:
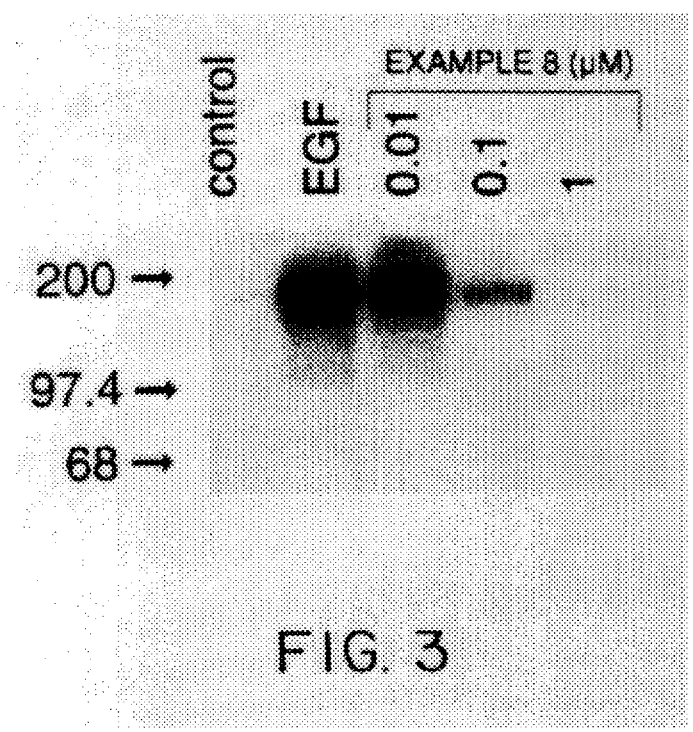
FIG. 3 is an effect of Example 8 on EGF receptor autophosphorylation in A431 human epidermoid carcinoma.
Figure 4:
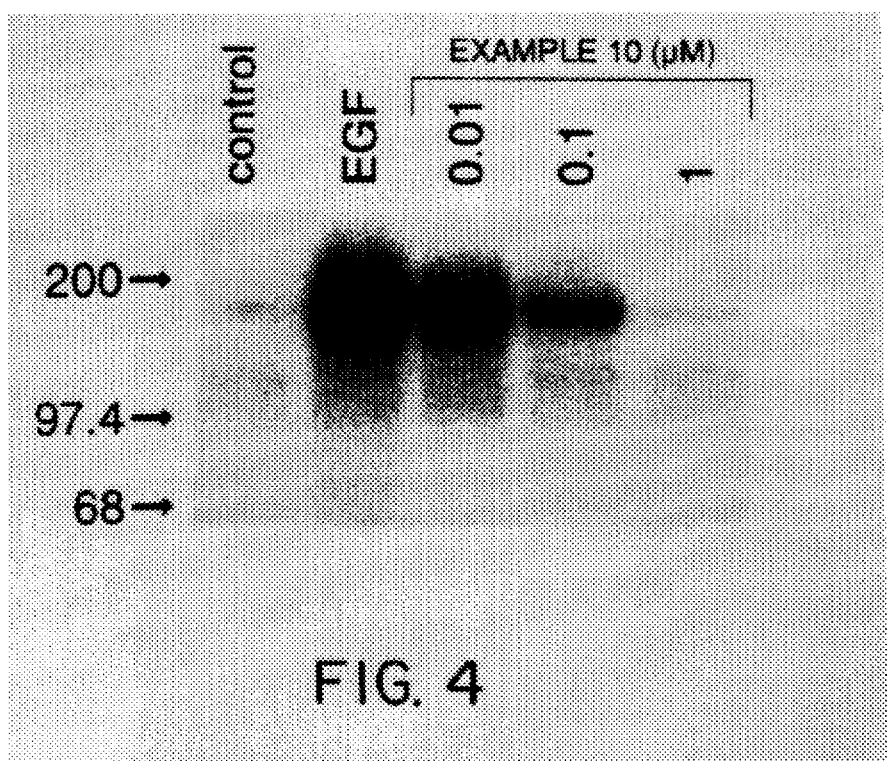
FIG. 4 is an effect of Example 10 on EGF receptor autophosphorylation in A431 human epidermoid carcinoma.
Figure 5:
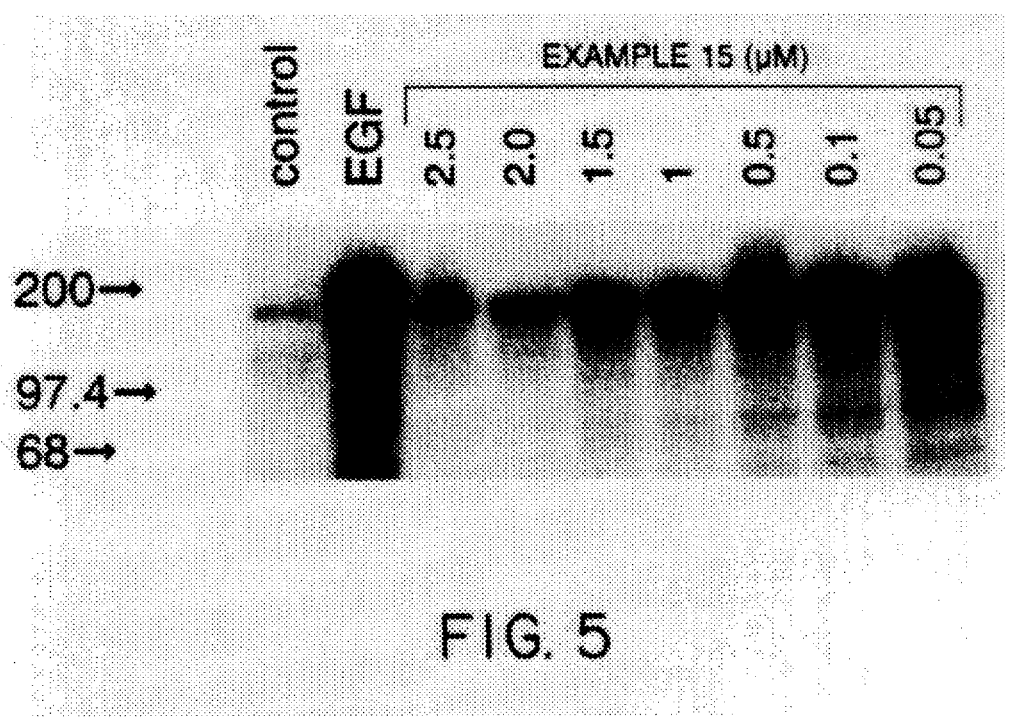
FIG. 5 is an effect of Example 15 on EGF receptor autophosphorylation in A431 human epidermoid carcinoma.
Figure 6:
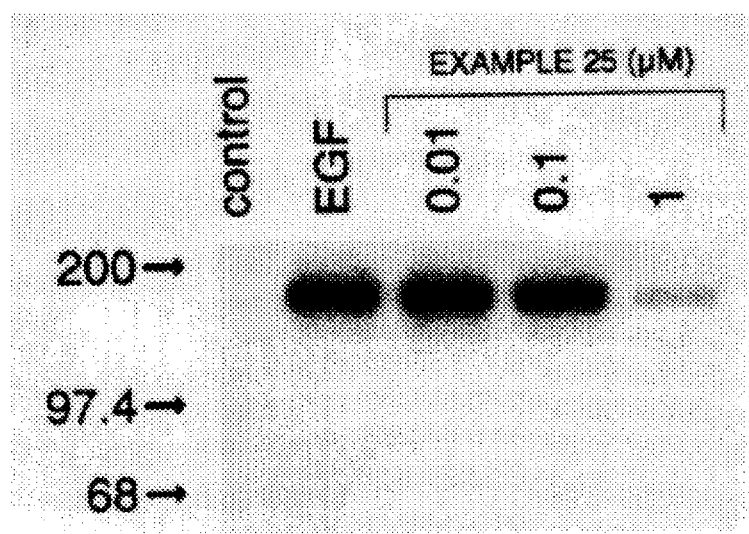
FIG. 6 is an effect of Example 25 on EGF receptor autophosphorylation in A431 human epidermoid carcinoma.
Figure 7:
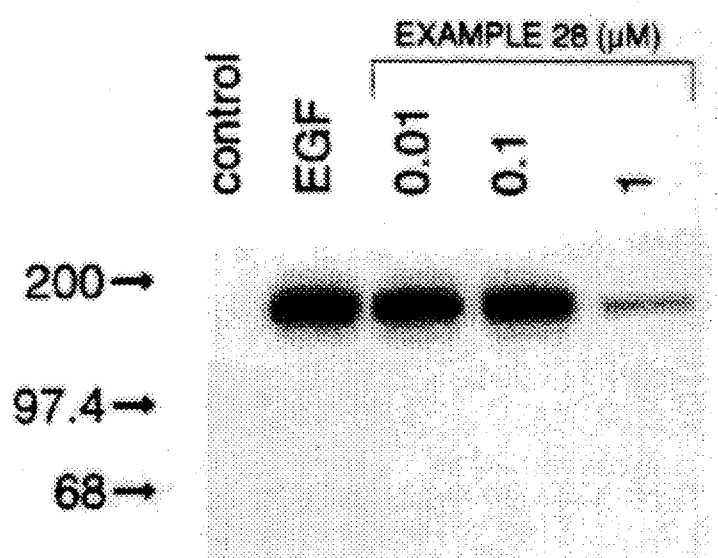
FIG. 7 is an effect of Example 28 on EGF receptor autophosphorylation in A431 human epidermoid carcinoma.
Figure 8:
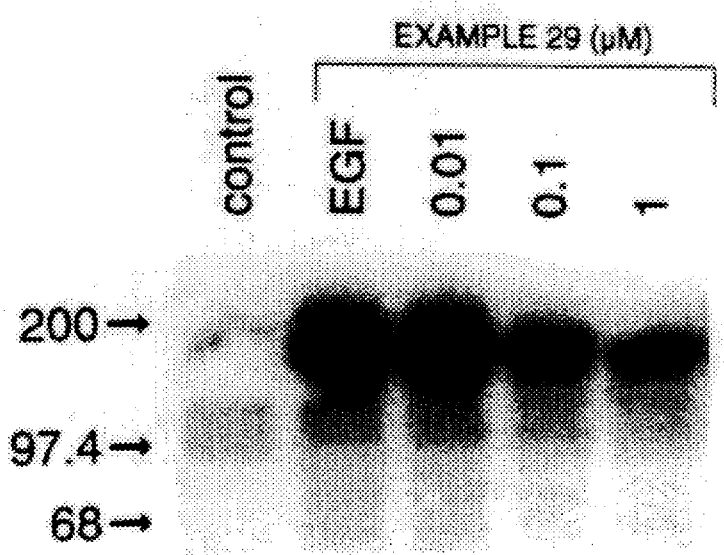
FIG. 8 is an effect of Example 29 on EGF receptor autophosphorylation in A431 human epidermoid carcinoma.

Nomenclature. All tricycles containing a benzene ring fused directly to the pyrimidine ring have been named as quinazoline derivatives. All other tricycles are named as pyrimidine derivatives, either fused to a bicyclic nucleus such as indole or benzothiophene, or to two separate monocyclic heterocycles such as pyridothiophene. In such cases the first ring given is always the one distal to the pyrimidine ring.

Ring fusion numbers. For quinazoline derivatives the quinazoline nucleus is lettered counterclockwise with the N1—C2 bond being a, and the three possible ring fusion positions being f, g and h. The C-ring is numbered 1⅚ from its highest atomic weight heteroatom, with the ring fusion numbering being decided by the numbered bridgehead atom which first meets the counterclockwise flow of the quinazoline lettering.

For systems with three fused heteroaromatic rings, the pyrimidine ring (A) is always chosen as the root system and is d-fused to the B-ring lettering in a clockwise direction. The central B-ring is numbered 1–5/6, starting at the heteroatom, and going first via the B/C ring junction and then the B/A ring junction. It can be numbered either clockwise, when the heteroatom is at the bottom, or counterclockwise, when the heteroatom is at the top, (as is illustrated above), and the ring fusion numbering is decided by the numbered bridgehead atom which first meets the clockwise flow of the pyrimidine lettering. The C-ring is numbered 1'–5'/6' from the highest priority heteroatom, towards lower priority heteroatoms if present, and if there are no other heteroatoms, in the direction which gives the lowest numbering to the ring junction. The first C-ring fusion number is that of the bridgehead atom which has the lowest numbering in the B-ring numbering system. In the first set of parentheses the C-ring numbers of the B/C bridgehead atoms are given, followed after the colon by the B-ring numbers for the same atoms. The second set of parentheses contain the B-ring numbers for the A/B-bridgehead atoms, followed after the dash by the shared bond in the A-ring lettering system. Thus, the example above illustrates a [5',4':2,3] [5,6-d] tricyclic system.

Substituent Numbering. In all of the examples, the numbering is taken from the bottom nitrogen of the pyrimidine A ring as 1, and then all nonbridgehead atoms are counted consecutively in a counterclockwise direction from that point, as illustrated above for a 6,6,6-system by the bolded numbers.

1. A preferred form of the invention has n=0, A–E, Y & Z being carbon, X=NH, Ar a benzene ring, optionally substituted, and $R^5$–$R^8$ hydrogen. A suitable ring structure is:

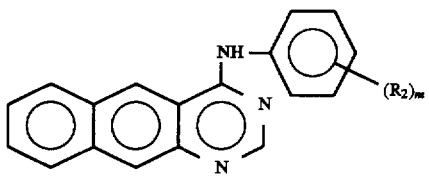

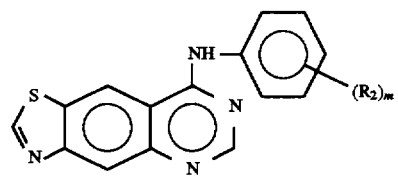

2. Another preferred form of the invention has, n=0 or 1, with one of A & B or D & E taken together as oxygen, the remaining pair both being carbon, along with Y and Z, X=NH, Ar a benzene ring, optionally substituted, and $R^5$–$R^8$ hydrogen or a lone pair of electrons where appropriate. A suitable ring structure is:

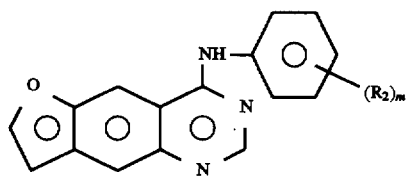

3. Another preferred form of the invention has, n=0 or 1, with one of A & B or D & E taken together as sulfur, the remaining pair both being carbon, along with Y and Z, X=NH, Ar a benzene ring, optionally substituted, and $R^5$–$R^8$ hydrogen or a lone pair of electrons where appropriate.

4. Another preferred form of the invention has, n=0 or 1, with one of A & B or D & E taken together as nitrogen, the remaining pair both being carbon, along with Y and Z, X=NH, Ar a benzene ring, optionally substituted, and $R^5$–$R^8$ hydrogen or optionally lower alkyl if on nitrogen. A suitable ring structure is:

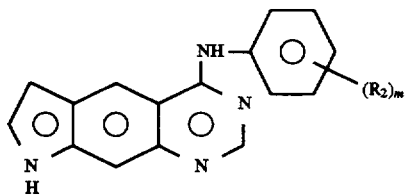

5. Another preferred form of the invention has n=0 or 1, A & B taken together as oxygen, and E as nitrogen, or D & E taken together as oxygen and A as nitrogen, Y and Z both carbon, X=NH, Ar a benzene ring, optionally substituted, and $R^5$–$R^8$ hydrogen or a lone pair of electrons where appropriate.

6. Another preferred form of the invention has n=0 or 1, A & B taken together as sulfur, and E as nitrogen, or D & E taken together as sulfur and A as nitrogen, Y and Z both carbon, X=NH, Ar a benzene ring, optionally substituted, and $R^5$–$R^8$ hydrogen or a lone pair of electrons where appropriate. A suitable ring structure is:

7. Another preferred form of the invention has n=0 or 1, A & B taken together, and E as nitrogen, Y and Z both carbon, X=NH, Ar a benzene ring, optionally substituted, and $R^5$–$R^8$ hydrogen or optionally lower alkyl if on nitrogen, or a lone pair of electrons where appropriate.

8. Another preferred form of the invention has n=0 or 1, A & B taken together as oxygen, and D as nitrogen, or D & E taken together as oxygen and B as nitrogen, Y and Z both carbon, X=NH, Ar a benzene ring, optionally substituted, and $R^5$–$R^8$ hydrogen, lower alkyl, or a lone pair of electrons where appropriate.

9. Another preferred form of the invention has n=0 or 1, A & B taken together as sulfur, and D as nitrogen, or D & E taken together as sulfur and B as nitrogen, Y and Z both carbon, X=NH, Ar a benzene ring, optionally substituted, and $R^5$–$R^8$ hydrogen, lower alkyl, or a lone pair of electrons where appropriate.

10. Another preferred form of the invention has n=0 or 1, A & B taken together, and D as nitrogen, or D & E taken together, and B as nitrogen, Y and Z both carbon, X=NH, Ar a benzene ring, optionally substituted, and $R^5$–$R^8$ hydrogen, lower alkyl, or a lone pair of electrons where appropriate. A suitable ring structure is:

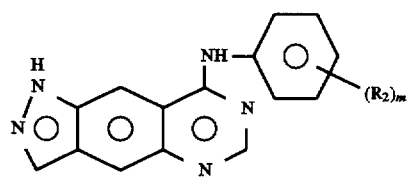

11. Another preferred form of the invention has n=0, A & B taken together, with D & E taken separately as nitrogen, Y and Z both carbon, X=NH, Ar a benzene ring, optionally substituted, and $R^5$–$R^8$ hydrogen or optionally lower alkyl if on nitrogen, or a lone pair of electrons where appropriate.

12. Another preferred form of the invention has n=0 or 1, with one of A, B, D or E as nitrogen, the remaining three being carbon, along with Y and Z, X=NH, Ar a benzene ring, optionally substituted, and $R^5$–$R^8$ hydrogen or a lone pair of electrons where appropriate.

13. Another preferred form of the invention has n=0, with any two of A, B, D or E as nitrogen, the remaining two being carbon, along with Y and Z, X =NH, Ar a benzene ring, optionally substituted, and $R^5$–$R^8$ hydrogen or a lone pair of electrons where appropriate.

14. Another preferred form of the invention has n=0, A–E, and one of Y and Z being carbon, the other nitrogen, X=NH, Ar a benzene ring, optionally substituted, and $R^5$–$R^8$ hydrogen or a lone pair of electrons where appropriate. A suitable ring structure is:

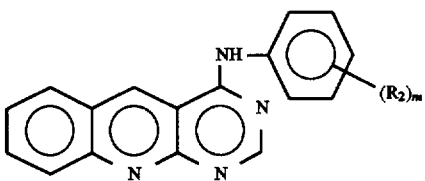

15. Another preferred form of the invention has, n=0 or 1, with one of A & B or D & E taken together as oxygen, the remaining pair both being carbon, along with one of Y and Z, the other being nitrogen, X=NH, Ar a benzene ring, optionally substituted, and $R^5$-$R^8$ hydrogen or a lone pair of electrons where appropriate. A suitable structure is:

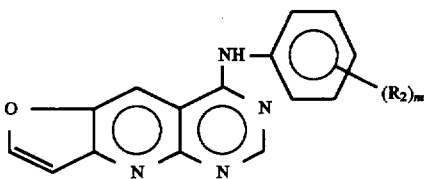

16. Another preferred form of the invention has, n=0 or 1, with one of A & B or D & E taken together as sulfur, the remaining pair both being carbon, along with one of Y and Z, the other being nitrogen, X=NH, Ar a benzene ring, optionally substituted, and $R^5$-$R^8$ hydrogen or a lone pair of electrons where appropriate.

17. Another preferred form of the invention has, n=0 or 1, with one of A & B or D & E taken together as nitrogen, the remaining pair both being carbon, along with one of Y and Z, the other being nitrogen, X=NH, Ar a benzene ring, optionally substituted, and $R^5$-$R^8$ hydrogen, or optionally lower alkyl if on nitrogen in the pyrrole ring, or a lone pair of electrons where appropriate.

18. Another preferred form of the invention has n=0 or 1, A & B taken together as oxygen, and E as nitrogen, or D & E taken together as oxygen and A as nitrogen, one of Y and Z being carbon the other nitrogen, X=NH, Ar a benzene ring, optionally substituted, and $R^5$-$R^8$ hydrogen or a lone pair of electrons where appropriate. A suitable ring structure is:

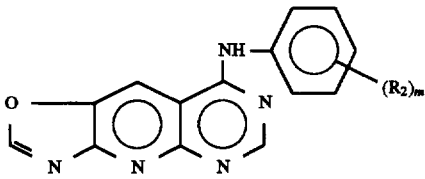

19. Another preferred form of the invention has n=0 or 1, A & B taken together as sulfur, and E as nitrogen, or D & E taken together as sulfur and A as nitrogen, one of Y and Z being carbon the other nitrogen, X=NH, Ar a benzene ring, optionally substituted, and $R^5$-$R^8$ hydrogen or a lone pair of electrons where appropriate.

20. Another preferred form of the invention has n=0 or 1, A & B taken together, and E as nitrogen, one of Y and Z being carbon the other nitrogen, X =NH, Ar a benzene ring, optionally substituted, and $R^5$-$R^8$ hydrogen or optionally lower alkyl if on nitrogen or a lone pair of electrons where appropriate.

21. Another preferred form of the invention has n=0 or 1, A & B taken together as oxygen, and D as nitrogen, or D & E taken together as oxygen and B as nitrogen, one of Y and Z being carbon the other nitrogen, X=NH, Ar a benzene ring, optionally substituted, and $R^5$-$R^8$ hydrogen, lower alkyl, or a lone pair of electrons where appropriate.

22. Another preferred form of the invention has n=0 or 1, A & B taken together as sulfur, and D as nitrogen, or D & E taken together as sulfur and B as nitrogen, one of Y and Z being carbon the other nitrogen, X=NH, Ar a benzene ring, optionally substituted, and $R^5$-$R^8$ hydrogen, lower alkyl, or a lone pair of electrons where appropriate.

23. Another preferred form of the invention has n=0 or 1, A & B taken together, and D as nitrogen, or D & E taken together, and B as nitrogen, one of Y and Z being carbon the other nitrogen, X=NH, Ar a benzene ring, optionally substituted, and $R^5$-$R^8$ hydrogen, lower alkyl, or a lone pair of electrons where appropriate.

24. Another preferred form of the invention has n=0 or 1, with one of A, B, D or E as nitrogen, the remaining three being carbon, along with one of Y and Z, the other being nitrogen, X=NH, Ar a benzene ring, optionally substituted, and $R^5$-$R^8$ hydrogen or a lone pair of electrons where appropriate. A suitable ring structure is:

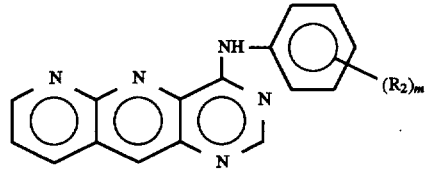

25. Another preferred form of the invention has n=0, with any two of A, B, D or E as nitrogen, the remaining two being carbon, along with one of Y and Z, the other being nitrogen, X=NH, Ar a benzene ring, optionally substituted, and $R^5$-$R^8$ hydrogen or a lone pair of electrons where appropriate.

26. A preferred form of the invention has n =0, A–E carbon, Y and Z nitrogen, X=NH, Ar a benzene ring, optionally substituted, and $R^5$-$R^8$ hydrogen or a lone pair of electrons where appropriate. A suitable ring structure is:

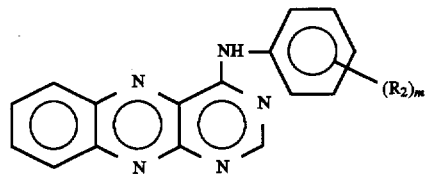

27. Another preferred form of the invention has n=0 or 1, A–E being carbon, one of Y & Z being ethylidene, X=NH, Ar a benzene ring, optionally substituted, and $R^5$-$R^8$ hydrogen. A suitable ring structure is:

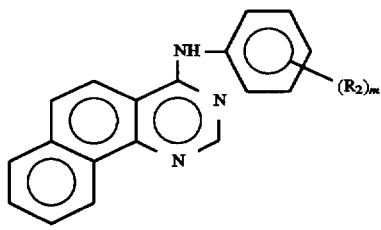

28. Another preferred form of the invention has, n=0 or 1, with one of A & B or D a E taken together as oxygen, the remaining pair both being carbon, one of Y & Z being ethylidene, X=NH, Ar a benzene ring, optionally substituted, and R⁵-R⁸ hydrogen or a lone pair of electrons where appropriate.

29. Another preferred form of the invention has, n=0 or 1, with one of A & B or D & E taken together as sulfur, the remaining pair both being carbon, one of Y a Z being ethylidene, X=NH, Ar a benzene ring, optionally substituted, and R⁵-R⁸ hydrogen or a lone pair of electrons where appropriate.

30. Another preferred form of the invention has, n=0 or 1, with one of A & B or D & E taken together as nitrogen, the remaining pair both being carbon, one of Y a Z being ethylidene, X=NH, Ar a benzene ring, optionally substituted, and R⁵-R⁸ hydrogen or optionally lower alkyl if on nitrogen.

31. Another preferred form of the invention has n=0 or 1, A & B taken together as oxygen, and E as nitrogen, or D & E taken together as oxygen and A as nitrogen, one of Y & Z being ethylidene, X=NH, Ar a benzene ring, optionally substituted, and R⁵-R⁸ hydrogen or a lone pair of electrons where appropriate.

32. Another preferred form of the invention has n=0 or 1, A & B taken together as sulfur, and E as nitrogen, or D a E taken together as sulfur and A as nitrogen, one of Y a Z being ethylidene, X=NH, Ar a benzene ring, optionally substituted, and R⁵-R⁸ hydrogen or a lone pair of electrons where appropriate.

33. Another preferred form of the invention has n=0, A & B taken together, and E as nitrogen, one of Y a Z being ethylidene, X=NH, Ar a benzene ring, optionally substituted, and R⁵-R⁸ hydrogen or optionally lower alkyl if on nitrogen or a lone pair of electrons where appropriate. A suitable ring structure is:

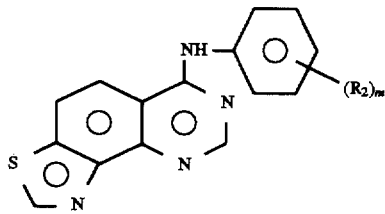

34. Another preferred form of the invention has n=0 or 1, A & B taken together as oxygen, and D as nitrogen, or D & E taken together as oxygen and B as nitrogen, one of Y & Z being ethylidene, X=NH, Ar a benzene ring, optionally substituted, and R⁵-R⁸ hydrogen, lower alkyl, or a lone pair of electrons where appropriate.

35. Another preferred form of the invention has n=0 or 1, A & B taken together as sulfur, and D as nitrogen, or D & E taken together as sulfur and B as nitrogen, one of Y & Z being ethylidene, X=NH, Ar a benzene ring, optionally substituted, and R⁵-R⁸ hydrogen, lower alkyl, or a lone pair of electrons where appropriate. A suitable ring structure is:

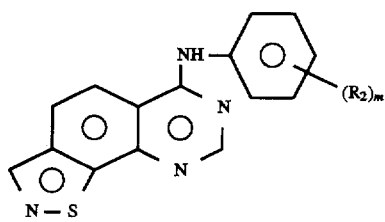

36. Another preferred form of the invention has n=0 or 1, A & B taken together, and D as nitrogen, or D & E taken together, and B as nitrogen, one of Y & Z being ethylidene, X=NH, Ar a benzene ring, optionally substituted, and R⁵-R⁸ hydrogen, lower alkyl, or a lone pair of electrons where appropriate.

37. Another preferred form of the invention has n=0 or 1, with one of A, B, D or E as nitrogen, the remaining three being carbon, one of Y & Z being ethylidene, X=NH, Ar a benzene ring, optionally substituted, and R⁵-R⁸ hydrogen or a lone pair of electrons where appropriate.

38. Another preferred form of the invention has n=0, with any two of A, B, D or E as nitrogen, the remaining two being carbon, one of Y & Z being ethylidene, X=NH, Ar a benzene ring, optionally substituted, and R⁵-R⁸ hydrogen or a lone pair of electrons where appropriate.

39. Another preferred form of the invention has n=0 or 1, A-E being carbon, one of Y & Z being sulfur, X=NH, Ar a benzene ring, optionally substituted, and R⁵-R⁸ hydrogen or a lone pair of electrons where appropriate. A suitable ring structure is:

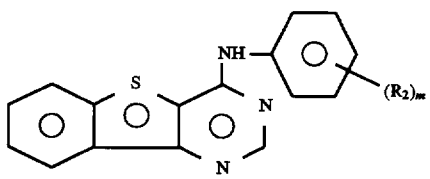

40. Another preferred form of the invention has, n=0 or 1, with one of A & B or D & E taken together as oxygen, the remaining pair both being carbon, one of Y & Z being sulfur, X=NH, Ar a benzene ring, optionally substituted, and R⁵-R⁸ hydrogen or a lone pair of electrons where appropriate.

41. Another preferred form of the invention has, n=0 or 1, with one of A & B or D & E taken together as sulfur, the remaining pair both being carbon, one of Y & Z being sulfur, X=NH, Ar a benzene ring, optionally substituted, and R⁵-R⁸ hydrogen or a lone pair of electrons where appropriate.

42. Another preferred form of the invention has, n=0 or 1, with one of A & B or D & E taken together as nitrogen, the remaining pair both being carbon, one of Y & Z being sulfur, X=NH, Ar a benzene ring, optionally substituted, and R⁵-R⁸ hydrogen or a lone pair of electrons where appropriate or optionally lower alkyl if on nitrogen.

43. Another preferred form of the invention has n=0 or 1, A & B taken together as oxygen, and E as nitrogen, or D & E taken together as oxygen and A as nitrogen, one of Y & Z being sulfur, X=NH, Ar a benzene ring, optionally substituted, and R⁵-R⁸ hydrogen or a lone pair of electrons where appropriate.

44. Another preferred form of the invention has n=0 or 1, A & B taken together as sulfur, and E as nitrogen, or D a E taken together as sulfur and A as nitrogen, one of Y & Z being sulfur, X=NH, Ar a benzene ring, optionally substituted, and $R^5$-$R^8$ hydrogen or a lone pair of electrons where appropriate. A suitable ring structure is:

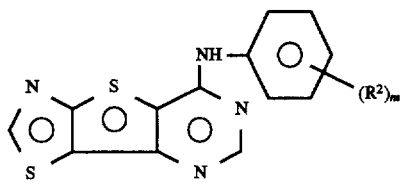

45. Another preferred form of the invention has n=0, A & B taken together, and E as nitrogen, one of Y & Z being sulfur, X=NH, Ar a benzene ring, optionally substituted, and $R^5$-$R^8$ hydrogen or optionally lower alkyl if on nitrogen, or a lone pair of electrons where appropriate.

46. Another preferred form of the invention has n=0 or 1, A & B taken together as oxygen, and D as nitrogen, or D & E taken together as oxygen and B as nitrogen, one of Y & Z being sulfur, X=NH, Ar a benzene ring, optionally substituted, and $R^5$-$R^8$ hydrogen, lower alkyl, or a lone pair of electrons where appropriate.

47. Another preferred form of the invention has n=0 or 1, A & B taken together as sulfur, and D as nitrogen, or D & E taken together as sulfur and B as nitrogen, one of Y & Z being sulfur, X=NH, Ar a benzene ring, optionally substituted, and $R^5$-$R^8$ hydrogen, lower alkyl, or a lone pair of electrons where appropriate.

48. Another preferred form of the invention has n=0 or 1, A & B taken together, and D as nitrogen, or D & E taken together, and B as nitrogen, one of Y & Z being sulfur, X=NH, Ar a benzene ring, optionally substituted, and $R^5$-$R^8$ hydrogen, lower alkyl, or a lone pair of electrons where appropriate.

49. Another preferred form of the invention has n=0 or 1, with one of A, B, D or E as nitrogen, the remaining three being carbon, one of Y & Z being sulfur, X=NH, Ar a benzene ring, optionally substituted, and $R^5$-$R^8$ hydrogen or a lone pair of electrons where appropriate.

50. Another preferred form of the invention has n=0 or 1, A-E being carbon, one of Y & Z being nitrogen, X=NH, Ar a benzene ring, optionally substituted, and $R^5$-$R^8$ hydrogen, or optionally lower alkyl if on nitrogen.

51. Another preferred form of the invention has, n=0 or 1, with one of A & B or D & E taken together as oxygen, the remaining pair both being carbon, one of Y & Z being nitrogen, X=NH, Ar a benzene ring, optionally substituted, and $R^5$-$R^8$ hydrogen or a lone pair of electrons where appropriate, or optionally lower alkyl if on nitrogen.

52. Another preferred form of the invention has, n=0 or 1, with one of A & B or D & E taken together as sulfur, the remaining pair both being carbon, one of Y a Z being nitrogen, Ar a benzene ring, optionally substituted, and $R^5$-$R^8$ hydrogen or a lone pair of electrons where appropriate, or optionally lower alkyl if on nitrogen.

53. Another preferred form of the invention has, n=0 or 1, with one of A & B or D & E taken together as nitrogen, the remaining pair both being carbon, one of Y a Z being nitrogen, X=NH, Ar a benzene ring, optionally substituted, and $R^5$-$R^8$ hydrogen or optionally lower alkyl if on nitrogen.

54. Another preferred form of the invention has n=0 or 1, A & B taken together as oxygen, and E as nitrogen, or D & E taken together as oxygen and A as nitrogen, one of Y & Z being nitrogen, X=NH, Ar a benzene ring, optionally substituted, and $R^5$-$R^8$ hydrogen or a lone pair of electrons where appropriate, or optionally lower alkyl if on nitrogen. A suitable ring structure is:

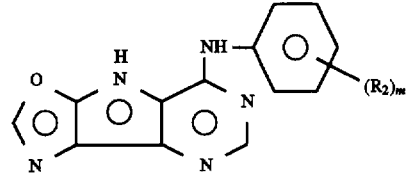

55. Another preferred form of the invention has n=0 or 1, A & B taken together as sulfur, and E as nitrogen, or D a E taken together as sulfur and A as nitrogen, one of Y & Z being nitrogen, X=NH, Ar a benzene ring, optionally substituted, and $R^5$-$R^8$ hydrogen or a lone pair of electrons where appropriate, or optionally lower alkyl if on nitrogen.

56. Another preferred form of the invention has n=0, A & B taken together, and E as nitrogen, one of Y & Z being nitrogen, X=NH, Ar a benzene ring, optionally substituted, and $R^5$-$R^8$ hydrogen or optionally lower alkyl if on nitrogen or a lone pair of electrons where appropriate.

57. Another preferred form of the invention has n=0 or 1, A & B taken together as oxygen, and D as nitrogen, or D & E taken together as oxygen and B as nitrogen, one of Y & Z being nitrogen, X=NH, Ar a benzene ring, optionally substituted, and $R^5$-$R^8$ hydrogen, lower alkyl, or a lone pair of electrons where appropriate.

58. Another preferred form of the invention has n=0 or 1, A & B taken together as sulfur, and D as nitrogen, or D & E taken together as sulfur and B as nitrogen, one of Y & Z being nitrogen, X=NH, Ar a benzene ring, optionally substituted, and $R^5$-$R^8$ hydrogen, lower alkyl, or a lone pair of electrons where appropriate.

59. Another preferred form of the invention has n=0 or 1, A & B taken together, and D as nitrogen, or D & E taken together, and B as nitrogen, one of Y & Z being nitrogen, X=NH, Ar a benzene ring, optionally substituted, and $R^5$-$R^8$ hydrogen, lower alkyl, or a lone pair of electrons where appropriate.

60. Another preferred form of the invention has n=0 or 1, with one of A, B, D or E as nitrogen, the remaining three being carbon, one of Y & Z being nitrogen, X=NH, Ar a benzene ring, optionally substituted, and $R^5$-$R^8$ hydrogen or a lone pair of electrons where appropriate.

61. Another preferred form of the invention has n=0 or 1, A-E being carbon, one of Y & Z being oxygen, X=NH, Ar a benzene ring, optionally substituted, and $R^5$-$R^8$ hydrogen or a lone pair of electrons where appropriate. A suitable ring structure is:

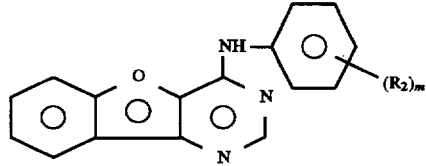

62. Another preferred form of the invention has, n=0 or 1, with one of A & B or D & E taken together as oxygen, the remaining pair both being carbon, one of Y & Z being oxygen, X=NH, Ar a benzene ring, optionally substituted, and $R^5$-$R^8$ hydrogen or a lone pair of electrons where appropriate.

63. Another preferred form of the invention has, n=0 or 1, with one of A & B or D & E taken together as sulfur, the remaining pair both being carbon, one of Y & Z being oxygen, X=NH, Ar a benzene ring, optionally substituted, and $R^5$–$R^8$ hydrogen or a lone pair of electrons where appropriate.

64. Another preferred form of the invention has, n=0 or 1, with one of A & B or D & E taken together as nitrogen, the remaining pair both being carbon, one of Y & Z being oxygen, X=NH, Ar a benzene ring, optionally substituted, and $R^5$–$R^8$ hydrogen or a lone pair of electrons where appropriate or optionally lower alkyl if on nitrogen.

65. Another preferred form of the invention has n=0 or 1, A & B taken together as oxygen, and E as nitrogen, or D & E taken together as oxygen and A as nitrogen, one of Y & Z being oxygen, X=NH, Ar a benzene ring, optionally substituted, and $R^5$–$R^8$ hydrogen or a lone pair of electrons where appropriate.

66. Another preferred form of the invention has n=0 or 1, A & B taken together as sulfur, and E as nitrogen, or D & E taken together as sulfur and A as nitrogen, one of Y & Z being oxygen, X=NH, Ar a benzene ring, optionally substituted, and $R^5$–$R^8$ hydrogen or a lone pair of electrons where appropriate. A suitable ring structure is:

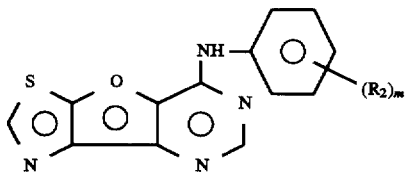

67. Another preferred form of the invention has n=0, A & B taken together, and E as nitrogen, one of Y & Z being oxygen, X=NH, Ar a benzene ring, optionally substituted, and $R^5$–$R^8$ hydrogen or optionally lower alkyl if on nitrogen or a lone pair where appropriate.

68. Another preferred form of the invention has n=0 or 1, A & B taken together as oxygen, and D as nitrogen, or D & E taken together as oxygen and B as nitrogen, one of Y & Z being oxygen, X=NH, Ar a benzene ring, optionally substituted, and $R^5$–$R^8$ hydrogen, lower alkyl, or a lone pair of electrons where appropriate.

69. Another preferred form of the invention has n=0 or 1, A & B taken together as sulfur, and D as nitrogen, or D & E taken together as sulfur and B as nitrogen, one of Y & Z being oxygen, X=NH, Ar a benzene ring, optionally substituted, and $R^5$–$R^8$ hydrogen, lower alkyl, or a lone pair of electrons where appropriate.

70. Another preferred form of the invention has n=0 or 1, A & B taken together, and D as nitrogen, or D & E taken together, and B as nitrogen, one of Y & Z being oxygen, X=NH, Ar a benzene ring, optionally substituted, and $R^5$–$R^8$ hydrogen, lower alkyl, or a lone pair of electrons where appropriate.

71. Another preferred form of the invention has n=0 or 1, with one of A, B, D or E as nitrogen, the remaining three being carbon, one of Y & Z being oxygen, X=NH, Ar a benzene ring, optionally substituted, and $R^5$–$R^8$ hydrogen or a lone pair of electrons where appropriate.

Most Preferred Forms of the Invention

1. A most preferred form of the invention ms one where A–E, Y and Z are all carbon, n=0, X=NH, Ar is phenyl, $R^2$ is meta-bromo, m=1, and $R^3$–$R^8$ are all hydrogen.

2. A most preferred form of the invention is one where A–E, Y and Z are all carbon, n=1, X=NH, Ar is phenyl, $R^1$ is [R]—$CH_3$ and $R^2$–$R^8$ are all hydrogen.

3. A most preferred form of the invention is one where A and B are carbon, D and E taken together are nitrogen, Y and Z are carbon, n=0, X=NH, Ar is phenyl, $R^2$ is meta-bromo, m=1, and $R^4$–$R^8$ are all hydrogen.

4. A most preferred form of the invention is one where A and B taken together are sulfur, E is nitrogen, D, Y and Z are carbon, n=0, X=NH, Ar is phenyl, $R^2$ is meta-bromo, m=1, and $R^4$ and $R^6$–$R^8$ are all hydrogen.

5. A most preferred form of the invention is one where A and B taken together are oxygen, E is nitrogen, D, Y and Z are carbon, n=0, X=NH, Ar is phenyl, $R^2$ is meta-bromo, m=1, and $R^4$ and $R^6$–$R^8$ are all hydrogen.

6. A most preferred form of the invention is one where A and B taken together are nitrogen, E is nitrogen, D, Y and Z are carbon, n=0, X=NH, Ar is phenyl, $R^2$ is meta-bromo, m=1, and $R^4$ and $R^6$–$R^8$ are all hydrogen.

7. A most preferred form of the invention is one where A and B taken together are nitrogen, D and E taken seperately are nitrogen, Y and Z are carbon, n=0, X=NH, Ar is phenyl, $R^2$ is meta-bromo, m=1, and $R^6$–$R^8$ are all hydrogen.

8. A most preferred form of the invention is one where A and B taken together are nitrogen, E is nitrogen, Y and Z are carbon, n=0, X=NH, Ar is phenyl, $R^2$ is meta-bromo, m=1, and $R^4$, $R^7$ and $R^8$ are hydrogen and $R^6$ is methyl.

9. A most preferred form of the invention is one where A and B taken together are nitrogen, E is nitrogen, Y and Z are carbon, n=0, X=NH, Ar is phenyl, $R^2$ is meta-bromo, m=1, and $R^4$, $R^7$ and $R^8$ are hydrogen and $R^5$ is methyl.

10. A most preferred form of the invention is one where A and E are nitrogen, B, D, Y and Z are all carbon, n=0, X=NH, Ar is phenyl, $R^2$ is meta-bromo, m=1, and $R^3$–$R^8$ are all hydrogen.

11. A most preferred form of the invention is one where A and B taken together are nitrogen, E is nitrogen, Z is ethylidene, and Y a C—C bond, n=0, X =NH, Ar is phenyl, $R^2$ is meta-bromo, m=1, and $R^4$ and $R^6$–$R^8$ are all hydrogen.

12. A most preferred form of the invention is one where A–E, are all carbon, Z is sulfur, and Y a C—C bond, n=0, X=NH, Ar is phenyl, $R^2$ is meta-bromo, m=1, and $R^3$–$R^6$ are all hydrogen.

13. A most preferred form of the invention is one where A–E, are all carbon, Z is sulfur, and Y a C—C bond, n=0, X=NH, Ar is phenyl, $R^2$ is meta-bromo, m=1, $R^5$ is nitro $R^3$, $R^4$ and $R^6$ are all hydrogen.

14. A most preferred form of the invention is one where A–E, are all carbon, Z is sulfur, and Y a C—C bond, n=0, X=NH, Ar is phenyl, $R^2$ is meta-bromo, m=1, $R^5$ is amino $R^3$, $R^4$ and $R^6$ are all hydrogen.

15. A most preferred form of the invention is one where A–E, are all carbon, Z is sulfur, and Y a C—C bond, n=0, X=NH, Ar is phenyl, $R^2$ is meta-bromo, m=1, $R^6$ is methoxy and $R^3$–$R^5$ are all hydrogen.

16. A most preferred form of the invention is one where A is nitrogen, D and E taken together, and Z are sulfur and Y a C—C bond, n=0, X=NH, Ar is phenyl, $R^2$ is meta-bromo, m=1, and $R^3$ is hydrogen.

17. A most preferred form of the invention is one where A–E, are all carbon, Z is nitrogen, and Y a C—C bond, n=0, X=NH, Ar is phenyl, $R^2$ is meta-bromo, m=1, and $R^3$–$R^6$ and $R^8$ are all hydrogen.

18. A most preferred form of the invention is one where A–E, are all carbon, Y is nitrogen, and Z a C—C bond, n=0, X=NH, Ar is phenyl, $R^2$ is meta-bromo, m=1, and $R^3$–$R^6$ and $R^8$ are all hydrogen.

The compounds of the present invention are prepared according to a number of alternative reaction sequences.

It is to be appreciated that in the tricyclic structure of Formula I, the ring having A–E is aromatic. By "aromatic"

is meant that all members of the ring share electrons and there is a resonance among the members of the ring.

Preparative Routes to Compounds of the Invention

Scheme 1 for Preferred Group 1

Condensation of commercially available 3-amino-2-naphthoic acid with formamide gives the benzoquinazoline nucleus. (DMF is dimethyl formamide). Conversion of the carbonyl to halide is followed by displacement with the appropriate amine side chain.

Representative examples of compounds that can be made by this route are given in the table below.

Scheme 2 for Preferred Group 4 [3,2-g]Isomer

Nitration of methyl 5-methyl-2-nitrobenzoate, and isomer separation gives the 2,4-dinitrobenzoate ester. This is converted to the corresponding benzamide with methanolic ammonia, and both the amide nitrogen and the benzylic methyl are condensed with DMF di-t-butoxy acetal. On Raney Nickel reduction of both nitro groups to amines both the pyrrole and pyrimidone rings spontaneously cyclize to give the desired pyrrolo[3,2-g]quinazolone. Conversion on to the chloride with POCl$_3$ is followed by displacement of the chlorine with the desired amine.

Scheme 3—Route for Preferred Group 5 [4,5-g]Isomer

For the [4,5-g]isomer 7-chloroquinazol-4-one is nitrated at the 6-position by methods familiar to one skilled in the art. The activated 7-halide is then displaced by methoxide, the methyl ether is cleaved, the nitro group is reduced to amino, and the oxazole ring is cyclized on with formic acid. Phosphorus pentasulfide followed by methyl iodide activates the 4-position, and the synthesis is completed by displacement of the 4-methylthio group by an appropriate amine.

Scheme 4—Route for Preferred Group 5 [5,4-g]Isomer

For the [5,4-g]isomer the chlorine atom of the known 5-chloro-2,4-dinitrobenzamide is displaced with KOH, and the two nitro groups are then catalytically reduced to the diaminohydroxybenzamide. Treatment of this with excess orthoformate cyclizes both the oxazole and pyrimidone rings simultaneously, to give the desired tricyclic nucleus. Activation of the 4-oxo group with POCl$_3$ or other suitable chlorinating agent followed by displacement with the appropriate amine gives the desired compounds.

Scheme 5—Route for Preferred Group 6 [4,5-g]Isomer

For the [4,5-g]isomer 7-chloroquinazol-4-one is nitrated at the 6-position by methods familiar to one skilled in the art. The activated 7-halide is then displaced by methiolate ion, and the resultant thiomethyl ether is cleaved under the reaction conditions to give the corresponding thiol. The nitro group is reduced by a noncatalytic method, such as treatment with hydrosulfide ion or Zn/AcOH, and the thiazole ring is cyclized on with orthoformate. Phosphorus pentasulfide followed by methyl iodide activates the 4-position, and the synthesis is completed by displacement of the 4-methylthio group by an appropriate amine.

Scheme 6—Route for Preferred Group 6 [5,4-g]Isomer

For the [5,4-g]isomer the chlorine atom of the known 5-chloro-2,4-dinitrobenzamide is displaced with NaSH, and the 4-nitro group is concomitantly reduced to give an aminonitrobenzamide disulfide.

Treatment of this with borohydride, and then formic acid cyclizes the thiazole ring, to give the benzothiazole derivative. Reduction of the second nitro group followed by orthoformate cyclization gives the desired tricyclic pyrimidone. Activation of the 4-oxo group with POCl$_3$ or other suitable chlorinating agent followed by displacement with the appropriate amine gives the desired compounds.

Scheme 7—Route for Group 7

Nitration of 7-chloroquinazol-4-one at the 6-position by methods familiar to one skilled in the art is followed by displacement of the 7-chloro compound with ammonia. If a 3,N-alkyl substituent is required, an appropriate primary amine can be used instead of ammonia. Reduction with Pearlman's catalyst gives 6,7-diaminoquinazolone which on treatment with formic acid cyclizes to the imidazoloquinazolone. Phosphorus pentasulfide followed by methyl iodide activates the 4-position, and the synthesis is completed by displacement of the 4-methylthio group by an appropriate amine.

Scheme 8—Route to Preferred Group 10 [4,3-g]Isomers 2,4-Dimethylaniline is diazotized, and cyclized to a benzopyrazole. Nitration of this, followed by chromic acid oxidation and RaNi reduction of the nitro group gives the desired anthranilic acid derivative. This is cyclized to the pyrimidone with formamidine, and activated and displaced at the 4-position in the usual fashion.

Scheme 9—Route to Preferred Group 10 [3,4-g]Isomers 2,5-Dimethylacetanilide is nitrated, and the acetate group is saponified off. Diazotization leads to the desired benzopyrazole, which in turn is oxidized to the corresponding benzoic acid derivative. Catalytic reduction of the nitro group with Pd/C is followed by formamidine acetate ring cyclization. The pyrimidone is activated to displacement in one of the usual fashions, and a suitable amine is then introduced at the 4-position to give the desired compound.

Scheme 10—Route to Preferred Group 11 [4,5-g]Isomers 6,7-Diaminoquinazoline is prepared as described above in Scheme 7. This compound can be cyclized to the triazoloquinazolone via a diazotization, and then the carbonyl is activated via phosphorus pentasulfide and methyl iodide, as described previously and displaced with an appropriate amine to give the desired product.

Scheme 11—Route to Preferred Group 13 A & E Nitrogen 6,7-Diaminoquinazoline is prepared as described above. This compound can be cyclized to a pyrazinoquinazolone by treatment with 2,5-dihydroxy-1,4-dioxane, and then the carbonyl is activated via phosphorus pentasulfide and methyl iodide, as described previously and displaced with an appropriate amine to give the desired product.

Scheme 12—Route to Preferred Group 13 B & E Nitrogen

Reaction of 1,3-diaminobenzene with chloral and hydroxylamine, followed by cyclization with conc. sulfuric acid gives the bis-isatin type tricycle. Oxidation with hydrogen peroxide gives the symmetric diaminodiacid. This is doubly cyclized with formamidine, and converted to the corresponding dichloride with POCl$_3$ or equivalent. Monodisplacement with the desired amine, can be followed by displacement of the remaining chloride hydrogenolytically or by a suitable nucleophile to put in $R^5$.

Scheme 13—Route to Preferred Group 33 [4,5-f]Isomer

Nitration of 6-acetamidoquinazol-4-one gives the 5-nitro derivative. Hydrolysis of the amide with dilute HCl, followed by reduction with Pearlman's catalyst gives the 5,6-diaminoquinazolone. Fusion of the imidazole ring by a formic acid gives the parent ring skeleton, and then the carbonyl is activated via phosphorus pentasulfide and methyl iodide, as described previously and displaced with an appropriate amine to give the desired product.

Scheme 14—Route to Preferred Group 33 [4,5-h] Isomer

Nitration of 7-chloroquinazol-4-one by means obvious to one skilled in the art gives the 8-nitro derivative as a minor product. This is purified and the chlorine is displaced by ammonia under high temperature and pressure to give the 5-amino compound which is then reduced by Pearlman's catalyst (Pd hydroxide on carbon) to the 7,8-diaminoquinazolone.

Fusion of the imidazole ring by a formic acid derivative gives the parent ring skeleton, and then the carbonyl is activated via phosphorus pentasulfide and methyl iodide, as described previously and displaced with an appropriate amine to give the desired product.

Scheme 15—Route to Preferred Group 39 [3,2-d] Isomer

2-Fluorobenzonitrile or a suitably substituted derivative of it is treated with ethyl thioglycollate and a base in a dipolar aprotic solvent to give an ethyl 3-aminobenzothiophene-2-carboxylate derivative. This is cyclized to the desired benzothienopyrimidone with formamide, and the carbonyl is replaced by chlorine using standard techniques, and the chloride is displaced by an appropriate amine to give the desired compounds, or precursors that can readily be converted into them.

Scheme 16—Route to Preferred Group 39 [3,2-d] Isomer

In a variant of the route described in Scheme 15, lithiation of a suitably substituted fluorobenzene ortho to the fluorine atom is followed by carbonylation. The aldehyde is converted onto a suitable 2-fluorobenzonitrile derivative by oxime formation and dehydration. Alternatively the initial anion can be carboxylated and the resulting acid can be converted via the amide to the desired nitrile. This is then put through the sequence described in Scheme 15, to prepare derivatives which could not be obtained by substitution on 2-fluorobenzonitrile.

Scheme 17—Route to Preferred Group 39 [2,3-d] Isomer

Commercially available 4,6-dichloropyrimidine can be monodisplaced with 2-bromobenzenethiolate to give a diarylsulfide. This compound can be metalated at the 5-position of the pyrimidine ring with LDA, and quenched with Me$_3$SnCl, to form a halostannane. This halostannane is intramolecularly Stille coupled to give the desired 4-chlorobenzothieno[2,3-d]pyrimidine, from which chlorine can be displaced to give the desired product.

Scheme 18—Route to Preferred Group 41 [3',2':2,3] [4,5-d] Isomer

Halogen-metal exchange on 3-bromothiophene in ether at low temperature, followed by treatment with sulfur and then methyl bromoacetate gives methyl (thien-3-ylthio)acetate. Vilsmeier formylation using N-methylformanilide introduces a 2-formyl group on the thienyl ring, without inducing aldol cyclization. Reaction of the aldehyde to the oxime, followed by mesyl chloride/NEt$_3$ dehydration gives the corresponding nitrile, which cyclizes to methyl 3-aminothieno[3,2-b]thiophene-2-carboxylate on heating to 100° C. in DMSO with NEt$_3$. Pyrimidone fusion is carried out with formamide or an equivalent thereof, and the 4-keto substituent is activated and displaced in the usual manner to give the desired products.

Scheme 19—Route to Preferred Group 41 [2',3':2,3] [5,4-d] Isomer

Metalation of 3-bromothiophene with LDA occurs at the 2-position. Quenching of this anion with 1 equivalent of sulfur, followed by one equivalent of 4,6-dichloropyrimidine gives the thienopyrimidosulfide. Selective metalation with LDA at the 5-position of the pyrimidine ring, followed by stannylation gives a precursor for Stille coupling. After the coupling the 4-chlorine is displace with the appropriate amine to give the desired product.

Scheme 20—Route to Preferred Group 44 [4',5':2,3] [4,5-d] Isomer

Reaction of thiazolidin-2,4-dione with POCl$_3$ and DMF gives 2,4-dichlorothiazole-5-carbaldehyde. Protection of the aldehyde as an acetal is followed by selective removal of the 2-chlorine by halogen-metal exchange and hydrolysis. The aldehyde is oxidized up to the corresponding nitrile by oxime formation and dehydration, and 4-chloro-5-cyanothiazole on treatment with fresh 2-mercaptoacetamide in basic conditions gives 6-aminothieno[2,3-d]thiazole-5-carboxamide. This can be cyclized to the tricycle with ethyl orthoformate, and the carbonyl replaced by POCl$_3$ in the usual manner, and the chloride is then displaced by a suitable amine to give the desired product.

Scheme 21—Route to Preferred Group 45 [4',5':2,3] [4,5-d] Isomer

1,N-Benzyl-4,5-dibromoimidazole is lithiated with butyl lithium and formylated with DMF. Reaction of the bromoaldehyde with ethyl thioglycollate and base in DMSO leads to the desired aminothienoimidazole. This in turn is annulated again with formamide or an equivalent thereof, and the tricyclic pyrimidone is chlorinated at the 4-position and displaced with a suitable amine to give the desired product.

Scheme 22—Route to Preferred Group 49 [2',3';2,3] [4,5-d] Isomer

Reaction of 2-chloronicotinonitrile with methyl thioglycollate gives methyl 3-aminopyrido[2,3-d]thiophene-2-carboxylate. Fusion of the pyrimidone ring with formamide gives the corresponding pyrrido thienopyrimidone, which can then be chlorinated on the carbonyl and displaced with appropriate amines in the usual fashion to yield the desired compounds.

Scheme 23—Route to Preferred Group 50 [3,2-d] Isomer

A suitably substituted anthranilonitrile derivative is N-alkylated with ethyl bromoacetate, and the pyrrole ring is closed by treating the product of that reaction with KOBu$^t$, to give ethyl 3-aminoindole-2-carboxylate. The pyrimidone ring is fused onto this with formamide, and the carbonyl converted to chloride with POCl$_3$. Displacement of the chlorine with a suitable amine gives the desired compound.

Scheme 24—Route to Preferred Group 50 [2,3-d] Isomer

The fluoride of 2-fluoronitrobenzene is displaced by the anion derived from methyl cyanoacetate and KOBu$^t$. Mild reduction of the nitro group to amino is accompanied by spontaneous closure of the pyrrole ring to give ethyl 2-aminoindole-3-carboxylate. The pyrimidone ring is fused onto this with formamide, and the carbonyl converted to chloride with POCl$_3$. Displacement of the chlorine with a suitable amine gives the desired compound.

Scheme 25—Route to Preferred Group 61 [3,2-d] Isomer

O-Alkylation of 2-cyanophenol with methylbromoacetate, followed by treatment with a strong base gives ethyl 3-aminobenzofuran-2-carboxylate. The pyrimidone ring is fused onto this with formamide, and the carbonyl converted to chloride with Vilsmeier reagent. Displacement of the chlorine with a suitable amine gives the desired compound.

Biology

These compounds are potent and selective inhibitors of the human EGF receptor tyrosine kinase, and other members of the EGF receptor family, including the ERB-B2, ERB-B3 and ERB-B4 receptor kinases, and are useful for the treatment of proliferative diseases in mammals. These inhibitors prevent mitogenesis in cells where mitogenesis is driven by one or more of this family of receptor kinases. This can include normal cells, where it is desired to prevent mitogenesis, as exemplified by the cells transformed by overexpression or mutation of this kinase family as exemplified by poor prognosis breast cancer where overexpression of EGFR, ERB-B2 and ERB-B3 or mutation of ERB-B2 to the oncoprotein NEU is a major factor in cellular transformation. As the preferred compounds are not highly cytotoxic and do not show potent growth inhibitory properties, because of their high specificity toward inhibition of the EGFR kinase family, they should have a much cleaner toxicity profile than most anti-cancer and anti-proliferative drugs. Their very different mode of action to current anti-cancer drugs should allow for their use in multiple drug therapies, where synergism with available agents is anticipated.

Compounds of the invention have been shown to be very potent, reversible inhibitors of the EGF receptor tyrosine kinase, by binding with high affinity at the adenosine triphosphate (ATP) binding site of the kinase. These compounds exhibit potent $IC_{50}$s, varying from 10 micromolar to 50 picomolar, for the tyrosine kinase activity of the enzyme, based on an assay examining phosphorylation of a peptide derived from the phosphorylation site of the protein PLCgamma1, a known EGFR phosphorylation substrate. This data is shown in Table 1.

BIOLOGICAL DATA

Materials and Methods

Purification of Epidermal Growth Factor Receptor Tyrosine Kinase—Human EGF receptor tyrosine kinase was isolated from A431 human epidermoid carcinoma cells which overexpress EGF receptor by the following methods. Cells were grown in roller bottles in 50% Delbuco's Modified Eagle and 50% HAM F-12 nutrient media (Gibco) containing 10% fetal calf serum. Approximately $10^9$ cells were lysed in two volumes of buffer containing 20 mM 2-(4N-[2-hydroxyethyl]piperazin-1-yl)ethanesulfonic acid (hepes), pH 7.4, 5 mM ethylene glycol bis(2-aminoethyl ether) N,N,N',N'-tetraacetic acid, 1% Triton X-100, 10% glycerol, 0.1 mM sodium orthovanadate, 5 mM sodium fluoride, 4 mM pyrophosphate, 4 mM benzamide, 1 mM dithiothreitol, 80 µg/mL aprotinin, 40 µg/mL leupeptin and 1 mM phenylmethylsulfonyl fluoride. After centrifugation at 25,000× g for 10 minutes, the supernatant was equilibrated for 2 h at 4° C. with 10 mL of wheat germ agglutinin sepharose that was previously equilibrated with 50 mM Hepes, 10% glycerol, 0.1% Triton X-100 and 150 mM NaCl, pH 7.5, (equilibration buffer). Contaminating proteins were washed from the resin with 1M NaCl in equilibration buffer, and the enzyme was eluted with 0.5M N-acetyl-1-D-glucosamine in equilibration buffer, followed by 1 mM urea. The enzyme was eluted with 0.1 mg/ml EGF. The receptor appeared to be homogeneous as assessed by Coomassie blue stained polyacrylamide electrophoretic gels.

Determination of $IC_{50}$ values—enzyme assays for $IC_{50}$ determinations were performed in a total volume of 0.1 mL, containing 25 mM Hepes, pH 7.4, 5 mM $MgCl_2$, 2 mM $MnCl_2$, 50 µM sodium vanadate, 5–10 ng of EGF receptor tyrosine kinase, 200 µM of a substrate peptide, (Ac-Lys-His-Lys-Lys-Leu-Ala-Glu-Gly-Ser-Ala-Tyr$^{472}$-Glu-Glu-Val-$NH_2$, derived from the amino acid (Tyr$^{472}$ has been shown to be one of four tyrosines in PLC (phospholipaseC) -gamma 1 that are phosphorylated by the EGF receptor tyrosine kinase [Wahl, M. I.; Nishibe, S.; Kim, J. W.; Kim, H.; Rhee, S. G.; Carpenter, G., *J. Biol. Chem.*, (1990), 265, 3944–3948.], and peptides derived from the enzyme sequence surrounding this site are excellent substrates for the enzyme.), 10 µM ATP containing 1 µCi of [$^{32}$P]ATP and incubated for ten minutes at room temperature. The reaction was terminated by the addition of 2 mL of 75 mM phosphoric acid and passed through a 2.5 cm phosphocellulose filter disc to bind the peptide. The filter was washed five times with 75 mM phosphoric acid and placed in a vial along with 5 mL of scintillation fluid (Ready gel Beckman).

TABLE 1

EGF Receptor Tyrosine Kinase Inhibition

| Example # | $IC_{50}$ in EGFR |
|---|---|
| 1 | <100 pM |
| 2 | 21 nM |
| 3 | 760 pM |
| 4 | 44 nM |
| 5 | 75 pM |
| 6 | 6 pM |
| 7 | 4.1 nM |
| 8 | 30 pM |
| 9 | ~10 pM |
| 10 | 1.7 nM |
| 11 | 272 nM |
| 12 | 29 nM |
| 13 | 191 nM |
| 14 | 538 nM |
| 15 | 1.8 nM |
| 16 | 12.3 nM |
| 17 | 270 pM |
| 18 | 36% @ 10 nM |
| 19 | 40 nM |
| 20 | 1.3 µM |
| 21 | 732 nM |
| 22 | 2.11 µM |
| 23 | 460 nM |
| 24 | 419 nM |
| 25 | 72 nM |
| 26 | 132 nM |
| 27 | 264 nM |
| 28 | 31 nM |
| 29 | 732 nM |
| 30 | 4.1 µM |
| 31 | 220 nM |
| 32 | 160 nM |
| 33 |  |
| 34 | 740 nM |

Cells

Swiss 3T3 mouse fibroblasts, A431 human epidermoid carcinoma cells, and MCF-7 (Michigan Cancer Foundation human mammary carcinoma cells), SK-BR-3 (human mammary carcinoma cells), MDA-MB-231 and MDA-MB-468 (human mammary carcinoma cells) breast carcinomas were obtained from the American Type Culture Collection, Rockville, Md. and maintained as monolayers in dMEM (Dulbecco's modified eagle medium)/F12, 50:50 (Gibco/BRL) containing 10% fetal bovine serum. To obtain conditioned medium, MDA-MB-231 cells were grown to confluency in an 850 $cm^2$ roller bottle and the medium replaced with 50 ml of serum-free medium. After 3 days the conditioned medium was removed, frozen down in aliquots and used as a heregulin source to stimulate erbB-2, 3, 4.

Antibodies

Monoclonal antibodies raised to phosphotyrosine were obtained from Upstate Biotechnology, Inc., Lake Placid, N.Y. Anti-EGF receptor antibodies were obtained from Oncogene Science, Uniondale, N.Y.

Immunoprecipitation and Western Blot

Cells were grown to 100% confluency in 100 mm Petrie dishes (Corning). After the cells were treated for 5 minutes with either EGF (epidermal growth factor), PDGF, or bFGF (basic fibroblast growth factor) (20 ng/ml) or 1 ml of conditioned media from MDA-MB-231 cells, the media was removed and the monolayer scraped into 1 ml of ice cold lysis buffer (50 mM Hepes, pH 7.5, 150 mM NaCl, 10% glycerol, 1% triton X-100, 1 mM EDTA, 1 mM EGTA, 10 mM sodium pyrophosphate, 30 mM p-nitrophenyl phosphate, 1 mM orthovanadate, 50 mM sodium fluoride, 1 mM phenylmethylsulfonylfluoride, 10 µg/ml of aprotinin, and 10 µg/ml of leupeptin). The lysate was transferred to a microfuge tube (small centrifuge that holds 1-2 ml plastic centrifuge tubes), allowed to sit on ice 15 minutes and centrifuged 5 minutes at 10,000× g. The supernatant was transferred to a clean microfuge tube and 5 µg of antibody was added to designated samples. The tubes were rotated for 2 hours at 4° C. after which 25 µl of protein A sepharose was added and then rotation continued for at least 2 more hours. The protein A separose was washed 5 times with 50 mM Hepes, pH 7.5, 150 mM NaCl, 10% glycerol and 0.02% sodium azide. The precipitates were resuspended with 30 µl of Laemlli buffer (Laemmli, NATURE, Vol. 727, pp. 680–685, 1970), heated to 100° C. for 5 minutes and centrifuged to obtain the supernatant. Whole cell extracts were made by scraping cells grown in the wells of 6 well plates into 0.2 ml of boiling Laemmli buffer. The extract were transferred to a microfuge tube and heated to 100° C. for 5 minutes. The entire supernatant from the immunoprecipitation or 35 µl of the whole cell extract was loaded onto a polyacrylamide gel (4–20%) and electrophoresis carried out by the method of Laemlli (Laemmli, 1970). Proteins in the gel were electrophoretically transferred to nitrocellulose and the membrane was washed once in 10 mM Tris buffer, pH 7.2, 150 mM NaCl, 0.01% Azide (TNA) and blocked overnight in TNA containing 5% bovine serum albumin and 1% ovalbumin (blocking buffer). The membrane was blotted for 2 hours with the primary antibody (1 µg/ml in blocking buffer) and then washed 2 times sequentially in TNA, TNA containing 0.05% Tween-20 and 0.05% Nonidet P-40 (commercially available detergent) and TNA. The membranes were then incubated for 2 hours in blocking buffer containing 0.1 µCi/ml of [$^{125}$I] protein A and then washed again as above. After the blots were dry they were loaded into a film cassette and exposed to X-AR X-ray film for 1–7 days. Protein A is a bacterial protein that specifically bonds certain IgG subtypes and is useful in binding to and isolating antibody-antigen complexes.

Growth Inhibition Assay

Cells ($2 \times 10^4$) were seeded in 24-well plates (1.7×1.6 cm, flat bottom) in two mls of medium with or without various concentrations of drug. Plates were incubated for 3 days at 37° in a humidified atmosphere containing 5% $CO_2$ in air. Cell growth was determined by cell count with a Coulter Model AM electronic cell counter (Coulter Electronics, Inc., Hialeah, Fla.).

INHIBITION OF EGF-INDUCED AUTOPHOSPHORYLATION IN A431 EPIDERMOID CARCINOMA CELLS AND CONDITIONED MEDIA-INDUCED AUTOPHOSPHORYLATION IN SK-BR-3 BREAST TUMOR CELLS BY COMPOUNDS OF THE CURRENT INVENTION

| Example # | EGFR IC$_{50}$ nM | A431 IC$_{50}$ nM | SKBR-3 IC$_{50}$ nM |
|---|---|---|---|
| 1 | <0.1 | 17 | ND |
| 6 | 0.008 | 46 | 55 |
| 8 | 0.03 | 26 | 10 |
| 10 | 1.7 | 31 | ~700 |
| 15 | 1.8 | 170 | ND |
| 17 | 0.27 | 86 | 23 |
| 19 | 40 | ND | ~1500 |
| 25 | 72 | 93 | 1000 |
| 28 | 31 | 630 | 10 |
| 29 | 732 | 109 | 1100 |

The gels shown in the drawings, developed as detailed in the experimental section, demonstrate the efficacy of compounds of the current invention at blocking certain EGF-stimulated mitogenic signalling events in whole cells. The numbers to the left of gels indicate the positions of molecular weight standards in kiloDaltons. The lane labelled control shows the degree of expression of the growth-related signal in the absence of EGF stimulation, whereas the lane labelled EGF (or PDGF or b-FGF) shows the magnitude of the growth factor-stimulated signal. The other lanes show the effect of the stated quantities of the named drug on the growth factor-stimulated activity being measured, demonstrating that the compounds of the present invention have potent effects in whole cells, consistent with their ability to inhibit the tyrosine kinase activity of the EGF receptor.

See also the results as shown in FIGS. 1–8.

ANTIPROLIFERATIVE PROPERTIES OF TYROSINE KINASE INHIBITORS IC$_{50}$ (nM)

|  | Example 6 | Example 17 |
|---|---|---|
| B104-1-1 | 3200 | 2900 |
| SK-BR-3 | 200 | 1800 |
| MDA-468 | 20000 | 1800 |

B104-1-1-NIH-3T3 mouse fibroblasts transfected by the neu oncogene: Stern et al., SCIENCE, 234, pp. 321–324 (1987);

SK-BR-3-Human breast carcinoma overexpressing erbB-2 and erbB-3;

MDA-468-Human breast carcinoma overexpressing the EGF receptor.

Soft Agar Clonogenic Assays

Figure 9:
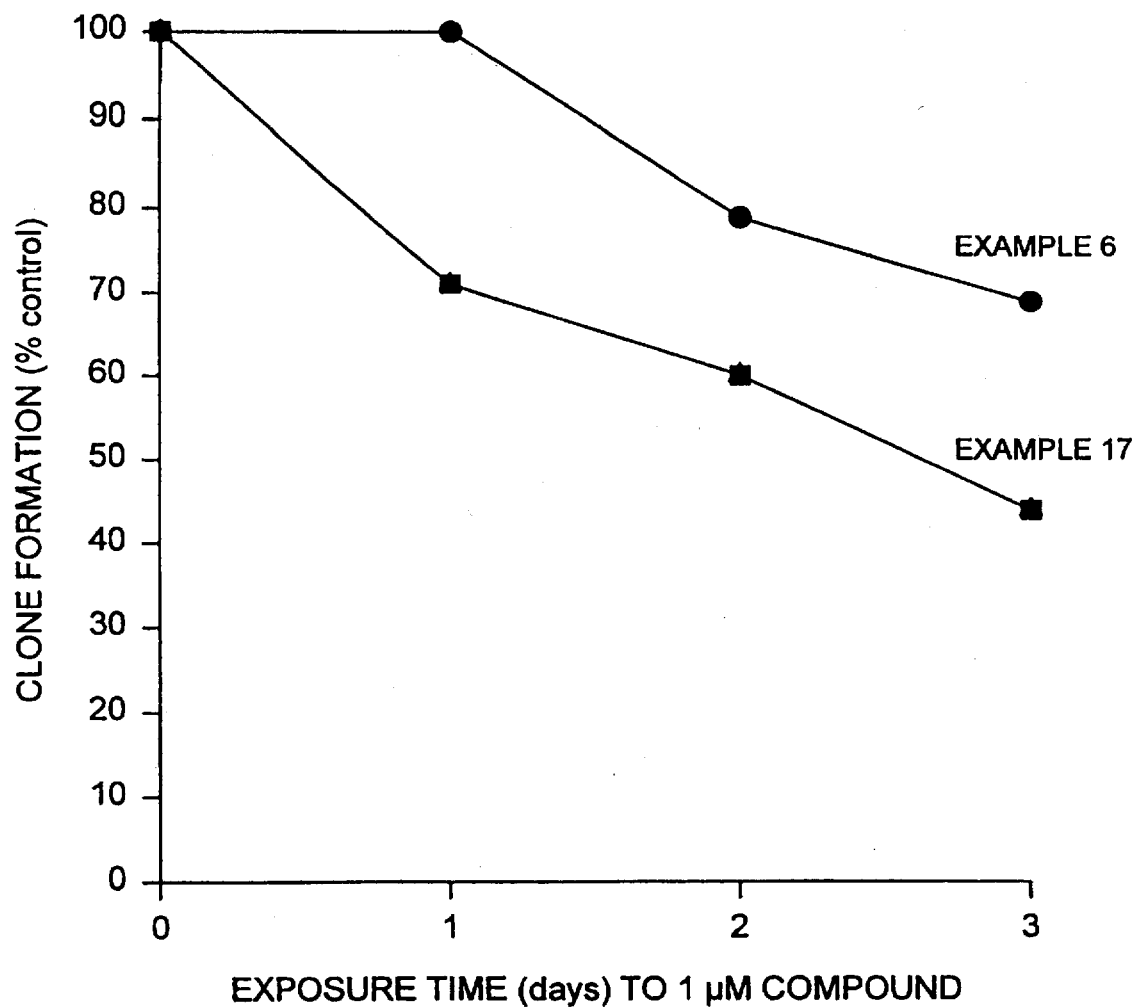
FIG. 9 is an effect of Examples 6 and 17 on soft agar clone formation of MDA-MB-468 human breast carcinoma.

Cell monolayers were exposed to the appropriate compound for 1–3 days and were then washed free of drug with warmed serum-free media. The cells were trypsinised and 10,000/mL were seeded into DMEM/F12 media containing 10% fetal calf serum and 0.4% agarose, but no drug. One ml of this solution was placed over a bottom layer of the same medium containing 0.8% agarose in a 35 mm Petri dish, and was incubated at 37° C. in a humidified atmosphere containing 5% carbon dioxide in air. After 3 weeks colonies were counted using an image analyzer for quantification. See FIG. 9.

It is to be appreciated that the compounds described herein can be used in combination with other components to enhance their activity. Such additional components are antineoplastic materials as, doxorubicin, taxol, cis platin, and the like.

It has been found that the compounds described herein may inhibit both the erb-B2 and erb-B4 receptors and therefore have significantly increased clinical activity advantageously in combination with the aforementioned anti-neoplastic agents.

See J. Basalga et al., Antitumor Effects of Doxorubicin in Combination With Anti-Epidermal Growth Factor Receptor Monoclonal Antibodies. JNCI, 1993, 85 1327, and Z. Fan et al., Antitumor Effect of Anti-Epidermal Growth Factor Receptor Monoclonal Antibodies Plus Cis Diamminedichloroplatinum on Well Established A431 Cell Xenografts. Cancer Res. 1993, 53, 4637.

Chemical Experimental

Listed below are preferred embodiments wherein all temperatures are in degrees Centigrade and all parts are parts by weight unless otherwise indicated.

EXAMPLE 1

4-(3-bromoanilino)benzo[g]quinazoline hydrochloride

3H-Benzo[g]quinazol-4-one. 3-Amino-2-naphthoic acid (3.74 g, 20 mmol) in stirred formamide is heated under N2 to 135° C. for 30 min, and to 175° C. for 2 h. The reaction mixture is poured onto vigorously stirred dilute NaOH solution (0.2M, 50 mL), containing ice, and the solid is collected by vacuum filtration, rinsed with water (2×25 mL), and dried in a vacuum oven at 60° C. to give benzo[g]-3H-quinazol-4-one (3.49 g, 89%) as a pale khaki solid. $^1$H NMR (DMSO) δ12.08 (1H, brs), 8.84 (1H, s), 8.24 (1H, s), 8.21 (1H, d, J=7 Hz), 8.10 (1H, d, J=7 Hz), 8.09 (1H, s), 7.62 ( 2H, apparent d of pentets, $J_d$=1.3 Hz, $J_p$=6.7 Hz).

4-Chlorobenzo[g]quinazoline. A suspension of benzo[g]-3H-quinazol-4-one (3.49 g, 18 mmol) in POCl$_3$ (40 mL) was refluxed under N$_2$ for 3 h. The volatiles were removed under reduced pressure, and the residue was partitioned between chloroform (200 mL) and dilute aqueous Na$_2$HPO$_4$ solution (1M, 50 mL). The organic phase was filtered through a silica gel plug (50 g), and the plug was then eluted with 20% EtOAc in CHCl$_3$ (500 mL). The combined eluents were concentrated under reduced pressure to give 4-chlorobenzo[g]quinazoline (1.20 g, 31%) as an orange-yellow solid. $^1$H NMR (DMSO) δ9.04 (1H, s), 8.91 (1H, s), 8.65 (1H, s), 8.20–8.09 (2H, m), 7.75–7.60 (2H, m).

4-(3-Bromoanilino)benzo[g]quinazoline hydrochloride. 4-Chlorobenzo[g]quinazoline (214 mg, 1.0 mmol), 3-bromoaniline (213 mg, 1.25 mmol) and NEt$_3$ (202 mg, 2.0 mmol) in stirred methoxyethanol (5 mL) were heated under N$_2$ at 95° C. for 6 h. The volatiles were removed under reduced pressure and the residual solid was triturated with MeOH. The solid was recrystallized at 0° C. from an EtOH/dilute hydrochloric acid mixture (1:4, 0.05M acid, 50 mL) after celite filtration to give 4-(3-bromoanilino)-benzo[g]quinazoline hydrochloride (71 mg, 18%) as a yellow-green solid. $^1$H NMR (DMSO) δ14.0 (1H brs), 9.65 (1H, s), 9.01 (1H, s), 8.47 (1H, s), 8.29 (1H, d, J=8.4 Hz), 8.24 (1H, d, J=8.4 Hz), 8.18 (1H, slbrs), 7.9–7.82 (2H, m), 7.78 (1H, t, J=7.5 Hz), 7.58 (1H, d, J=8 Hz), 7.51 (1H, t, J=8 Hz).

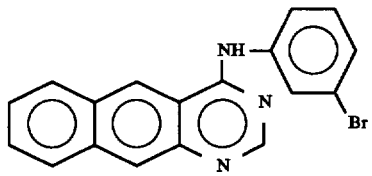

EXAMPLE 2

4-([R]-1-Phenylethylamino)benzo[g]quinazoline hydrochloride

4-Chlorobenzo[g]quinazoline (107 mg, 0.5 mmol), [R]-1-phenylethylamine (72 mg, 0.6 mmol) and NEt$_3$ (202 mg, 2.0 mmol) in stirred methoxyethanol (2 mL) are heated under N2 at 100° C. for 90 min. On cooling the reaction mixture is diluted with CHCl$_3$ (10 mL), and is shaken with dilute hydrochloric acid (0.2M, 15 mL). The heavy yellow precipitate is collected by Buchner filtration, rinsed with water (5 mL), and dried in vacuo at 60° C. to give 4-([R]-1-phenylethylamino)benzo[g]quinazoline hydrochloride hydrate (122 mg, 64%) as a yellow solid. $^1$H NMR (DMSO) δ14.75 (1H brs), 10.85 (1H, d, J=8.0 Hz), 9.61 (1H, s), 8.90 (1H, s), 8.36 (1H, s), 8.18 (1H, d, J=8.2 Hz), 7.82 (1H, t, J=7.6 Hz), 7.74 (1H, t, J=7.4 Hz), 7.56 (2H, d, J=7.5 KHz), 7.39 (2H, t, J=7.6 Hz), 7.30 (1H, t, J=7.4 Hz), 5.92 (1H, pentet, J=7.2 Hz), 1.76 (3H, d, J=7.2 Hz).

EXAMPLE 3

4-(3-Bromoanilino)pyrrolo[3,2-q]quinazoline

N-(5-(E,2-dimethylaminoethtenyl)-2,4-dinitrobenzoyl)-N'N'-dimethylformamidine. To a solution of 5-methyl-2,4-dinitrobenzamide (Blatt, A. H. J. Org. Chem 1960, 25, 2030.) (2.25 g, 10 mmol) in DMF (10 mL) is added t-butoxy-bis(dimethylamino)methane (6.2 mL, 30 mL). The reaction mixture is stirred at 55 ° C. for 2 h. The solvent is evaporated under reduced pressure and the residue is suspended in water. The precipitate is filtered and washed with water and ethyl ether to give N-(5-(E,2-dimethylaminoethtenyl)-2,4-dinitrobenzoyl)-N'N'-dimethylformamidine, 2.76 g (84%). $^1$H NMR (DMSO) δ 8.55 (1H, s), 8.47 (1H, s),8.04 (1H, d, J =13.0 Hz), 7.76 (1H, s), 5.95 (1H, d, J=13.0 Hz), 3.21 (3H, s), 3.00 (9H, m).

4-Oxo-3H-pyrroloquinazoline. A mixture of N-(5-(E,2-dimethylaminoethtenyl)-2,4-dinitrobenzoyl)-N'N'-dimethylformamidine (600 mg, 1.79 mmol) and Raney nickel (200 mg) in THF-MeOH (25 :25 mL) is hydrogenated in a rocking autoclave at 1500 psi at room temperature for 22 h. The catalyst is filtered off and the filtrate is concentrated in vacuo. The crude product is triturated in isopropanol and filtered. The solid is then washed with isopropanol and ethyl ether and dried in a vacuum oven at 40 20 C. to give 4-oxo-3H-pyrroloquinazoline (190 mg, 58%) as a bright red solid. $^1$H NMR (DMSO) δ11.8 (1H, brs), 11.6 (1H, brs,) 8.43 (1H, s), 7.95 (1H, s, J=3.1 Hz), 7.73 (1H, d, J=3.4 Hz), 7.55 (1H, s), 6.58 (1H, d, J=3.4 Hz).

4-(3-Bromoanilino)pyrrolo[3,2-g]quinazoline. 4-Oxo-3H-pyrroloquinazoline (100 mg, 0.54 mmol) in POCl$_3$ (5 mL) is refluxed under N$^2$ for 20 h. The resulting dark red solution is cooled to room temperature and extracted with ethyl acetate (2×20 mL). The organic layer is dried (Na$_2$SO$_4$) and concentrated to give a red solid (30 mg). Without further purification, this is suspended in 2-propanol (2 mL) containing m-bromoaniline ( 0.1 mL, 0.8 mmol). The reaction mixture is then refluxed for 1 h. The resulting bright yellow precipitate is filtered and washed with water and ether to yield 4-(3-bromoanilino)pyrrolo-[3,2-g]quinazoline (15 mg, 8 %). $^1$H NMR (DMSO) δ11.7 (1H, brs), 10.5 (1H, brs), 8.89 (1H, s), 8.73 (1H, brs), 8.16 (1H, s), 7.80 (3H, m), 7.35 (2H, s), 6.77 (1H, s).

EXAMPLE 4

4-(3-Bromoanilinolthiazolo[5,4-g]quinazoline 5,5'-Dithiobis(4-amino-2-nitrobenzamide). A solution of NaSH in aqueous MeOH (prepared according to Vogel, in "Elementary Practical Organic Chemistry, Part 1") is added dropwise with stirring to a solution of 5-chloro-2,4-dinitrobenzamide (5.00 g, 0.020 mmol) in a mixture of THF/MeOH (1:1, 200 mL) until no further reaction is observed (TLC analysis). The solution is then diluted with water and washed with CH$_2$Cl$_2$. The aqueous portion is acidified with concentrated HCl, extracted with EtOAc, and the extract is worked up to give an oily solid which is stirred vigorously with MeOH for 3 h. The resultant precipitate is removed by filtration to give 5,5'-dithiobis(4-amino-2-nitrobenzamide) (3.11g, 64%) as a tan powder. $^1$H NMR (DMSO) δ8.88 (1H, brs), 8.33 (1H, brs), 7.99 (1H, s), 7.94 (1H, s), 3.6–3.3 (2H, brs).

5-Nitrobenzothiazole-6-carboxamide. NaBH4 (0.50 g, 0.013 mmol) is added to a vigorously stirred suspension of 5,5'-dithiobis(4-amino-2-nitrobenzamide) (3.00 g, 7.13 mmol) in MeOH (60 mL). After 10 min the solution is acidified with concentrated HCl, extracted with EtOAc, and worked up rapidly to give 4-amino-5-mercapto-2-nitrobenzamide as an unstable solid which is used directly. The crude material is dissolved in formic acid (50 mL) heated under gentle reflux for 2 h, and then concentrated to dryness. The residue is triturated with MeOH/EtOAc (1:19), and unreacted disulfide (1.41 g) is recovered by filtration. The filtrate is concentrated and chromatographed on silica. Elution with EtOAc/petroleum ether (4:1) gives foreruns, while EtOAc gives 5-nitrobenzothiazole-6-carboxamide (1.31g, 41%) as a yellow powder. $^1$H NMR (DMSO) δ9.70 (1H, s), 8.71 (1H, s), 8.52 (1H, s), 8.25 (1H, brs), 7.78 (1H, brs).

Thiazolo[5,4-g]quinazol-4(3H)-one. A solution of 5-nitrobenzothiazole-6-carboxamide (0.30 g, 1.34 mmol) in MeOH/EtOAc (1:1, 25 mL) is hydrogenated over 5% Pd/C at 60 psi for 1 h to give 5-aminobenzothiazole-6-carboxamide. This is immediately dissolved in triethyl orthoformate (30 mL) and the mixture is heated under gentle reflux for 18 h. An equal volume of petroleum ether is added to the cooled solution, precipitating thiazolo[5,4-g]quinazol-4(3H)-one (0.17 g, 57%) as a tan powder. $^1$H NMR (DMSO) δ12.30 (1H, brs), 9.67 (1H, s). 9.00 (1H, s), 8.31 (1H, s), 8.14 (1H, s).

4-(3-Bromoanilinolthiazolo[5,4-g]quinazoline. A suspension of the thiazolo[5,4-g]quinazol-4(3H)-one (0.25 g, 1.23 mmol) in $POCl_3$ (20 mL) is heated under reflux for 3 h, then concentrated to dryness. The residue is partitioned between saturated aqueous $NaHCO_3$ and EtOAc, and the organic portion is worked up to give 4-chlorothiazolo[4,5-g]quinazoline (0.21 g, 0.95 mmol) as a yellow solid which is used directly. The crude product and 3-bromoaniline (0.21 mL, 1.90 mmol) are heated under reflux for 45 min in THF/propan-2-ol (1:1, 20 mL) containing a trace of concentrated HCl, and then concentrated to dryness. After trituration with EtOAc, the residue is partitioned between saturated aqueous $NaHCO_3$ and EtOAc and the organic portion is worked up to give 4-(3-bromoanilino)thiazolo[5,4-g]quinazoline (0.19 g, 49%),. $^1$H NMR (DMSO) δ10.05 (1H, brs), 9.74 (1H, s), 9.38 (1H, s), 8.71 (1H, s), 8.48 (1H, s), 8.31 (1H, brs), 7.96 (1H, d, J=7.7 Hz), 7.39 (1H, t, J=7.7 Hz,), 7.33 (1H,d, J=7.7 Hz).

EXAMPLE 5

4-(3-Bromoanilino)oxazolo[5,4-g]quinazoline 2 4-Dinitro-5-hydroxybenzamide. A solution of 5-chloro-2,4-dinitrobenzamide (5.50 g, 0.022 mmol) in p-dioxane/methanol (1:1, 120 mL) and 6N aqueous KOH (20 mL) is stirred at room temperature for 2 h. After acidification with concentrated HCl, the mixture is diluted with water and extracted into EtOAc. Workup gives 2,4-dinitro-5-hydroxybenzamide (4.91g, 98%) as yellow cubes. $^1$H NMR (DMSO) δ8.64 (1H, s), 8.16 (1H, brs), 7.81 (1H, brs), 7.13 (1H, s), 5.80 (1H, brs).

4-Oxo-3H-oxazolo[5,4-g]quinazoline. A solution of 2,4-dinitro-5-hydroxybenzamide (4.00 g, 0.018 mmol) in MeOH/EtOAc (1:1, 50 mL) is hydrogenated over 5% Pd/C at 60 psi for 3 h to give 2,4-diamino-5-hydroxybenzamide, which is used directly. Formic acid (50 mL) is added and the solution is heated under reflux for 48 h. then the volatiles are removed under reduced pressure. The residue is triturated with EtOAc to give crude 4-oxo-3H-oxazolo[5,4-g]quinazoline(3.27 g, 97%) as a tan powder which is used directly.

4-Chlorooxazolo[5,4-g]quinazoline. A suspension of 4-oxo-3H-oxazolo[5,4-g]quinazoline (0.98 g, 5.24 mmol) in $POCl_3$ (30 mL) is heated under reflux with vigorous stirring for 18 h, and then concentrated to dryness. The residue is partitioned between EtOAc and saturated aqueous $NaHCO_3$ and the organic portion is worked up to give 4-chlorooxazolo[5,4-g]quinazoline (0.24g, 22%) as a yellow solid which is used directly.

4-(3-Bromoanilino)oxazolo[5,4-g]quinazoline. A mixture of 4-chlorooxazolo[5,4-g]quinazoline (0.24 g, 1.16 mmol) and 3-bromoaniline (0.25 mL, 2.33 mmol) in a THF/propan-2-ol mixture (1:1, 40 mL) containing a trace of concentrated HCl is heated under reflux for 15 min, then concentration to dryness under reduced pressure. The residue is triturated with EtOAc, and then partitioned between saturated aqueous $NaHCO_3$ and EtOAc. Workup of the organic portion gives 4-(3-bromoanilino)oxazolo[5,4-g]quinazoline (0.18 g, 33%) as a yellow powder, mp (MeOH) 232 ° C. (dec.).

EXAMPLE 6

4-(3-Bromoanilino)imidazolo[4,5-g]quinazoline

A mixture of 4-methylthio-6H-imidazo[4,5-g]quinazoline (0.5 g, 1.6 mmol) [Leonard, N. J.; Morrice, A. G.; Sprecker, M. A.; J. Org. Chem., 1975, 40, 356–363], 3-bromoaniline (0.35 g, 2.0 mmol), and 3-bromoaniline hydrochloride (0.4 g, 1.9 mmol) in isopropanol (200 mL) is heated under reflux for 1 h to give a precipitate of 4-(3-bromoanilino)-6H-imidazo[4,5-g]quinazoline hydrochloride (0.63 g, 72%). $^1$H NMR (DMSO) δ9.93 (1H, brs), 9.01 (1H, s), 8.66 (2H, s), 8.39 (1H, s), 8.04 (2H, m), 7.39 (1H, t, J=7.9 Hz), 7.31 (1H, brd, J=8.0 Hz).

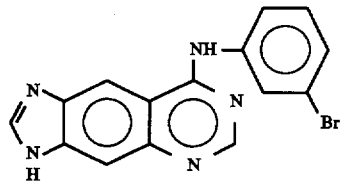

EXAMPLE 7

4-(3-Bromoanilino)triazolo[4,5-g]quinazoline hydrochloride

4-Oxo-3H-triazolo[4,5-g]quinazoline. A solution of 6,7-diamino-4-oxo-3H-quinazoline (91 g, 5.7 mmol) [Leonard, N. J.; Morrice, A. G.; Sprecker, M. A.; J. Org. Chem., 1975, 40, 356–363]in 0.1M HCl (250 mL) is cooled to below 10 ° C., and a solution of $NaNO_2$ (0.41 g, 6 mmol) in water (10 mL) is added over 2 min. After 15 min the solution is neutralized with 0.1M KOH solution to give a precipitate of 4-oxo-3H-triazolo[4,5-g]quinazoline (1.01 g, 94 %). $^1$H NMR (DMSO) δ12.22 (2H, m), 8.76 (1H, s), 8.12 (1H, s), 8.07 (1H, s).

4-Thiono-3H-triazolo[4,5-g]quinazoline. A mixture of 4-oxo-3H-triazolo[4,5-g]quinazoline (0.56 g, 3 mmol) and $P_2S_5$ (1.3 g, 6 mmol) in pyridine (20 mL) is heated under reflux for 2 h, and the solvent is removed under reduced pressure. The residue is treated with boiling water (30 mL) to give a yellow solid which is collected by filtration and dissolved in 0.1M KOH solution. After filtration to remove insolubles, the clear yellow solution is neutralized with dilute HCl to give 4-thiono-3H-triazolo[4,5-g]quinazoline (0.26 g, 43 %). 1H NMR (DMSO) δ9.20 (1H, s), 8.15 (1H, s), 8.14 (1H, s).

4-Methylthiotriazolo[4,5-g]quinazoline. A solution of 4-thiono-3H-triazolo[4,5-g]quinazoline (0.203 g, 1 mmol) and KOH (0.15 g, 2.7 mmol) in 50% MeOH-$H_2O$ (15 mL) is treated with MeI (65 μL, 1.0 mmol) and the mixture is stirred at room temperature overnight. The MeOH is removed under vacuum and the solution neutralized with dilute HCl to give crude 4-methylthiotriazolo[4,5-g]

quinazoline (0.12 g, 55%). $^1$H NMR (DMSO) δ8.96 (1H, s), 8.79, (1H, s), 8.40 (1H, s), 2.74 (3H, s).

4-(3-Bromoanilino)-triazolo[4,5-g]quinazoline hydrochloride. A mixture of 4-methylthiotriazolo[4,5-g]quinazoline (0.30 g, 1.38 mmol), 3-bromoaniline (2.1 mmol) and 3-bromoaniline hydrochloride (2.1 mmol) in isopropanol (400 mL) is heated under reflux for 6 h, and the solution is concentrated to give 4-(3-bromoanilino)-triazolo[4,5-g]quinazoline hydrochloride (0.33 g, 63 %). $^1$H NMR (DMSO) δ12.01 (1H, brs), 9.86 (1H, s), 9.02 (1H, s), 8.63 (1H, s), 8.39 (1H, s), 8.13 (1H, dd, J=1.9, 1.5 Hz), 7.85 (1H, ddd, J=7.7, 1.9, 1.5 Hz), 7.56 (1H, ddd, J=8.0, 1.7, 1.5 Hz), 7.41 (1H t, J=7.8 Hz).

EXAMPLE 8

4-(3-Bromoanilino)-8,N-methylimidazolo[4,5-g]quinazoline

8,N-Methyl-3H-imidazo[4,5-g]quinazolin-4-thione. A mixture of 8,N-methyl-3H-imidazo[4,5-g]quinazolin-4-one (2.32 g, 11.1 mmol) [Lee, C.-H.; Gilchrist, J. H.; Skibo, E. B.; *J. Org. Chem.*, 1986, 51, 4784–4792] and P$_2$S$_5$ (3.96 g, 17.8 mmol) in pyridine (25 mL) is heated under reflux for 16 h. The pyridine is removed under vacuum, and the residue is treated with boiling water (50 mL). The precipitate is collected, washed with water, and dissolved in 0.1M KOH. After filtration to remove insolubles, the clear yellow solution is acidified with AcOH to give 8,N-methyl-3H-imidazo[4,5-g]quinazoline-4-thione (2.12 g, 88 %). $^1$H NMR (DMSO) δ8.91 (1H, s), 8.53 (1H, s), 8.12 (1H, s), 7.91 (1H, s), 3.93 (3H, s).

8 N-Methyl-4-methylthioimidazo[4,5-g]quinazoline. MeI (0.61 ml, 9.5 mmol) is added to a solution of 8,N-methyl-3H-imidazo[4,5-g]quinazoline-4-thione (1.87 g, 8.65 mmol) and KOH (0.58 g, 10 mmol) in 100 ml 50 % MeOH-H$_2$O, and the resulting mixture is stirred at room temperature for 30 min. The precipitated product is filtered off, and dried, to give 8,N-methyl-4-methylthioimidazo[4,5-g]quinazoline (1.89 g, 82%). $^1$H NMR (DMSO) δ8.96 (1H, s), 8.64 (1H, s), 8.39 (1H, s), 8.16 (1H, s), 3.98 (3H, s), 2.74 (3H, s).

4-(3-Bromoanilino)8,N-methylimidazolo[4,5-g]quinazoline. A mixture of 8,N-methyl-4-methylthioimidazo[4,5-g]quinazoline (1.50 g, 6.5 mmol), 3-bromoaniline (1.7 g, 10 mmol), and 3-bromoaniline hydrochloride (2.1 g, 10 mmol) in isopropanol (400 mL) is heated under reflux for 4 h to give a precipitate of the product hydrochloride, which is treated with aqueous NH$_3$ to give 4-(3-bromoanilino)-8,N-methylimidazo[4,5-g]quinazoline (1.22 g, 52%). $^1$H NMR (DMSO) δ9.86 (1H, s), 9.02 (1H, s), 8.63 (1H, s), 8.54 (1H, s), 8.37 (1H, s), 8.01 (2H, m), 7.36 (1H, t, J=8.0 Hz), 7.28 (1H, brd), 3.96 (3H, s).

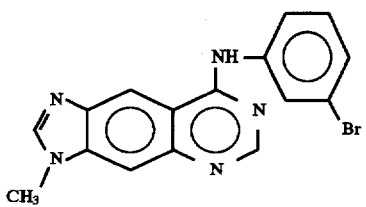

EXAMPLE 9

4-(3-Bromoanilino)-6,N-methylimidazolo[4,5-g]quinazoline 2,4-Dinitro-5-methylaminobenzamide. A solution of 5-chloro-2,4-dinitrobenzamide (6.14 g, 25 mmol) [Goldstein, H.; Stamm, R.; Helv. *Chim. Acta*, 1952, 35, 1330–1333] and 40% aqueous methylamine (20 mL) in ethanol (80 mL) is heated in a sealed pressure vessel at 100° C. for 2 h. After cooling, dilution with water gives 2,4-dinitro-5-methylaminobenzamide (5.89 g, 98%). $^1$H NMR (DMSO) δ8.88 (1H, q, J=4.9 Hz), 8.76 (1H, s), 8.07 (1H, brs), 7.77 (1H, brs), 6.98 (1H,s), 3.07 (3H, d, J=5.0 Hz)

6,N-methyl-3H-imidazo[4,5-g]quinazolin-4-one. A suspension of 2,4-dinitro-5-methylaminobenzamide (4.80 g, 20 mmol) in ethanol and formic acid (2.5 mL, 66 mmol) is hydrogenated over 5% Pd/C, and the solvent is removed under reduced pressure. The resulting crude salt is dissolved in formic acid (100 mL) and the mixture is heated under reflux for 2 h. The formic acid is removed under reduced pressure, and the residue is dissolved in the minimum volume of 0.1M HCl. After clarification with charcoal and filtration through celite, the aqueous solution is neutralized with dilute aqueous NH$_3$, and allowed to stand overnight, to give 6,N-methyl-3H-imidazo[4,5-g]quinazolin-4-one (2.99 g, 75%). $^1$H NMR (DMSO) δ11.91 (12H, brs), 8.50 (1H, s), 8.33 (1H, s), 8.00 (1H, s), 7.89 (1H, s), 3.95 (3H, s).

6,N-Methyl-3H-imidazo[4,5-g]quinazolin-4-thione. A mixture of 6,N-methyl-3H-imidazo[4,5-g]quinazolin-4-one (2.50 g, 12.5 mmol) and P$_2$S$_5$ (5.55 g, 25 mmol) in pyridine (30 mL) is heated under reflux for 16 h, and the pyridine is removed under reduced pressure. The residue is treated with boiling water (50 mL), and the resulting yellow precipitate is collected by filtration and dissolved in 0.1M KOH solution. After filtration to remove insolubles, the solution is neutralized with NH$_4$Cl to give 6,N-methyl-3H-imidazo[4,5-g]quinazolin-4-thione (1.58 g, 59%). $^1$H NMR (DMSO) δ13.65 (1H, brs), 8.76 (1H, s), 8.61 (1H, s), 8.11 (1H, s), 7.98 (1H, s), 3.99 (3H, s).

6,N-Methyl-4-methylthioimidazo[4,5-g]quinazoline. A solution of 6,N-methyl-3H-imidazo[4,5-g]quinazolin-4-thione (1.08 g, 5 mmol) and KOH (0.40 g, 7 mmol) in 50% aqueous MeOH (100 mL) is treated with MeI (0.33 mL, 5.3 mmol) and the resulting mixture is stirred at room temperature for 1 h. The methanol is then removed under reduced pressure, and the residual aqueous solution is kept at 5° C. overnight to give crystals of 6,N-methyl-4-methylthioimidazo[4,5-g]quinazoline (0.62 g, 54%). $^1$H NMR (DMSO) δ8.93 (1H, s), 8.67 (1H, s), 8.22 (1H, s), 8.21 (1H, s), 4.01 (3H, s), 2.74 (3H, s).

4-(3-Bromoanilino-6, N-methylimidazo[4,5-g]quinazoline hydrochloride. A mixture of 6,N-methyl-4-methylthioimidazo[4,5-g]quinazoline (0.3 g, 1.3 mmol), 3-bromoaniline (0.34 g, 1.95 mmol), and 3-bromoaniline hydrochloride (0.41 g, 1.95 mmol) in isopropanol (400 mL) is heated under reflux for 6 h. After cooling the precipitated solid is collected by filtration and recrystallized from EtOH to give 4-(3-bromoanilino)-6,N-methylimidazo[4,5-g]quinazoline hydrochloride (0.43 g, 85%). $^1$M NMR (DMSO) δ11.66 1H, brs), 9.43 (1H, s), 8.96 (1H, s), 8.80 (1H, s), 8.19 (1H, s), 8.16 (1H, brs), 7.89 (1H, brd, J=7.1 Hz), 7.54–7.43 (2H, m), 4.05 (3H, s).

Example 10

4-(3-Bromoanilino)pyrazino[2,3-g]quinazoline

7-Acetamido-6-nitro-3H-quinazolin-4-one. A solution of 7-amino-6-nitro-3H-quinazolin-4-one (5.90 g, 28.6 mmol) [Leonard, N. J.; Morrice, A. G.; Sprecker, M. A.; *J. Org. Chem.*, 1975, 40, 356–363] in a mixture of glacial acetic acid (300 mL) and acetic anhydride (100 mL) is heated under reflux for 6 h, and water (100 mL) is added. The solution is then concentrated to a small volume to give 7-acetamido-6-nitro-3H-quinazolin-4-one (5.37 g, 76%). ¹H NMR (DMSO) δ10.51 (1H, brs), 8.57 (1H, s), 8.24 (1H, s), 7.97 (1H, s), 2.15 (3H, s).

7-Acetamido-4-(3-bromoanilino)-6-nitroquinazoline. A solution of 7-acetamido-6-nitro- 3H-quinazolin-4-one (5.00 g, 20 mmol) in POCl₃ (250 mL) is heated under reflux for 2 h, the excess of POCl₃ is removed under vacuum, and the residue is dissolved in CH₂Cl₂ and washed with aqueous Na₂CO₃ solution. Workup gives the crude 4-chloro derivative, which is coupled directly with 3-bromoaniline in isopropanol as above, and the resulting hydrochloride is converted directly to the free base, by treatment with aqueous NH₃, to give 7-acetamido-4-(3-bromoanilino)-6-nitroquinazoline (3.60 g, 45%). ¹H NMR (DMSO) δ10.56 (1H, s), 10.29 (1H, s), 9.34 (1H, s), 8.70 (1H, s), 8.19 (1H, brs), 7.97 (1H, s), 7.88 (1H, d, J=6.0 Hz), 7.43–7.35 (2H, m), 2.13 (3H, s).

7-Amino-4-(3-bromoanilino)-6-nitroquinazoline. A solution of 7-acetamido-4-(3-bromoanilino)-6-nitroquinazoline (1.50 g, 3.73 mmol) and KOH (2 g) in MeOH (190 mL) and H₂O (10 mL) is heated under reflux for 30 min, and the solvent volume is reduced to give 7-amino-4-(3-bromoanilino)-6-nitroquinazoline (1.17 g, 87%). ¹H NMR (DMSO) δ10.17 (1H, brs), 9.43 (1H, s), 8.43 (1H, s), 8.15 (1H,m brs), 7.86 (1H, d, J=7.1 Hz), 7.42 (2H, brs), 7.40–7.31 (2H, m), 7.12 (1H, s).

4-(3-Bromoanilino)-6,7-diaminoquinazoline. Iron dust reduction of 7-amino-4-(3-bromoanilino)-6-nitroquinazoline (0.5 g, 1.4 mmol) in 65% aqueous EtOH containing sufficient aqueous HCl to ensure solubility gives 4-(3-bromoanilino)-6,7-diaminoquinazoline (0.30 g, 65%). ¹H NMR (DMSO) δ9.14 (1H, s), 8.27 (1H, s), 8.23 (1H, brs), 7.85 (1H, d, J =8.0 Hz), 7.31–7.14 (2H, m), 7.29 (1H, s), 6.79 (1H, s), 5.73 (2H, brs), 5.13 (2H, brs).

4-(3-Bromoanilino)pyrazino[2,3-g]quinazoline. A mixture of 4-(3-bromoanilino)-6,7-diaminoquinazoline (90 mg, 0.27 mmol) and 1,4-dioxane-2,3-diol (0.2 g, 1.6 mmol) [Venuti, M. C.; Synthesis, 1982, 61–63] in MeOH (20 mL) is stirred at room temperature overnight to give a precipitate of 4-(3-bromoanilino)pyrazino[2,3-g]quinazoline (80 mg, 83%). ¹H NMR (DMSO) δ10.45 (1H, brs), 9.52 (1H, s), 9.09 (1H, d, J=1.6 Hz), 9.06 (1H, d, J=1.6 Hz), 8.71 (1H, s), 8.44 (1H, s), 8.32 (1H, brs), 7.99 (1H, m), 7.45–7.34 (2H, m).

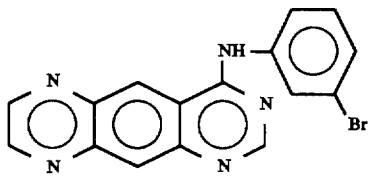

EXAMPLE 11

4-(3-Bromoanilino)imidazolo[4,5-h]quinazoline hydrochloride

6-Methylthioimidazo[4,5-h]quinazoline. A solution of 3H-imidazo[4,5-h]quinazoline-4-thione (0.41 g, 2 mmol) [Morrice, A. G.; Sprecker, M. A.; Leonard, N. J.; *J. Org. Chem.*, 1975, 40, 363–366] and KOH (0.15 g, 27 mmol) in 50% MeOH-H₂O (50 mL) is treated with MeI (0.13 mL) and the mixture is stirred at room temperature for 3 h to give a precipitate of 4-methylthioimidazo[4,5-h]quinazoline (0.35 g, 80%). ¹H NMR (DMSO) δ13.80 (1H, brs), 9.09 (1H, s), 8.49 (1H, s), 7.98 (1H, d, J=8.8 HzH), 7.85 (1H, d, J=8.8 Hz), 2.72 (3H, s).

4-(3-Bromoanilino)imidazolo[4,5-h]quinazoline. A mixture of 4-methylthioimidazo[4,5-h]quinazoline (0.216 g, 1 mmol), 3-bromoaniline (0.25 g, 1.5 mmol), and 3-bromoaniline hydrochloride (0.31 g, 1.5 mmol) in N-methylpyrrolidone (50 mL) is heated 120° C. for 2 h. The solvent is removed under vacuum and the residue is triturated with EtOH to give a solid which is recrystallized from MeOH to give 4-(3-bromoanilino)imidazo[4,5-h] quinazoline hydrochloride (0.23 g, 61%). ¹H NMR (DMSO) δ11.11 (1H, brs), 8.93 (2H, s), 8.66 (1H, d, J=9.0 Hz), 8.11 (1H, brs), 8.07 (1H, d, J=9.0 Hz), 7.83 (1N, brd, J=6.8 Hz), 7.50–7.40 (2H,m).

EXAMPLE 12

4-(3-Bromoanilino)imidazolo[4,5-f]quinazoline

4-Methylthioimidazo[4,5-f]quinazoline. A solution of 3H-imidazo[4,5-f]quinazoline-4-thione (1.01 g, 5 mmol) [Morrice, A. G.; Sprecker, M. A.; Leonard, N. J.; *J. Org. Chem.*, 1975, 40, 363–366] and KOH (0.36 g, 6.5 mmol) in 50% MeOH-H₂O (50 mL) is treated with MeI (0.34 mL) and the mixture is stirred overnight at room temperature. The MeOH is removed under vacuum to give a precipitate of 4-methylthioimidazo[4,5-f]quinazoline (0.61 g, 57%). ¹H NMR (DMSO) δ13.23 (1H, m), 9.05 (1H, s), 8.60 (1H, s), 8.24 (1H, d, J=8.7 Hz), 7.81 (1H, d, J=8.9 Hz), 2.71 (3H, S).

4-(3-bromoanilino)imidazo[4,5-f]quinazoline. A solution of 4-methylthioimidazo[4,5-f]quinazoline (0.43 g, 2 mmol), 3-bromoaniline (0.5 g, 3 mmol), and 3-bromoaniline hydrochloride (0.63 g, 3 mmol) is heated under reflux for 16 h. The precipitate of hydrochloride salt is converted directly to the free base with aqueous NH₃, and recrystallized from EtOH to give 4-(3-bromoanilino)imidazo[4,5-f]quinazoline (0.52 g, 77%). ¹H NMR (DMSO) δ11.53 (1H, brs), 8.79 (1H, s), 8.68 (1H, s), 8.53 (1H, dd, J=1.8, 1.9 Hz), 8.15 (1H, d, J=8.8 Hz), 7.81 (1H, brd, J=8.6 Hz), 7.71 (1H, d, J=8.9 Hz, 1H), 7.41 (1H, t, J=8.0 Hz), 7.32 (1H, brd, J=7.8 Hz).

EXAMPLE 13

4-Benzylaminobenzothieno[3,2-d]pyrimidine

4-Chlorobenzothieno[3,2-d]pyrimidine (111 mg, 0.5 mmol), (see following experimental) and benzylamine (114 mg, 1.0 mmol) (111 mg, 1.1 mmol) in stirred 2-propanol (2 mL) are heated at reflux under N₂ for 26 h. The mixture is allowed to cool, and the precipitate is collected by Buchner filtration, rinsed with 2-propanol and water and dried in an oven to give 4-benzylaminobenzothieno[3,2-d]pyrimidine (100 mg, 68%) as a white powder. ¹H NMR (DMSO) δ8.60 (1H, s), 8.51 (1H, t, J=5.9 Hz), 8.31 (1H, ddd, J=0.7, 1.4, 8.0 Hz), 8.17 (1H, ddd, J=0.7, 1.8, 8.1 Hz), 7.68 (1H, ddd, J=1.2, 7.0, 8.1 Hz), 7.59 (1H, ddd, J =1., 7.0, 8.1 Hz), 7.36 (2H, d, J=7.4 Hz), 7.33 (2H, t, J=7.3 Hz), 7.24 (1H, t, J=7.2 Hz), 4.79 (2H, d, J=6.0 Hz).

EXAMPLE 14

4-([R]-1-Phenylethylamino)benzothieno[3,2-d] pyrimidine

Ethyl 3-aminobenzothiophene-2-carboxylate. 2-Fluorobenzonitrile (0.61 g, 5 mmol), ethyl thioglycollate (0.60 g, 5 mmol) and NEt₃ (1.52 g, 15 mmol) are stirred in DMSO (5 mL) at 100° C. under N₂ for 3 h. The reaction mixture is poured onto ice-water (50 mL), and the solid is collected by suction filtration, rinsed with water, and air dried to give ethyl 3-aminobenzothiophene-2-carboxylate (0.78 g, 70%) as a grey-brown solid. $^1$H NMR (DMSO) δ8.14 (lH, d, J=7.7 Hz), 7.88 (1H, d, J=8.1 Hz), 7.50 (1H, dt, $J_d$=1.2 Hz, $J_f$=7.5 Hz), 7.39 (1H, dt, $J_d$=1.2 Hz, $J_f$=7.6 Hz), 7.17 (2H, brs), 4.26 (2H, q, J=7.1 Hz), 1.29 (3H, t, J=7.1 Hz).

Benzothieno[3,2-d]-3H-pyrimid-4-one: Ethyl 3-aminobenzothiophene-2-carboxylate (764 mg, 3.45 mmol) is heated in formamide (2 mL) under $N_2$ at 140° C. for 2 h, and at 180° C. for 20 h. The solution is allowed to cool to 25° C., and the slurry is diluted with EtOH (5 mL). The solid is collected by suction filtration, rinsed with EtOH (2×5 mL), and air dried to give benzothieno[3,2-d]-3H-pyrimid-4-one (0.55 g, 79%) as a highly crystalline dark brown solid. $^1$H NMR (DMSO) δ12.85 (1H, brs), 8.35 (1H,s), 8.16 (1H, d J=7.3 Hz), 7.67 (1H, dt, $J_d$=1.6 Hz, $J_f$=7.5 Hz), 7.59 (1H, dt, $J_d$=1.2 Hz, $J_f$=7.5 Hz,).

4-Chlorobenzothieno[3,2-d]pyrimidine. DMF (0.27 g, 3.5 mmol) is added dropwise to a solution of oxalyl chloride (0.44 g, 3.5 mmol) in 1,2-dichloroethane (10 mL), stirred under $N_2$ at 25° C. When the vigorous gas evolution ceases, benzothieno[3,2-d]-3H-pyrimid-4-one (337 mg, 1.53 mmol) is added and the reaction mixture is heated to reflux. After 20 min, the reaction mixture is allowed to cool, and is then quenched with saturated aqueous $NaHCO_3$ solution (20 mL). The phases are separated, and the aqueous phase is extracted with $CHCl_3$ (3×10 mL). The combined organic phases are washed with water (2×10 mL), saturated brine (10 mL), and dried ($Na_2SO_4$). The solvent is removed under reduced pressure to give 4-chlorobenzothieno[3,2-d]pyrimidine (249 mg, 74%) as a light brown solid. $^1$H NMR ($CDCl_3$) δ9.09 (1H, s), 8.53 (1H, dd, J=1.8, 7.6 Hz), 7.95 (1H, d, J=7.8 Hz), 7.73 (1H, dt, $J_d$=1.4 Hz, $J_f$=7.7 Hz), 7.62 (1H, dt, $J_d$=1.2 Hz, $J_f$=7.5 Hz).

4-([R]-1-Phenylethylamino)benzothieno[3,2-d]pyrimidine 4-Chlorobenzothieno[3,2-d]pyrimidine (110.1 mg, 0.5 mmol), [R]-1-phenylethylamine (74 mg, 0.6 mmol) and $NEt_3$ (111 mg, 1.1 mmol) in stirred propanol (2 mL) are heated at reflux under $N_2$ for 9 h. The mixture is allowed to cool, and is then purified by preparative tlc on silica, eluting once with 2% MeOH in $CHCl_3$. The yellow solid is recrystallized from EtOH at 0° C. to give 4-([R]-1-phenylethylamino)benzothieno[3,2-d]pyrimidine, (75 mg, 49%) as pale yellow cubic crystals. $^1$H NMR (DMSO) δ8.53(1H, s), 8.30(1H, d, J=7.2 Hz), 8.15 (1H, d, J=8.2 Hz), 7.68 (1H, dt, $J_d$=1.2 Hz, $J_f$=7.5Hz), 7.58 (1H, dt, $J_d$=1 Hz, $J_f$=7.5 Hz), 7.44 (1H, dd, J=1, 8 Hz), 7.31 (2H, t, J=7.7 Hz), 7.21 (1 H, tt, J=1, 7.7 Hz), 5.58(1H, q, J =7 Hz), 1.58 (3H, d, J=7 Hz).

EXAMPLE 15

4-(3-Bromoanilino)benzothieno[3,2-d]pyrimidine

4-Chlorobenzothieno[3,2-d]pyrimidine (110.1 mg, 0.5 mmol), (see preceding example) 3-bromoaniline (107.2 mg, 0.62 mmol) and $NEt_3$ (102.8 mg, 1.0 mmol) in stirred ethoxyethanol (2 mL) are heated at 110° C. under $N_2$ for 18 h. The solvent is removed under reduced pressure, and the dark oily residue is purified by preparative layer chromatography, eluting once with 2% MeOH in $CHCl_3$. The major band $R_f$ 0.40 is extracted to give a yellowish solid (147 mg) which is recrystallized from EtOH (20 mL) to give 4-(3-bromoanilino)benzothieno[3,2-d]pyrimidine (70 mg, 39%) as pale beige glistening plates. $^1$H NMR ($CDCl_3$) δ8.88(1H, s), 8.49(1H, dd, J=1.7, 7.1 Hz), 7.96 (1H, t, J=1.9 Hz), 7.89 (1H, dd, J=1.6, 7.0 Hz), (1H, d, J=7.8 Hz), 7.65 (1H, dt, $J_d$=1.5 Hz, $J_f$=7 Hz), 7.60 (1H, dd, J=1.5, 7.5 Hz), 7.57 (1H, dt, $J_d$=1.5 Hz, $J_f$=7 Hz), 7.40 (1H, dt, $J_d$=1.7 Hz, $J_f$=8 Hz),7.28 (1H, t, J=7.8 Hz), 6.90 (1H, brs).

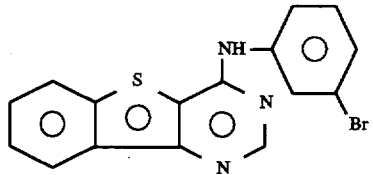

EXAMPLE 16

4-(3-Bromoanilino)-8-nitrobenzo[b]thieno[3,2-d]pyrimidine

2-Fluoro-5-nitrobenzonitrile. A mixture of 70% nitric acid and concentrated sulfuric acid (1:1, 30 mL) is added dropwise over 30 min to a solution of 2-fluorobenzonitrile (12.11 g, 0.10 mol) in concentrated sulfuric acid (50 mL), stirred under $N_2$ at 0° C. After a further 3h at 0° C. the yellow solution is poured onto ice (400 g), and the solid is collected by Buchner filtration, rinsed with water (4×50 mL), and dried in vacuo to give 2-fluoro-5-nitrobenzonitrile (15.43 g, 93%) as a pale yellow crystalline solid. $^1$H NMR ($CDCl_3$) δ8.56 (1H, dd, J=2.8, 5.5 Hz), 8.51 (1H, ddd, J=2.8, 4.4, 9.1 Hz), 7.44 (1H, dd, J=7.8, 9.0 Hz).

Ethyl 3-amino-5-nitrobenzothiophene-2-carboxylate. 2-Fluoro-5-nitrobenzonitrile (1.664 g, 10 mmol), ethyl thioglycollate (1.21 g, 10 mmol) and $NEt_3$ (3.06 g, 30 mmol) are stirred in DMSO (5 mL) at 100° C. under $N_2$ for h h. The deep orange-red reaction mixture is poured onto ice-water (50 mL), and the solid is collected by suction filtration, rinsed with water, and dried in a vacuum oven at 60° C. to give ethyl 3-amino-5-nitrobenzothiophene-2-carboxylate (2.675 g, 100%) as a bright orange solid. $^1$H NMR (DMSO) δ9.23 (1H, d, J=2.1 Hz), 8.28 (1H, dd, J=2.3, 8.9 Hz), 8.10 (1H, d, J=9.0 Hz), 7.45 (2H, brs), 4.29 (2H, q, J=7.1 Hz), 1.30 (3H, t, J=7.1 Hz).

8-Nitrobenzo[b]thieno[3,2-d]-3H-pyrimid-4-one. Ethyl 3-amino-5-benzothiophene-2-carboxylate (2.66 g, 10 mmol) is heated in formamide (10 mL) under $N_2$ at 190° C. for 4 h, and precipitates after 2 h. The solution is allowed to cool to 25° C., and the solid is collected by suction filtration, rinsed with EtOH (2×5 mL), and dried in a vacuum oven at 60° C. to give 8-nitrobenzo[b]thieno[3,2-d]-3H-pyrimid-4-one (1.91 g, 77%) as a highly crystalline orange-brown solid. $^1$H NMR (DMSO) δ13.00 (1H, brs), 8.85 (1H, s), 8.45 (3H, s).

4-Chloro-8-nitrobenzo[b]thieno[3,2-d]pyrimidine. DMF (0.75 g, 10.3 mmol) is added dropwise to a solution of oxalyl chloride (1.27 g, 10 mmol) in 1,2-dichloroethane (25 mL), stirred under $N_2$ at 25° C. When the vigorous gas evolution ceases, 8-nitrobenzo[b]thieno[3,2-d]-3H-pyrimid-4-one (1.236 g, 5 mmol) is added and the reaction mixture is heated to reflux. After 40 min, the hot reaction mixture is celite filtered, and then recrystallized at 0° C. to give 4-chloro-8-nitrobenzothieno[3,2-d]pyrimidine (759 mg, 57%) as a light brown solid. $^1$H NMR (DMSO) δ9.24 (1H, s), 8.99 (1H, d, J=2.0 Hz), 8.57, 8.53 (1H, 1H, ABq of d, $J_{AB}$=9.0 Hz, $J_d$=2, 0 Hz).

4-(3-Bromoanilino)-8-nitrobenzo[b]thieno-[3,2-d]pyrimidine. 4-Chloro-8-nitrobenzo[b]thieno-[3,2-d]pyrimidine (266 mg, 1.0 mmol), 3-bromoaniline (187.4 mg, 1.1 mmol) and NEt₃ (200 mg, 2.0 mmol) in stirred 1-propanol (4 mL) are heated at 110° C. under N₂ for 48 h, becoming a thick yellow paste. The mixture is cooled to 0° C., and the solid is collected by Buchner filtration, and air dried to give 4-(3-bromoanilino)-8-nitrobenzo[b]thieno[3,2-d]pyrimidine (275 mg, 69%) as a bright yellow solid. ¹H NMR (DMSO) δ10.12 (1H, brs), 9.03 (1H, s), 8.88 (1H, d, J=1.8 Hz), 8.54, 8.52 (1H, 1H, ABq of d, J$_{AB}$=7.5 Hz, J$_d$=0, 1.8 Hz), 8.18 (1H, d, J=1.7 Hz), 7.83 (1H, dd, J =1.5, 7.7 Hz), 7.37, 7.34 (1H, 1H, ABq of d, J$_{AB}$=7.7 Hz, J$_d$=7.7, 1.5 Hz).

EXAMPLE 17

8-Amino-4-(3-bromoanilino)benzo[b]thieno[3,2-d] pyrimidine 4-(3-Bromoanilino)-8-nitrobenzo[b]thieno-[3,2-d]pyrimidine (97 mg, 0.24 mmol) (see previous experimental) in THF (75 mL) is hydrogenated at 52 psi for 3 h, in the presence of Raney nickel (5 mg). The reaction mixture is filtered, and the filtrate is concentrated to small volume under reduced pressure, and the residue is purified by preparative thin layer chromatography on silica, eluting with 5% MeOH in CHCl₃. The band Rf 0.28 is extracted to give 8-amino-4-(3-bromoanilino)benzo[b]thieno[3,2-d] pyrimidine (47.2 mg, 53%) as a yellow solid. ¹H NMR (DMSO) δ9.66 (1H, brs), 8.72 (1H, s), 8.18 (1H, t, J=1.9 Hz), 7.84 (1H, ddd, J=1.2, 2.0, 8.1 Hz), 7.78 (1H, d, J=8.5 Hz), 7.50 (1H, d, J=2.2 Hz), 7.33 (1H, t, J=8.1 Hz), 7.27 (1H, ddd, J=1.2, 1.8, 8.0 Hz), 7.02 (1H, dd, J=2.3, 8.5 Hz), 5.47 (2H, brs).

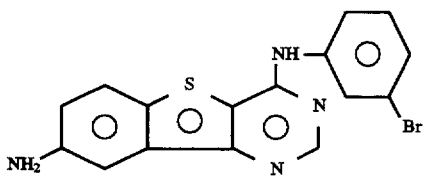

EXAMPLE 18

4-(3-Bromoanilino)-9-methoxybenzo[b]thieno[3,2-d]pyrimidine hydrochloride.

2-Fluoro-6-methoxybenzaldoxime. NH₂OHHCl (334 mg, 4.76 mmol) is added in portions to a solution of NaHCO₃ (395 mg, 4.7 mmol) in water (10mL) at r.t. To this solution was added dropwise a mixture of 2-fluoro-6-methoxybenzaldehyde (made from 3-fluoroanisole as described in Tetrahedron Lett. 1992, 33, 7499) (725 mg, 4.7 mmol) and EtOH (10 mL). The resulting mixture is stirred at r.t for 2 hr. The precipitate is collected by filtration and dried in a vacuum oven at ~50 C. overnight to give 2-fluoro-6-methoxybenzaldoxime (720 mg, 89%). ¹H NMR (DMSO) δ11.44, (1H, s), 8.16 (1H, s), 7.40, (1H, m) 6.85–6.95 (2H, m),3.84 (3H, s).

2-Fluoro-6-methoxybenzonitrile. A solution of 2-fluoro-6-methoxybenzaldoxime (714 mg, 4.2 mmol) in Ac₂O (3.6 mL) is heated at reflux for 4 hr. The reaction is cooled to r.t. and the volatiles are stripped off to give a beige solid, which is dried at 50° C. in a vacuum oven to give 2-fluoro-6-methoxybenzonitrile (635 mg, 84%). ¹H NMR (DMSO) δ7.8–7.7 (1H, m), 7.14–7.07 (2H, m),3.95 (3H, s).

Methyl 3-amino-4-methoxybenzothiophene-2-carboxylate. Methyl thioglycollate (0.18 mL, 1.9 mmol) is added dropwise to a suspension of NaH (60% oil suspension, 176 mg, 4.4 mmol) in DMSO (5 mL), stirred under N₂ at 25° C. When gas evolution ceases, 2-fluoro-6-methoxybenzonitrile (266 mg, 1.76 mmol) in DMSO 5 mL is added in one portion. After 3 h, the reaction mixture is poured onto ice-water, and the beige precipitate is collected by suction filtration, rinsed and air dried to give methyl 3-amino-4-methoxybenzothiophene-2-carboxylate (345 mg, 83%). ¹H NMR (DMSO) δ7.44–7.37 (2H, m), 7.00, (2H brs), 6.90 (1H, d, J=7.7Hz), 3.95 (3H, s), 3.76 (3H, s).

9-Methoxy-4-oxo-3H-benzothieno[3,2-d]pyrimidine. A mixture of methyl 3-amino-4-methoxybenzothiophene-2-carboxylate (202mg, 0.85mmol) and formamide (2mL) is heated at 135 C. for 1 hr and the temperature is raised to 190 C. After 8 hr the reaction is cooled to r.t. Upon cooling, black solid forms and is collected by filtration. The precipitate is air dried to give 9-methoxy-4-oxo-3H-benzothieno[3,2-d]pyrimidine (45 mg, 22.5%). ¹H NMR (DMSO) δ12.0 (1H, brs), 8.31 (1H, s)7.70–7.55 (2H, m), 7.10 (1H, d, J=7.7 Hz), 3.97 (3H, s).

4-Chloro-9-methoxybenzothieno[3,2-d]pyrimidine. DMF (0.125 mL, 1.7 mmol) is added dropwise to a solution of (COCl)₂ (0.15 mL, 1.68 mmol) in 1,2-dichloroethane (4.5 mL) at r.t. After gas evolution ceases, 9-methoxy-4-oxo-3H-benzothieno[3,2-d]pyrimidine (73.2 mg, 0.32 mmol) is added. The resulting mixture is heated at reflux for 4hr. After the reaction is cooled to r.t., the black tar is filtered off. The filtrate is stripped to dryness and then mixed with water. A yellow solid forms and is collected via filtration. The solid is washed with water and air dried to give 4-chloro-9-methoxybenzothieno[3,2-d]pyrimidine (53 mg, 66%). ¹H NMR (DMSO) δ9.17 (1H, s), 7.82–7.78 (2H, m), 7.3–7.2 (1H, m), 4.06 (3H, s).

4-(3-bromoanilino)-9-methoxybenzo[b]thieno-[3,2-d]pyrimidine hydrochloride. A mixture of 4-chloro-9-methoxybenzothieno[3,2-d]pyrimidine (53 mg, 0.21 mmol), 2-methoxyethanol (3 mL) and m-bromoaniline (0.03 mL, 0.28 mmol) is heated at 80 C. for 1 h. The reaction is cooled to r.t. and yellow solid precipitates. The solid is collected by filtration and dried in a vacuum oven at ~50 C. overnight to give 4-(3-bromoanilino)-9-methoxybenzo[b]thieno[3,2-d]pyrimidine hydrochloride (60 mg, 68%). ¹H NMR (DMSO) δ11.14 (1H, brs), 8.95 (1H, s), 8.07 (1H, d, J=1.7Hz), 7.87 (1H, d, J=8.2 Hz), 7.80 (1H, d, J=8.2 Hz), 7.76 (1H, d, J=7.5 Hz), 7.49 (1H, d, J=8.2 Hz), 7.44 (1H, t, J=8.0 Hz), 7.25 (1H, d, J=8.0 Hz), 4.10 (3H, s).

EXAMPLE 19

4-(3-Bromoanilino)thiazolo[4',5'; 4,5]thieno[3,2-d] pyrimidine

A mixture of 5-chlorothiazolo[4',5';4,5]-thieno[3,2-d] pyrimidine (prepared as described by Athmani and Iddon, Tetrahedron, 48, 7689, 1992) (66 mg, 0.29 mmol), 3-bromoaniline (0.033 mL, 0.3 mmol) and 2-methoxyethanol (3 mL) is heated at 95 C. for 2.5 h and then cooled to room temperature. The reaction is added to water, and the precipitate is collected by Buchner filtration and purified by preparative tlc on silica (2% MeOH/CHCl₃). The major band is extracted with 20% MeOH/CHCl₃. After removal of the solvent under reduced pressure 4-(3-bromoanilino)thiazolo[4',5'; 4,5]thieno[3,2-d]pyrimidine (25 mg, 23%) is obtained. ¹H NMR (DMSO) δ9.98 (1H, s), 9.67 (1H, s), 8.75 (1H, s), 8.17 (1H, s), 7.82 (1H, d, J=7.8 Hz), 7.38–7.31 (2H, m).

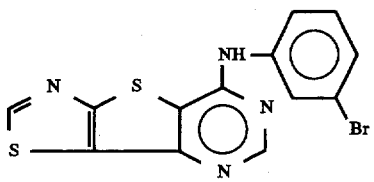

EXAMPLE 20

4-(3-Chloroanilino)pyrido[3',2':4,5]thieno[3,2-d]pyrimidine

Ethyl 3-aminopyrido[3,2-b]thiophene-2-carboxylate. A solution of 2-chloro-3-cyanopyridine (0.14 g, 1.0 mmol) in DMSO (2 mL) is added dropwise to a mixture of ethyl thioglycolate (0.12 mL, 1.1 mmol), NaH (0.06 g, 1.5 mmol) and DMSO (1 mL) stirred under $N_2$ at 25° C. After 3 h the reaction is worked up by pouring the reaction mixture onto stirred ice water. The light yellow precipitate is collected by Buchner filtration and dried in a vacuum oven to give ethyl 3-aminopyrido[3,2-b]thiophene-2-carboxylate (197 mg, 89%). $^1$H NMR (DMSO) δ8.68 (1H, dd, J=4.6, 1.6 Hz), 8.54 (1H, dd, J=8.2, 1.6 Hz), 7.46 (1H, dd, J=8.2, 4.5 Hz), 7.31 (2H, brs), 4.3 (2H, q, J=7.1 Hz), 1.29 (3H, t, J=7.1 Hz).

3H-Pyrido[3',2'; 4,5]thieno[3,2-d]pyrimid-4-one. A mixture of ethyl 3-aminopyrido[3,2-b]thiophene-2-carboxylate (0.92 g, 4.14 mmol) and formamide (10 mL) is heated at 135 C. for 1 h and then at 190 C. for 4 h. The reaction mixture is cooled to 25° C. producing a precipitate. The solid is collected by vacuum filtration and is washed with water and dried in a vacuum oven at 60° C. to give 3H-pyrido[3',2'; 4,5]thieno[3,2-d]pyrimid-4-one (0.61 g, 72.6%) as yellow-brown needles. $^1$H NMR (DMSO) δ13.0 (1H, brs), 8.86 (1H, dd, J=4.6, 1.6 Hz), 8.63 (1H, dd, J=8.0, 1.6 Hz), 8.4 (1H, s), 7.68 (1H, dd, J=8.1, 4.6 Hz).

4-Chloropyrido[3',2'; 4,5]thieno[3,2-d]pyrimidine. To a solution of $(COCl)_2$ (1.3 mL, 15 mmol) in 1,2-dichloroethane (75 mL) DMF (1.1 mL, 15 mmol) is added dropwise and stirred under $N_2$ at 25° C. After gas evolution ceases, 3H-pyrido[3',2'; 4,5]thieno[3,2-d]pyrimid-4-one (0.61 g, 3.0 mmol) is added to the mixture and the temperature is raised to 85 C. After 2 h, the reaction mixture is cooled to 25° C. and extracted with $CHCl_3$. The combined extracts are washed with water, saturated brine and dried $(MgSO_4)$. The solvent is removed in vacuo to give 4-chloropyrido[3',2'; 4,5]thieno[3,2-d]pyrimidine (0.64g, 96%) as a yellow solid. $^1$H NMR (DMSO) δ9.3 (1H, brs), 9.0 (1H, d, J=1.7 Hz), 8.9 (1H, dd, J=7.3, 0.8 Hz), 7.8 (1H, dd, J=4.7, 0.8 Hz).

4-(3-Chloroanilino)pyrido[3',2':4,5]thieno[3,2-d]pyrimidine. A mixture of 4-chloropyrido [3',2'; 4,5]thieno [3,2-d]pyrimidine (0.12 g, 0.54 mmol), 3-chloroaniline (0.06 mL, 0.5 mmol) and 2-ethoxyethanol (5 mL) is heated under $N_2$ with stirring at 135 C. for 3 h. Upon cooling a solid precipitates. The solid is collected by filtration, washed with acetone and dried in a vacuum oven at ~80 C. to give 4-(3-chloroanilino)pyrido[3',2'; 4,5]thieno[3,2-d]pyrimidine (46 mg, 27%). $^1$H NMR (DMSO) δ9.97 (1H, s), 8.88 (1H, dd, J=4.6, 1.7 Hz), 8.85 (1H, s), 8.72 (1H, dd, J=8.0, 1.7 Hz), 8.08 (2H, t, J=2.0 Hz), 7.79 (1H, ddd, J=8.3, 2.0, 0.8 Hz), 7.69 (1H, dd, J=8.0, 4.6 Hz), 7.43 (1H, t, J=8.0 Hz), 7.19 (1H, ddd, J=8.0, 2.0, 0.8 Hz).

EXAMPLE 21

4-(3-bromoanilino)pyrido[3',2'; 4,5]thieno[3,2-d]pyrimidine

A mixture of 4-chloropyrido[3',2'; 4,5]thieno[3,2-d]pyrimidine (72 mg, 0.32 mmol) (see previous experimental), 3-bromoaniline (0.04 mL, 0.37 mmol) and 2-ethoxyethanol (5 mL) is heated under $N_2$ with stirring at 135 C. for 3 h. Upon cooling a solid precipitates. The solid is collected by filtration, washed with acetone and dried in a vacuum oven at ~80 C. to give 4-(3-bromoanilino)pyrido[3',2'; 4,5]thieno [3,2-d]pyrimidine (45 mg, 39.4%). $^1$H NMR (DMSO) δ9.96 (1H, s), 8.88 (1H, dd, J=4.6, 1.7 Hz), 8.85 (1H, s), 8.72 (1H, dd, J=8.0, 1.7 Hz), 8.20 (1H, t, J=2.0 Hz), 7.84 (1H, ddd, J=8.0, 2.0, 1.3 Hz), 7.69 (1H, dd, J=8.0, 4.7 Hz), 7.39–7.31 (2H, m).

EXAMPLE 22

4-Anilinoindolo[3,2-d]pyrimidine

A solution of 4-chloroindolo[3,2-d]pyrimidinehydrochloride (240 mg, 1.0 mmol) [Monge, A.; Palop, J. A.; Goni, T.; Martinez-Crespo, F.; Recalde, I. *J. Het. Chem.*, 1986, 23, 647–9.], and aniline (0.273 mL, 3 mmol) in ethanol (1 mL) is heated at reflux for 3 h, during which time the reaction becomes a thick suspension. After cooling to 25 C. and diluting with ethanol (4 ml) the mixture is filtered, and the crude product washed with water (15 mL), and ethanol (15 mL), giving 274 mg tan solid, which is recrystallized from DMF/water affording pure 4-anilinoindolo[3,2-d]pyrimidine hydrochloride (82 mg, 27%). $^1$H NMR (DMSO): δ12.79 (1H, brs), 11.04 (1H, brs), 8.94 (1H, s), 8.27 (1H, d, J=8.2 Hz), 7.96 (2H, d, J=7.5 Hz), 7.85 (1H, d, J=8.4 Hz), 7.71 (1H, t, J=7.7 Hz), 7.49 (2H, t, J=8.0 Hz), 7.41 (1H, t, J=7.6 Hz), 7.24 (1H, t, J=7.4 Hz).

EXAMPLE 23

4-Benzylaminoindolo[3,2-d]pyrimidine

4-Chloroindolo[3,2-d]pyrimidine hydrochloride (240 mg, 1 mmol, and benzylamine (1 mL) are stirred under a dry nitrogen atmosphere at 150 C. for 6 hours, and then concentrated under reduced pressure to give an oily soft solid which is dissolved in EtOAc (20 mL), and washed with saturated sodium bicarbonate solution (20 mL), water (3×15 mL), and brine (20 mL). The solution is dried $(MgSO_4)$ and the solvent is removed under reduced pressure. Trituration of the residue with dichloromethane, gives 4-benzylaminoindolo[3,2-d]pyrimidine (190 mg, 69%). $^1$H NMR $(CDCl_3)$: δ10.58 (1H, brs), 8.60 (1H, s), 8.08 (1H, d, J=8.0 Hz), 7.47–7.14 (8H, m), 4.82 (2H, d, J=5.6 Hz), 2.41 (1H, brs).

EXAMPLE 24

4-([R]-1-Phenylethylamino)indolo[3,2-d]pyrimidine hydrochloride

4-Chloroindolo[3,2-d]pyrimidine hydrochloride 240 mg, 1 mmol) and (R)-(+)-methylbenzylamine (1 ml) are stirred under a dry nitrogen atmosphere at 150 for 5 hours, and then concentrated under reduced pressure to an oil. This oil is dissolved in EtOAc (20 ml), and stirred for 16 h. The precipitate which forms is collected by filtration, washed with EtOAc, and dried at 90 in vacuo to give 4-([R]-1-phenylethylamino)indolo[3,2-d]pyrimidine hydrochloride (37 mg, 11%). $^1$H NMR (DMSO): δ10 (1H, s), 9.14 (1H, brs), 8.64 (1H, s), 8.16 (1H, d, J=8.0 Hz), 7.74 (1H, d, J=8.5 Hz), 7.63–7.59 (1H, m), 7.50 (2H, d, J=7.2 Hz), 7.38–7.24 (4H, m), 5.59 (1H, p, J=7.0 Hz); 1.64 (3H, d, J=7.0 Hz).

EXAMPLE 25

4-(3-Bromoanilino)indolo[3,2-d]pyrimidine hydrochloride

4-Chloroindolo[3,2-d]pyrimidine hydrochloride (240 mg, 1 mmol) and 3-bromoaniline (0.33 mL, 3 mmol) in ethanol (3 mL) are heated at reflux under a nitrogen atmosphere for 2h. Filtration and washing of the collected solids with ethanol, followed by recrystallization from DMF gives 4-(3-bromoanilino)indolo[3,2-d]pyrimidine hydrochloride (288 mg, 77%). $^1$H NMR (DMSO) δ12.73 (1H, s), 11.42 (1H, s), 9.02 (1H, s), 8.41 (1H, s), 8.28 (1H, d, J=7.9 Hz), 7.95–7.92 (1H, m), 7.84–7.82 (1H, d, J=8.6 Hz), 7.74–7.69 (1H, m), 7.40–7.47 (3H, m).

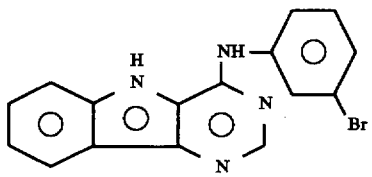

EXAMPLE 26

4-(3-Bromoanilino-5,N-methylindolo[3,2-d] pyrimidine hydrochloride

A solution of 4-chloro-5,N-methylindolo[3,2-d] pyrimidine (Kadushkin, A. V.; Nesterova, I. N.; Golovko, T. V.; Nikolaeva, I. S.; Pushkina, T. V.; Fomina, A. N.; Sokolova, A. S.; Chernov, V. A.; Granik, V. G. Khim.-Farm. Zh. 1990, 24, 18–22) (218 mg, 1 mmol) and 3-bromoaniline (0.33 mL, 3 mmol) in 2-propanol (7 mL) containing 0.5% HCl gas is heated at reflux for 3 hr, cooled to 25 C., and the solids are filtered and washed with 2-propanol and dried affording 4-(3-bromoanilino)-5,N-methylindolo[3,2-d] pyrimidine hydrochloride (379 mg, 97%), as a bright yellow solid. $^1$H NMR (DMSO) δ9.80 (1H, s), 8.83 (1H, s), 8.34 (1H, d, J=8.0 Hz), 7.95–7.90 (2H, m), 7.79–7.68 (3H, m), 7.45–7.41 (3H, m), 4.27 (3H, s).

EXAMPLE 27

4-Anilinoindolo[2,3-d]pyrimidine

4-Chloroindolo[2,3-d]pyrimidine hydrochloride (R. G. Glushkov et. al., Khim.-Farm. Zh., 1967, 1(9), 25–32) (240 mg, 1 mmol) and aniline (0.27 mL, 3 mmol) in ethanol (1 mL) are heated under reflux for 6 h. The solvent is evaporated under reduced pressure, and the residue triturated with EtOAc to afford a tan powder which is filtered, and washed with cold ethanol. Recrystallization from acetone/pet. ether gives 4-anilinoindolo[2,3-d]pyrimidine (49 mg, 19%). $^1$H NMR (DMSO) δ1H, s), 8.84 (1H, s), 8.43 (1H, s), 8.37 (1H, d, J=8.0 Hz), 7.74 (2H, d, J=7.7 Hz), 7.52–7.08 (6H, m).

EXAMPLE 28

4-(3-Bromoanilino)indolo[2,3-d]pyrimidine hydrochloride

4-Chloroindolo[2,3-d]pyrimidine hydrochloride (240 mg, 1 mmol) and 3-bromoaniline (0.33 mL, 3 mmol) in ethanol (3 mL) are heated under reflux for 2h. The solids are collected by suction filtration, washed with ethanol and dried to give 4-(3-bromoanilino)indolo[2,3-d]pyrimidine hydrochloride (248 mg, 73%). $^1$H NMR (DMSO) δ1H, s), 9.02 (1H, s),8.51 (1H, s), 8.42 (1H, d, J=7.7 Hz), 8.08 (1H, t, J=1.9 Hz), 7.82 (1H, d, J=8.0 Hz), 7.53 (1H, d, J=7.9 Hz), 7.46 (1H, dr, $J_d$=1.0 Hz, $J_f$=7.6 Hz), 7.36–7.27 (3H, m).

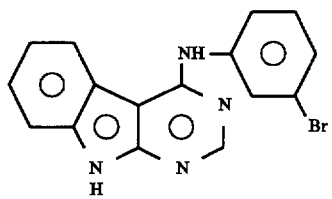

EXAMPLE 29

4-(3-Bromoanilino-9,N-methylindolo[2,3-d] pyrimidine.

4-Chloro-9,N-methylindolo[2,3-d]pyrimidine (Portnov, Yu. N.; Bulaga, S. N.; Zabrodnyaya, V. G.; Smirnov, L. D. Khim. Geterotsikl. Soedin., 1991, 3, 400–2) (220 mg, 1 mmol) and 3-bromoaniline (0.33 mL, 3 mmol) in 2-propanol, containing 0.5% (w:w) HCl gas, (7 mL) is heated under reflux for 6 h. After removal of solvent under reduced pressure, the residue is suspended in CHCl$_3$ (50 mL), and washed with 1% aqueous NaOH solution (25 mL), and H$_2$O (2×20 mL), dried (MgSO$_4$), and concentrated under reduced pressure. Column chromatography (SiO$_2$) with CHCl$_3$ gives the product as a light tan foam, which slowly crystallizes upon standing at 25 C. Recrystallization from diisopropyl ether (~30 ml) affords 4-(3-bromoanilino)-9,N-methylindolo[2,3-d]pyrimidine (220 mg, 65%)as a fluffy white solid. $^1$H NMR (CDCl)$_3$ δs,s,m, 3.96 (3H, s).

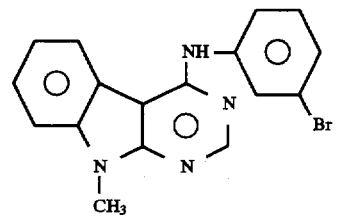

EXAMPLE 30

4-(3-Bromoanilino-9N-(2-N,N-diethylaminoethyl) pyrimido[2,3-d]indole bis hydrochloride 4-Chloro-9N-(2-N,N-dimethylamino)ethyl)indolo[2,3-d] pyrimidine. A suspension of 4-chloroindolo[2,3-d] pyrimidine hydrochloride (407 mg, 2 mmol), 2-N,N-diethylaminoethyl chloride hydrochloride (413 mg, 2.4 mmol), anhydrous cesium carbonate (1.95 g, 6 mmol) and 4 molecular sieves (1.5 g) in acetone (6 mL) are heated at reflux under a nitrogen atmosphere for 1.5 h. The mixture is filtered through celite, washing the filter cake with acetone (4×10 ml), followed by concentration of the filtrate under reduced pressure affording a viscous amber oil, which is dissolved in CH$_2$Cl$_2$, (20 ml), and washed with water (2×25 mL), dried (MgSO$_4$), and the solvent is removed in vacuo. The crude product is chromatographed on silica, eluting with 4% methanol/chloroform to give 4-chloro-9N-(2-(N, N-diethylamino)ethyl)indolo[2,3-d]pyrimidine (495 mg, 82%), as a pale yellow oil. $^1$H NMR (DMSO) δ8.79 (1H, s), 8.41 (1H, d, J=8.0 Hz), 7.66–7.58 (2H, m), 7.46–7.42 (1H, m), 4.57 (2H, t, J=6.8 Hz), 2.90 (2H, t, J=7.1 Hz), 2.63 (4H, d, J=7.0 Hz), 0.99 (6H, t, J=7.0 Hz).

4-(3-Bromoanilino)-9N-(2-N,N-diethylaminoethyl) pyrimido[2,3-d]indole bis hydrochloride. A suspension of 4-chloro-9N-(2-(N,N-diethylamino)ethyl)indolo[2,3-d] pyrimidine (240 mg, 1 mmol) and 3-bromoaniline (0.33 mL, 3 mmol) in 2-propanol (7 mL), which contains 0.5% HCl gas, is heated under reflux for 6 hr, and then concentrated to a viscous brown oil which is dissolved in chloroform (75 mL) and washed with 1% aqueous NaOH solution (50 mL), water (50 mL), and dried (MgSO$_4$). The solvent is removed under reduced pressure, and the residue is chromatographed on SiO$_2$ eluting with 2% MeOH in CHCL$_3$ to obtain the free base of the product as a pale yellow oil (411 mg, 93%). The free base is dissolved in warm ethanol (5 mL), and is treated with ethanol (2 mL) which had been saturated with HCl gas, affording 4-(3-bromoanilino)-9N- (2-N,N-diethylaminoethyl)indolo[2,3-d]pyrimidine bis hydrochloride. 1H NMR (DMSO) δ10.64 (1H, brs), 9.17 (1H, s), 8.60 (1H, s), 8.52 (1H, d, J=8.0 Hz), 8.07 (1H, s), 7.93 (1H, d), 7.80 (1H, d, J=7.7 Hz), 7.58 (1H, t, J=7.7 Hz), 7.41 (1H, t, J=7.2 Hz), 7.37 –7.39 (2H, m), 4.90 (2H, t, J=7.0 Hz), 3.51 (2H, dd, J=12.8, 6.5 Hz) 3.31–3.28 (4H, m), 1.25 (6H, t, J=7.2 Hz).

EXAMPLE 31

4-(3-Bromoanilino)6-methoxyindolo[2,3-d]pyrimidine

Cyano-(5-methoxy-2-nitrophenyl)acetic acid ethyl ester. To an ice-cold solution of ethyl cyanoacetate (10.9 mL, 102.4 mmol) in anhydrous THF (170 mL) under N$_2$ is added of potassium tert-butoxide (12.07 g, 107.5 mmol). The formed white suspension is stirred for 15 min then treated with 3-fluoro-4-nitroanisole [Halfpenny, P. R.; Horwell, D. C.; Hughes, J.; Hunter, J. C.; Rees, D. C. J. Med. Chem. (1990), 33, 286–91] (8.86 g, 51.2 mmol). The suspension is heated at reflux for 1.5 h. The solution is poured into H$_2$O, and the aqueous mixture is acidified to pH 2 with concentrated HCl. The mixture is extracted three times with ether then the combined organic phases are dried (MgSO$_4$) and concentrated to an oil that is pumped at 0.3 mm for 2 days. The oil is dissolved in dichloromethane and purified by flash silica gel chromatography eluting with dichloromethane. The product fractions are combined and concentrated to leave cyano-(5-methoxy-2-nitrophenyl)acetic acid ethyl ester (14.5 g) as a light yellow oil that is about 93–95% pure. $^1$H NMR (CDCl$_3$): δ8.29 (1H, d, J=9.2 Hz), 7.22 (1H, d, J=2.7 Hz), 7.04 (1H, dd, J=9.2, 2.7 Hz), 5.69 (1H, s), 4.31 (2H, q, J=7.0 Hz), 1.34 (3H, t, J=7.2 Hz).

2-Amino-5-methoxy-1H-indole-3-carboxylic acid ethyl ester. A solution of cyano-(5-methoxy-2-nitrophenyl)acetic acid ethyl ester (13.2 g, 46.3 mmol, 93–95% pure) in glacial acetic acid (185 mL) is treated with a single charge of zinc dust (12.1 g, 185 mmol). The mixture is heated at 55° C. for 45 min, then treated with more zinc (4 g). After heating for another 105 min, the brown mixture is filtered through a pad of flash silica gel. The pad is washed well with acetic acid and the filtrate is concentrated to a residue that is distributed between dichloromethane and H$_2$O. The organic phase is washed with 5% aqueous sodium bicarbonate and concentrated to a residue that shows about a 1:1 mixture of products by silica gel thin layer chromatography (dichloromethane:EtOAc, 3:1). The residue is purified by flash silica gel chromatography eluting sequentially with 100:0, 95:5, and 90:10 dichloromethane:EtOAc. The fractions containing the pure higher R$_f$ product are combined and concentrated to a solid that is sonicated in tert-butyl methyl ether. The solids are collected by filtration to give pure 2-amino-5-methoxy-1H-indole-3-carboxylic acid ethyl ester (2.07 g) as an off-white solid. Further chromatography of the combined mother liquor and impure fractions affords 120 mg of additional product. Total yield=2.19 g (20%). $^1$H NMR (DMSO) : δ10.44 (1H, br s, exchanges with D$_2$O), 7.11 (1H, d, J=2.2 Hz), 6.98 (1H, d, J=8.4 Hz), 6.61 (2H, br s, exchanges with D$_2$O), 6.48 (1H, dd, J=8.4, 2.7 Hz), 4.20 (2H, q, J=7.0 Hz), 3.71 (3H, s), 1.32 (3H, t, J=7.2 Hz).

6-Methoxy-3H-indolo[2,3-d]pyrimidine-4-one. A solution of 2-amino-5-methoxy-1H-indole-3-carboxylic acid ethyl ester (2.15 g (9.2 mmol), sodium methoxide (0.5 g (9.3 mmol), and formamide (200 mL), is heated under N$_2$ at 220° C. for 1.5 h. The solution is cooled to room temperature, stored for 2.5 days, and filtered. The solvent is evaporated by Kugelrohr distillation at 95° C./0.8 mm. The residual solids are washed with H$_2$O, then heated in 35 mL of boiling N,N-dimethylformamide. The hot suspension is filtered hot over a pad of flash silica gel. The cooled filtrate is concentrated in vacuo to a solid that is sonicated in about 30 mL of MeOH. The solids are filtered, washed with MeOH, and dried to leave 6-methoxy-3H-indolo[2,3-d]pyrimidine-4-one (1.71 g,72%) that is about 83% pure. $^1$H NMR (DMSO): δ12.16 (1H, br s, exchanges with D$_2$O), 12.04 (1H, br s, exchanges with D$_2$O), 8.08 (1H, d, J=3.4 Hz, exchanges to s with D$_2$O), 7.46 (1H, d, J=1.9 Hz), 7.37 (1H, d, J=8.7 Hz), 6.95 (1H, dd, J=8.8, 2.5 Hz), 3.81 (3 H, s).

4-Chloro-6-methoxyindolo[2,3-d]pyrimidine. A suspension of 6-methoxy-3H-indolo[2,3-d]pyrimidine-4-one (800 mg, 3.08 mmol, ~83% pure) and POCl$_3$ (7 mL) is heated at 90° C. for 6 h. The suspension is concentrated to a solid that is evacuated at 1 mm for 1 h. The solids are cooled in a –78° C. bath then treated dropwise with cold H$_2$O. The bath is removed and the frozen solids are allowed to gradually melt. The solids are filtered, washed well with cold H$_2$O, and dried to leave 4-chloro-6-methoxyindolo[2,3-d]pyrimidine (733 mg, 81%) that is about 80% pure. $^1$H NMR (DMSO): δ12.64 (1H, br s, exchanges with D$_2$O), 8.74 (1H, s), 7.74 (1H, d, J=2.4 Hz), 7.57 (1H, d, J=8.9 Hz), 7.28 (1H, dd, J=8.9, 2.4 Hz), 3.88 (3H, s).

4-(3-Bromoanilino)-6-methoxyindolo[2.3-d]-pyrimidine. A mixture of 4-chloro-6-methoxyindolo[2,3-d]pyrimidine (107 mg, 0.37 mmol, 80% pure), 3-bromoaniline (0.15 mL, 1.4 mmol), N,N-dimethylacetamide (1 mL), and 1 drop of a solution of 2-propanol that is 8.5 molar in HCl is heated under N$_2$ at 120° C. for 5 h. The solution is concentrated in vacuo to an oily solid that is triturated in 5% aqueous sodium bicarbonate. The solids are collected by filtration, then washed successively with H$_2$O and EtOAc. The solids are warmed in a small volume of N,N-dimethylformamide and filtered. The filtrate is purified by thick layer silica gel chromatography eluting with 3:2 dichloromethane:EtOAc. The product band is collected and sonicated in EtOAc. The mixture is filtered and the filtrate is concentrated to a solid that is sonicated in MeOH. The solids are collected, washed with MeOH, and dried to give pure 4-(3-bromoanilino)-6-methoxyindolo[2,3-d]pyrimidine ( 39 mg, 28%) hydrated with 0.7 equivalent of H$_2$O. $^1$H NMR (DMSO): δ11.99 (1H, br s, exchanges with D$_2$O), 8.97 (1H, br s, exchanges with D$_2$O), 8.44 (1H, s), 8.02 (1H, s), 7.91 (1H, d, J=2.4 Hz), 7.76 (1H, d, J=8.0 Hz), 7.42 (1H, d, J=8.7 Hz), 7.36–7.24 (2H, m), 7.08 (1H,dd, J=8.7, 2.2 Hz), 3.87 (3H, s).

EXAMPLE 32

2-Amino-4-(3-bromoanilino)pyrimido[2,3-d]indole

2-Guanidinoindole-3-carboxylic acid ethyl ester hydrochloride. A suspension of 2 aminoindole-3-carboxylic acid ethyl ester ( 2.04 g, 10.0 mmol), cyanamide (534 mg, 12.7 mmol), and concentrated hydrochloric acid (1 mL) in dioxane (91 mL), are heated under reflux for 48 hr. After the reaction mixture has cooled to 25 C. it is filtered and the solids washed well with dry diethyl ether, and then air dried to give 2-guanidinoindole-3-carboxylic acid ethyl ester hydrochloride (1.08g, 38%) 2-guanidinoindole-3-carboxylic acid ethyl ester hydrochloride as an off-white solid, mp>250 C.

2-Amino-4-oxo-3H-indolo[2,3-d]pyrimidine. A mixture of 2-guanidinoindole-3-carboxylic acid ethyl ester hydrochloride (1.00 g, 3.5 mmol) and sodium hydroxide (1.5 g) in water (50 mL) is heated to gentle reflux for 6 hr followed by the addition of sufficient 5% HCl to adjust the solution to pH 1, and filtration of the resulting mixture through celite, washing the pad with water. The filtrate is extracted with ethyl acetate (3×25 mL), and then basified with solid sodium carbonate. The tan precipitate which slowly forms is collected by filtration, washed with water, and dried in vacuo affording 2-amino-4-oxo-3H-indolo[2,3-d]pyrimidine (561 mg, 78%) as light tan crystals, mp>275 C.

2-Amino-4-chloroindolo[2,3-d]pyrimidine hydrochloride. A suspension of 2-amino-4-oxo-3H-indolo[2,3-d]pyrimidine (490 mg, 2.5 mmol) and phosphoryl chloride (7 ml, 75 mmol) in dioxane (13 ml) is heated under reflux for 4 hr, then concentrated in vacuo. The residue is triturated with ethanol, filtered, and the solids washed with 10:1 Ethanol:Ethyl Acetate to give 170 mg (27%) 2-amino-4-chloroindolo[2,3-d]pyrimidine hydrochloride as a grey solid, mp>250 C.

2-Amino-4-(3-bromoanilino)indolo[2,3-d]pyrimidine. A mixture of 2-amino-4-chloroindolo[2,3-d]pyrimidine hydrochloride (123 mg, 0.6 mmol) and 3-bromoaniline (0.3 mL, 2.8 mmol) in 2-propanol (6 mL) is heated at reflux for 4 hr, filtered through a celite pad, and concentrated in vacuo. The residue is partitioned between ethyl acetate (25 mL) and water (25 mL). The aqueous phase is extracted with further ethyl acetate (2×20 mL), followed by washing the combined extracts with 1% aqueous sodium hydroxide (25 mL), water (2×40 mL), saturated brine (40 mL), and drying ($Na_2SO_4$). The solution is evaporated to dryness under reduced pressure to afford 105 mg crude product as a tan powder. The solid is dissolved in a minimum amount of methanol, filtered, and further purified by preparative plate chromatography ($SiO_2$; 1:1, EtOAc: $CH_2Cl_2$; $R_f$=0.40 ). After extraction of the product from the silica gel with ethyl acetate, the volume of the warm solution is reduced to minimum, and it is filtered through celite, and the solvent is removed under reduced pressure. The oily solid thus obtained is dissolved in a minimum amount of 2-propanol and allowed to crystallize at 3 C. over an 18 h period. The crystals are collected by suction filtration, washed with a small amount of cold 2-propanol, and dried in vacuo to give 2-amino-4-(3-bromoanilino) indolo[2,3-d]pyrimidine (34 mg, 17%). $^1$HNMR, (DMSO): δbrs), 8.57 (1H, s), 8.11 (1H, d, J=8.0 Hz), 8.01 (1H, s), 7.94 (1H, d, J=8.2 Hz), 7.34–7.12 (5H, m), 6.41 (2H, brs).

EXAMPLE 33

4-(3-Bromoanilino)-9N-(2-N,N-diethylaminoethyl)-6-methoxyindolo[2,3-d]pyrimidine bishydrochloride 4-Chloro-6-methoxy-9H-(2-N,N-diethylaminoethyl) indolo[2,3-d]pyrimidine. A suspension of 4-chloro-6-methoxyindolo[2,3-d]pyrimidine (773 mg, 2.5 mmol, ~80% pure), 2-diethylaminoethyl chloride hydrochloride (582 mg, 3.4 mmol ), anhydrous cesium carbonate (2.3 g, 7.1 mmol), 4 molecular sieves (2.1 g), and acetone:N,N-dimethylformamide (12 mL, 2:1) is heated at reflux under $N_2$ for 16.5 h The mixture is filtered over Celite® and the filter pad is washed well with acetone. The filtrate is concentrated in vacuo to a viscous oil that is distributed between dichloromethane and $H_2O$. The organic phase is dried ($MgSO_4$) and concentrated to an oil that is purified by flash silica gel chromatography eluting first with dichloromethane, then with dichloromethane:MeOH (98:2). The product fractions are combined and concentrated in vacuo to leave 4-chloro-6-methoxy-9H-(2-N,N-diethylaminoethyl)indolo[2,3-d]pyrimidine (667 mg, 80 %) as a yellow oil. $^1$H NMR ($CDCl_3$): δ8.75 (1H, s), 7.87 (1H, d, J=2.4 Hz), 7.47 (1H, d, J=8.9 Hz), 7.25 (1H, dd, J=8.9, 2.4 Hz), 4.50 (2H, t, J=7.2 Hz), 3.96 (3H, s), 2.86 (2H, t, J=7.1 Hz), 2.59 (4H, q, J=7.1 Hz), 0.96 (6H, t, J=7.1 Hz).

4-(3-Bromoanilino)-6-methoxy-9H-(2-N,N-diethylaminoethyl)indolo[2,3-d]pyrimidine bishydrochloride. A solution of 4-chloro-6-methoxy-9H-(2-N,N-diethylaminoethyl)indolo[2,3-d]pyrimidine (660 mg, 1.98 mmol), 3-bromoaniline (0.52 mL, 4.8 mmol, 0.25 mL of a solution of 2-propanol that is 8.5 molar in HCl, and N,N-dimethylacetamide (4 mL) is heated at 120° C. under $N_2$ for 2 h. The solution is concentrated in vacuo and the residue is distributed between dichloromethane and 1% aqueous sodium hydroxide. The dichloromethane phase is washed with $H_2O$, dried ($MgSO_4$), and concentrated to an oil that is purified by flash silica gel chromatography eluting first with EtOAc, then EtOAc:MeOH:triethylamine (95:5:1). The product fractions are combined and concentrated to leave an oil that is stored at room temperature overnight. The semi-solid is treated with an excess of a solution of 2-propanol that is 8.5 molar in HCl. After storage for several hours at room temperature, the solids are collected by filtration, washed with 2-propanol, and dried to leave 4-(3-bromoanilino)-6-methoxy-9H-(2-N,N-diethylaminoethyl) indolo[2,3-d]pyrimidine (727 mg, 65%) as a salt with 2.1 equivalents of HCl and solvated with 0.9 equivalent of $H_2O$. $^1$H NMR (DMSO): δ10.55 (1H, br s, exchanges with $D_2O$), 9.28 (1H, br s, exchanges with $D_2O$), 8.55 (1H, s), 8.02 (1H, d, J=2.2 Hz), 7.99 (1H, s), 7.84 (1H, d, J=8.7 Hz), 7.74 (1H, d, J=7.2 Hz), 7.39–7.32 (2H, m), 7.21 (1H,dd, J=8.9, 2.2 Hz), 5.30 (3H, br s, exchanges with $D_2O$), 4.85 (2H, t, J=7.2 Mz), 3.90 (3M, s), 3.48 (2H, dd, J=12.2, 6.4 Hz); 3.35–3.21 (4H, m); 1.23 (6H, t, J=7.2 Hz).

EXAMPLE 34

4-(3-Bromoanilino)benzofurano[3,2-d]pyrimidine

Methyl 2-(2-cyanophenoxy)ethanoate. Methyl bromoacetate (1.95 mL, 20 mmol) is added dropwise to a solution of 2-cyanophenol (2.38 g, 20 mmol), and $K_2CO_3$ (2.78 g, 20.1 mmol) in acetone (100 mL) stirred under $N_2$ at 25° C. After 24 h, the solid is filtered off and the filtrate is concentrated in vacuo and the residue is dried in a vacuum oven to give methyl 2-(2-cyanophenoxy)ethanoate (3.82 g, 100%) as a beige solid. $^1$H NMR (DMSO) δ7.76 (1H, dd, J=7.6, 1.7 Hz), 7.64 (1H, dt, $J_d$=1.6 Hz, $J_t$=8.0 Hz), 7.20–7.10 (2H, m), 5.04 (2H, brs), 3.70 (3H, s).

Methyl 3-aminobenzo[b]furan-2-carboxylate. A solution of methyl 2-(2-cyanophenoxy) ethanoate (3.82 g, 20 mmol) in DMSO (40 mL) is added dropwise to a suspension of NaH (0.84 g, 21 mmol) and DMSO (10 mL) stirred under $N_2$ at 25° C. After 10 min the mixture is poured onto ice water and extracted with ether. The combined extracts are washed with water, saturated brine and dried ($MgSO_4$). After removal of the solvent under reduced pressure, methyl 3-aminobenzo

[b]furan-2-carboxylate (2.15 g, 56%) is obtained as a yellow solid. $^1$H NMR (DMSO) δ7.95 (1H, d, J=7.7 Hz), 7.48 (2H, d, J =3.4 Hz), 7.29–7.22 (1H, m), 6.40 (2H, brs), 3.80 (3H, s).

3H-Benzofurano[3,2-d]pyrimid-4-one. A solution of methyl 3-aminobenzo[b]furan-2-carboxylate (0.28 g, 1.36 mmol) in formamide (5 mL) is heated at 135 C. for 4 h, then the temperature is raised to 170 C. After 4 h the reaction is cooled to 25° C. and a dark purple solid precipitates. The solid is collected by vacuum filtration and air dried to give 3H-benzofurano[3,2-d]pyrimid-4-one (118 mg, 46.6%). $^1$H NMR (DMSO) δ13.0 (1H, brs), 8.25 (1H, s), 8.05 (1H, d, J =8.1 Hz), 7.84 (1H, d, J=8.3 Hz), 7.68 (1H, t, J=7.7 Hz), 7.51 (1H, t, J=7.7 Hz).

4-Chlorobenzofurano[3,2-d]pyrimidine. DMF (0.23 mL, 3.1 mmol) is added dropwise to a solution of $(COCl)_2$ (0.28 mL, 3.1 mmol) in 1,2-dichloroethane (15 mL) at 25° C. After gas evolution ceases, 3H-benzofurano[3,2-d]pyrimid-4-one (113 mg, 0.61 mmol) is added. The resulting mixture is heated at reflux for 1 h. After the reaction has cooled to 25° C., water is added and the resulting mixture is extracted with $CHCl_3$. The combined extracts are washed with water, saturated brine and dried $(MgSO_4)$. The solvent is removed under reduced pressure to give 4-chlorobenzofurano[3,2-d]pyrimidine (116 mg, 93%) as a yellow solid. $^1$H NMR (DMSO) δ9.08 (1H, s), 8.30 (1H, d. J=8.1 Hz), 8.02 (1H, d, J=8.5 Hz), 7.90, (1H, dr, $J_d$=1.3 Hz, $J_t$=7.1 Hz), 7.64 (1H, dt, $J_d$=1.0 Hz, $J_t$=7.8 Hz).

4-(3-Bromoanilino)benzofurano[3,2-d]pyrimidine. A mixture of 4-chlorobenzofurano[3,2-d]pyrimidine (116mg, 0.57 mmol) and 3-bromoaniline (0.07 mL, 0.6 mmol) is heated at 135° C. under $N_2$ in stirred 2-ethoxyethanol for 3 h. The mixture precipitates upon cooling, and the solid is collected and recrystallized from EtOH to give 4-(3-bromoanilino)benzofurano[3,2-d]pyrimidine (15.7 mg, 8%). $^1$H NMR (DMSO) δ10.35 (1H, s), 8.73 (1H, s), 8.34 (1H, t, J=1.9 Hz), 8.17 (1H, ddd, J=7.2, 1.2, 0.7 Hz), 7.93 (1H, ddd, J=8.2, 2.2, 1.0 Hz), 7.88 (1H, d, J=8.4 Hz), 7.77 (1H, dt, $J_d$=1.4 Hz, $J_t$=7.2 Hz), 7.56 (1H, dt, $J_d$=0.8 Hz, $J_t$=8.0 Hz), 7.34 (1H, t, J=8.0 Hz), 7.27 (1H, ddd, J=8.0, 2.0, 1.0 Hz).

The pharmaceutical compositions of the invention can take any of a wide variety of oral and parenteral dosage forms. The dosage forms comprise as the active components an inhibitor as defined previously.

For preparing pharmaceutical compositions, one uses inert, pharmaceutically acceptable carriers that can be either solid or liquid. Solid form preparations include powders, tablets, dispersible granules, capsules, cachets, and suppositories. A solid carrier can be one or more substances which may also act as dilutents, flavoring agents, solubilizers, lubricants, suspending agents, binders, or tablet disintegrating agents; it can also be an encapsulating material. In powders, the carrier is a finely divided solid which is in admixture with the finely divided active compounds. In the tablet, the active compounds are mixed with carrier having the necessary binding properties in suitable proportions and compacted in the shape and size desired. The powders and tablets preferably contain from 5% or 10% to about 70% of active ingredients. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compounds with encapsulating materials as carrier, providing a capsule in which the active components (with or without other carriers) are surrounded by carrier, which are thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active components in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation may be subdivided into unit doses containing appropriate quantities of inhibitor and other anti-cancer materials individually or as a combination, i.e., in a mixture. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form. Additionally, the unit dosage form may be a dividable form having an inhibitor in one part and other anti-cancer materials in the other part, such as, a dividable capsule, a dividable package, or a two-part ampoule, vial or the like.

The quantity of an inhibitor in unit dosages of preparation may be varied or adjusted from about 0.01 mg/kg to 100.0 mg/kg, preferably 0.03 mg/kg to less than 1.0 mg/kg of inhibitor.

The pharmaceutical compositions preferably are constituted so that they can be administered parenterally or orally. Solutions of the active compounds as free bases and free acids or pharmaceutically acceptable salts can be prepared in water suitable mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of the microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion, and by the use of surfactants. The prevention of the action of microorganisms can be brought about by various antibacterial and antifungal agents, for example, paragens, chlorobutanol, phenol, sorbic acid, thimerosal, and the like. In many cases, it will be preferred to include isotonic agents, for example, sugars or sodium chloride. Prolonged absorption of the injectable compositions of agents delaying absorption, for example, gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients, into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yields a powder of active ingredients plus an additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active materials calculated to produce the desired therapeutic effect in association with the required pharmaceutical carrier. The specification for the novel dosage unit forms of the invention are dictated by and directly dependent on (a) the unique characteristics of the active materials and the particular therapeutic effect to be achieved, and (b) the limitation inherent in the art of compounding such active materials for the treatment of disease in living subjects having a diseased condition in which bodily health is impaired as herein disclosed in detail.

The principal active ingredients are compounded for convenient and effective administration in effective amounts with a suitable pharmaceutically acceptable carrier in dosage unit form as hereinbefore disclosed. A unit parenteral dosage form can, for example, contain the principal active compound, i.e. an inhibitor, in amounts ranging from about 0.5 to about 100 mg, with from about 0.1 to 50 mg being preferred. The daily parenteral doses for mammalian subjects to be treated ranges from 0.01 mg/kg to 10 mg/kg of the inhibitor. The preferred daily dosage range is 0.1 mg/kg to 1.0 mg/kg.

For oral dosages, the daily amount may range from 0.01 mg of active compound/kg of mammalian subject to 100 mg/kg, preferably 0.1 to 10 mg/kg of subject.

The inhibitor described above may form commonly known, pharmaceutically acceptable salts such as alkali metal and other common basic salts or acid addition salts, etc. References to the base substances are therefore intended to include those common salts known to be substantially equivalent to the parent compound and hydrates thereof.

The active compounds described herein are capable of further forming both pharmaceutically acceptable acid addition and/or base salts. All of these forms are within the scope of the present invention.

Pharmaceutically acceptable acid addition salts of the active compounds include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M. et al, "Pharmaceutical Salts", *JOURNAL OF PHARMACEUTICAL SCIENCE*, 66, pp. 1–19 (1977)).

The acid addition salts of said basic compounds are prepared by contacting the free base form with a sufficient amount of the desired acid to produce the salt in the conventional manner. Preferably, an active compound can be converted to an acidic salt by treating with an aqueous solution of the desired acid, such that the resulting pH is less than 4. The solution can be passed through a C18 cartridge to absorb the compound, washed with copious amounts of water, the compound eluted with a polar organic solvent such as, for example, methanol, acetonitrile, and the like, and isolated by concentrating under reduced pressure followed by lyophilization. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M. et al, "Pharmaceutical Salts", *JOURNAL OF PHARMACEUTICAL SCIENCE*, 66, pp. 1–19 (1977)).

The base addition salts of said acidic compounds are prepared by contacting the free acid form with a sufficient amount of the desired base to produce the salt in the conventional manner. Preferably, an active compound can be converted to a base salt by treating with an aqueous solution of the desired base, such that the resulting pH is greater than 9. The solution can be passed through a C18 cartridge to absorb the compound, washed with copious amounts of water, the compound eluted with a polar organic solvent such as, for example, methanol, acetonitrile and the like, and isolated by concentrating under reduced pressure followed by lyophilization. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acids for purposes of the present invention.

Certain of the compounds of the present invention can exist in unsolvated forms as well as solvated forms, including hydrated forms. In general, the solvated forms, including hydrated forms are equivalent to unsolvated forms and are intended to be encompassed within the scope of the present invention.

Certain of the compounds of the present invention possess one or more chiral centers and such center may exist in the R(D) or S(L) configuration. The present invention includes all enantiomeric and epimeric forms as well as the appropriate mixtures thereof.

While the forms of the invention herein constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

Scheme 1. Synthesis of Preferred Group 1.

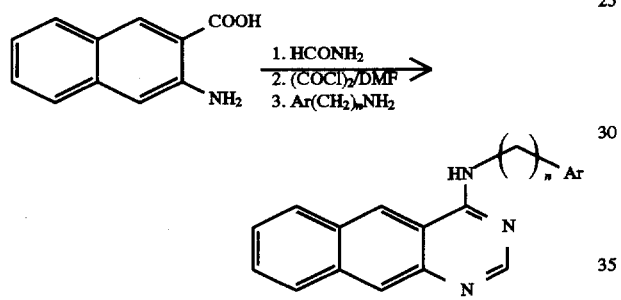

Scheme 2. Synthesis of Preferred Group 4; [3, 2-g] ring fusion.

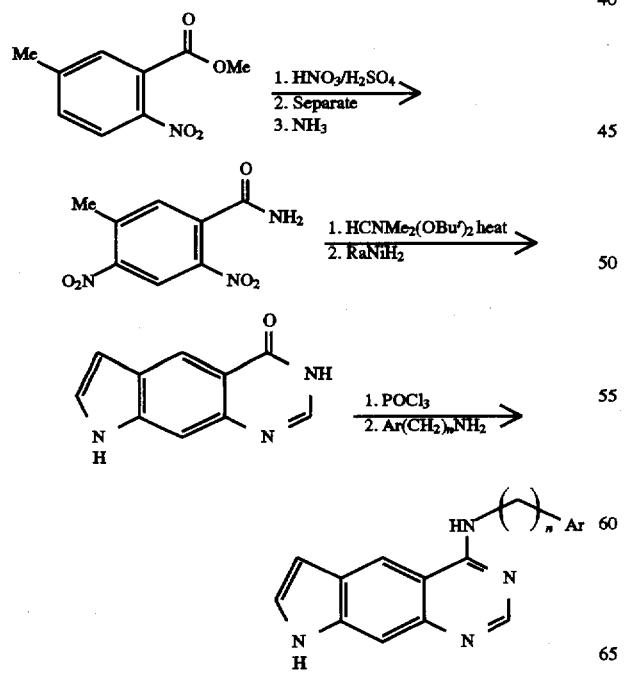

Scheme 3. Synthesis of Preferred Group 5; [4, 5-g] ring fusion.

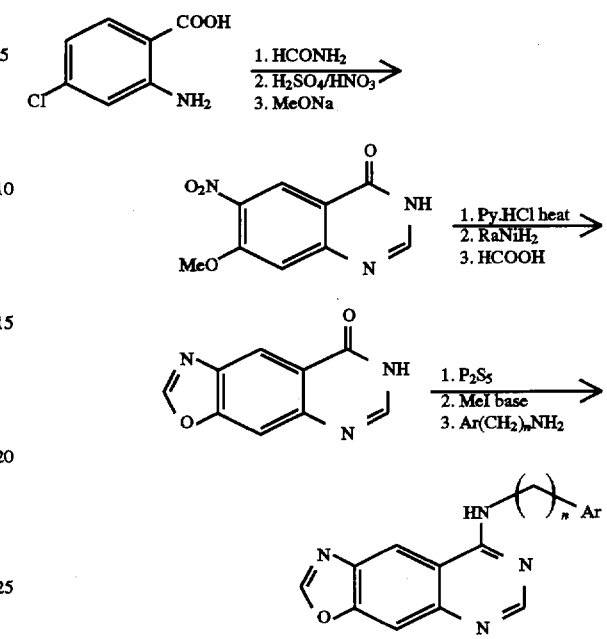

Scheme 4. Synthesis of Preferred Group 5; [5, 4-g] ring fusion.

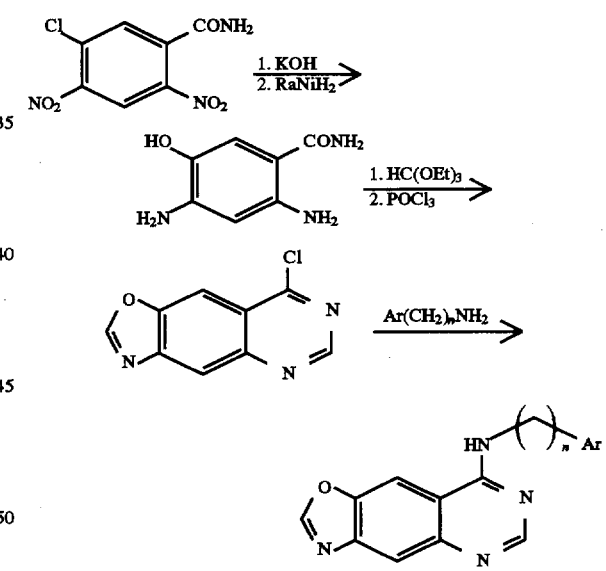

Scheme 5. Synthesis of Preferred Group 6; [4, 5-g] ring fusion.

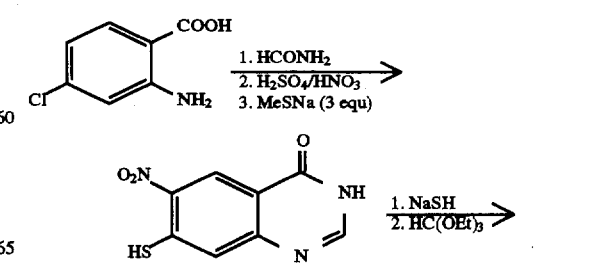

-continued
Scheme 5. Synthesis of Preferred Group 6; [4, 5-g] ring fusion.
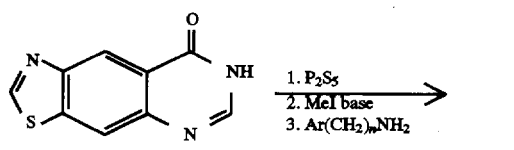
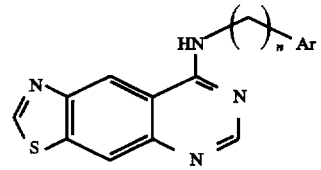
Scheme 6. Synthesis of Preferred Group 6; [5, 4-g] ring fusion.
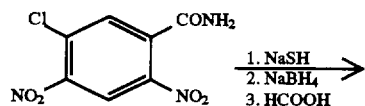
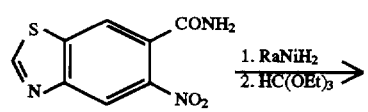
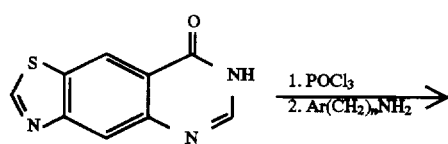
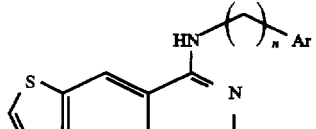
Scheme 7. Synthesis of Preferred Group 7.
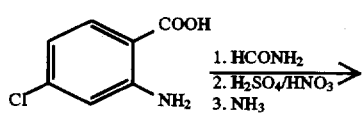
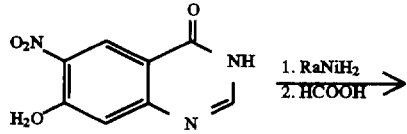
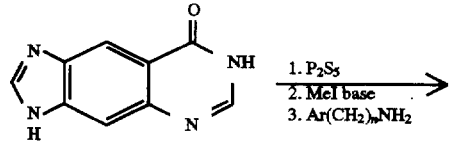
-continued
Scheme 7. Synthesis of Preferred Group 7.
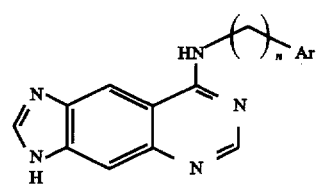
Scheme 8. Synthesis of Preferred Group 10; [4, 3-g] ring fusion
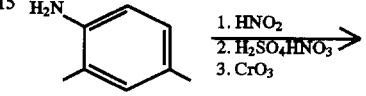
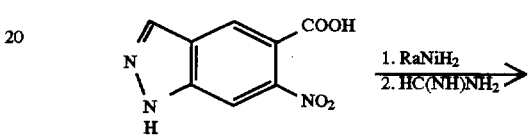
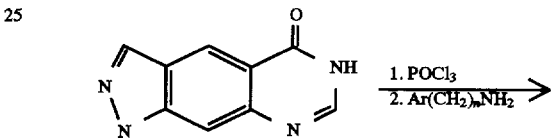
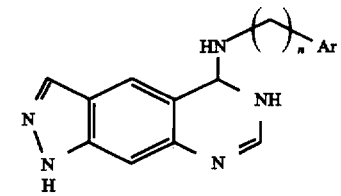
Scheme 9. Synthesis of Preferred Group 10; [3, 4-g] ring fusion
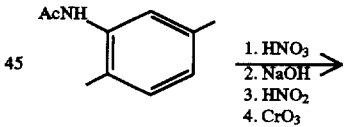
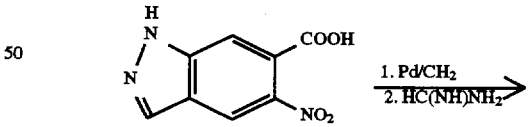
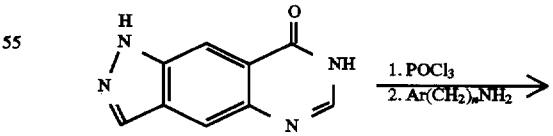
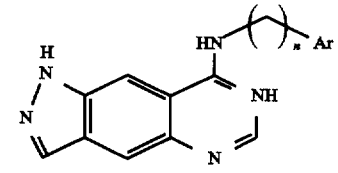

Scheme 10. Synthesis of Preferred Group 11.
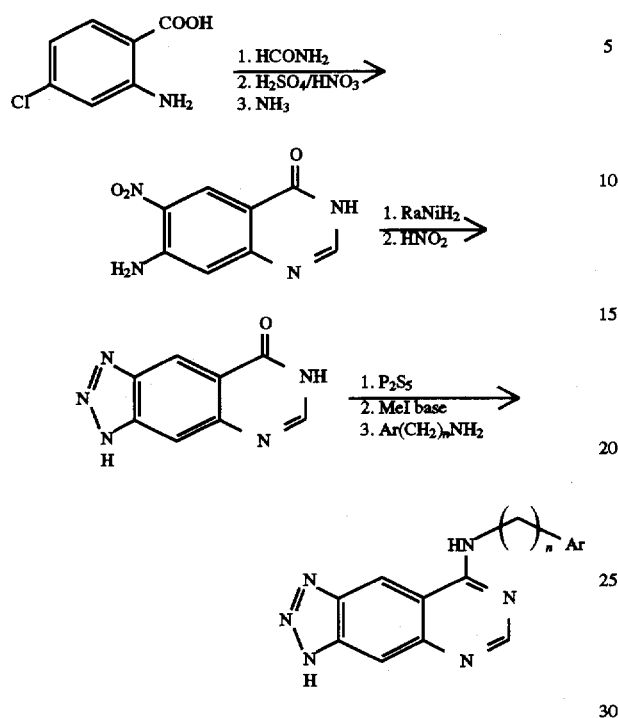
Scheme 11. Synthesis of Preferred Group 13; A & E are Nitrogen.
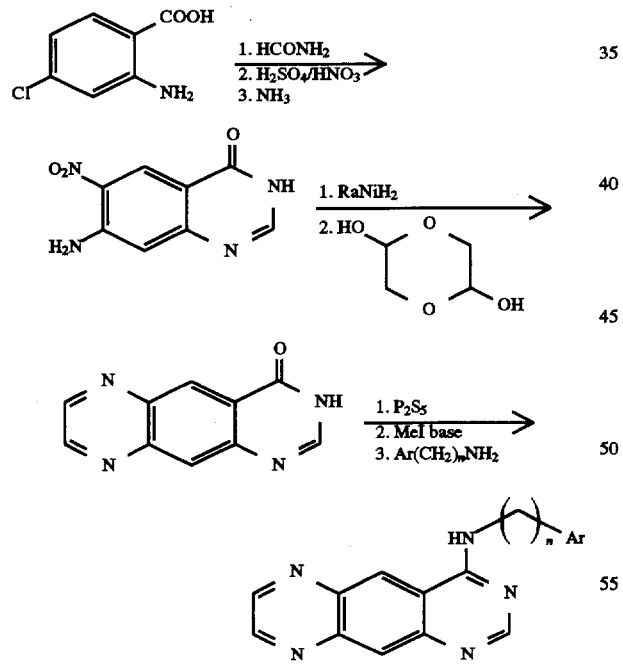
Scheme 12. Synthesis of Preferred Group 13; B & E are Nitrogen.
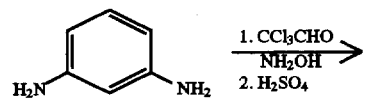
Scheme 12. Synthesis of Preferred Group 13; B & E are Nitrogen.
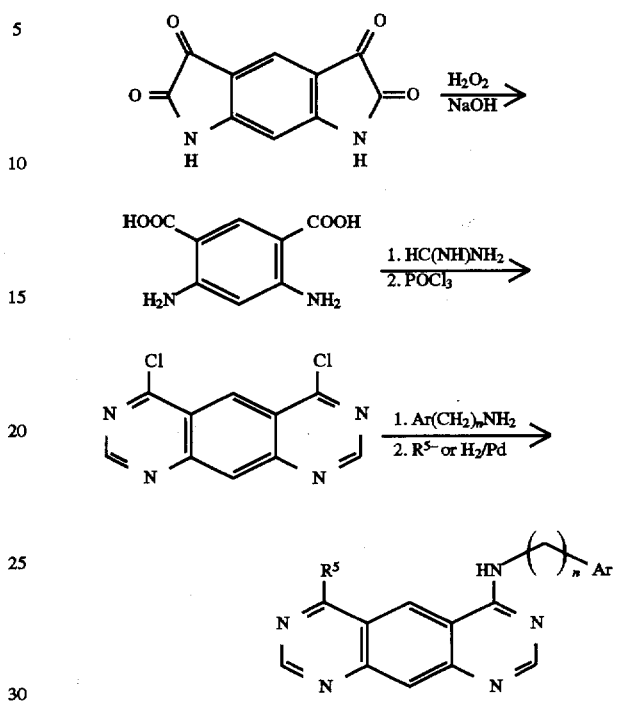
Scheme 13. Synthesis of Preferred Group 33; [4,5-f] ring fusion
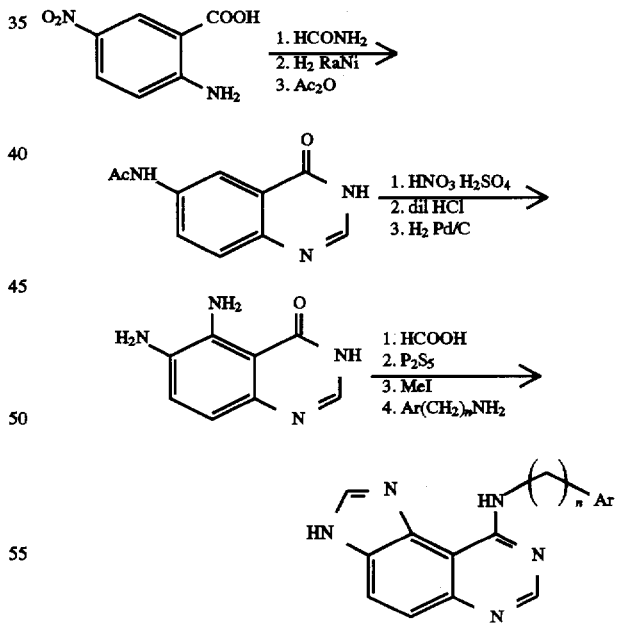
Scheme 14. Synthesis of Preferred Group 33; [4,5-h] ring fusion
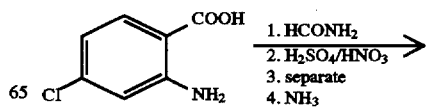

-continued
Scheme 14. Synthesis of Preferred Group 33; [4,5-h] ring fusion
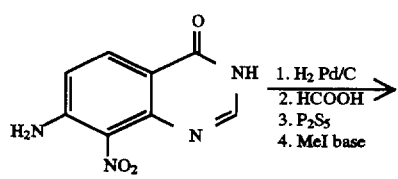
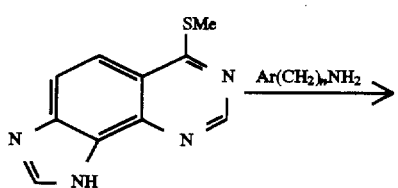
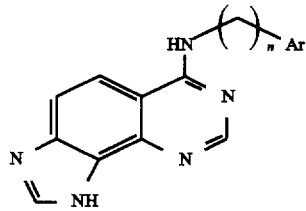
Scheme 15. Synthesis of Preferred Group 39; [3,2-d] ring fusion
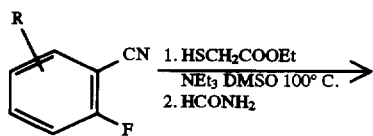
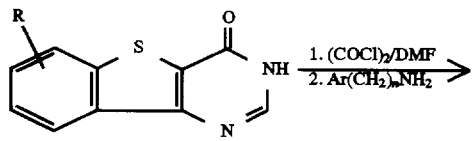
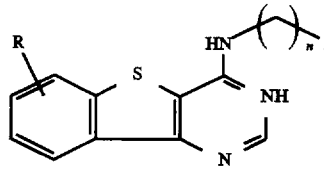
Scheme 16. Synthesis of Preferred Group 39; [3,2-d] ring fusion
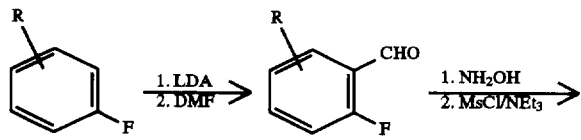
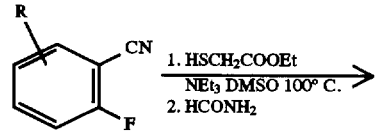
Scheme 16. Synthesis of Preferred Group 39; [3,2-d] ring fusion
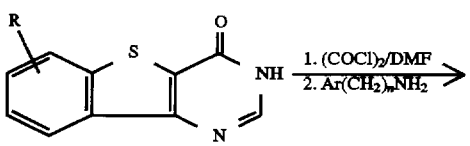
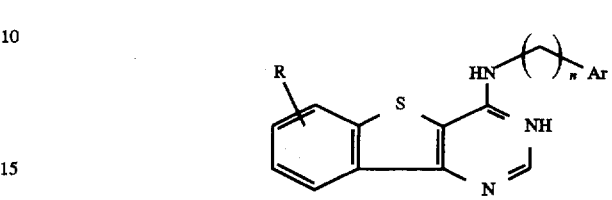
Scheme 17. Synthesis of Preferred Group 39; [2,3-d] ring fusion
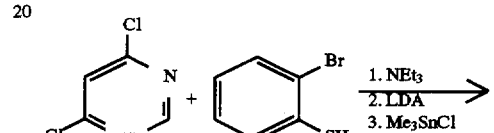
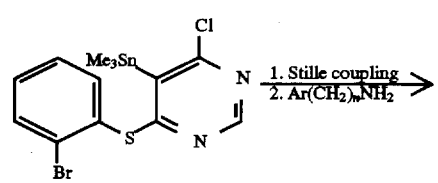
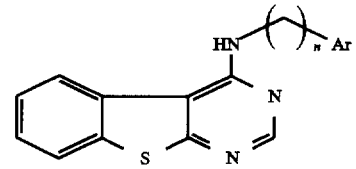
Scheme 18. Synthesis of Preferred Group 41; [3',2':2,3][4,5-d] ring fusion
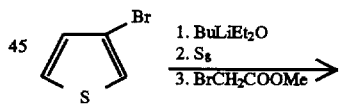
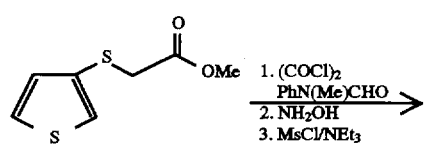
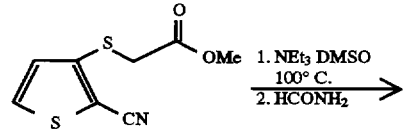
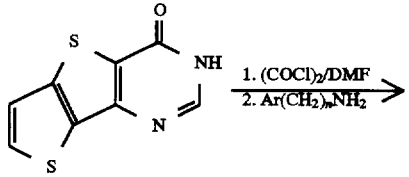

-continued
Scheme 18. Synthesis of Preferred Group 41; [3',2':2,3][4,5-d] ring fusion
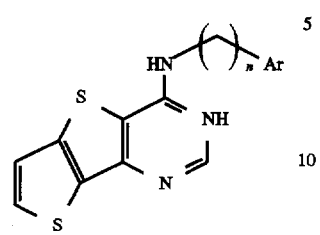
Scheme 19. Synthesis of Preferred Group 41; [2',3':2,3][5,4-d] ring fusion
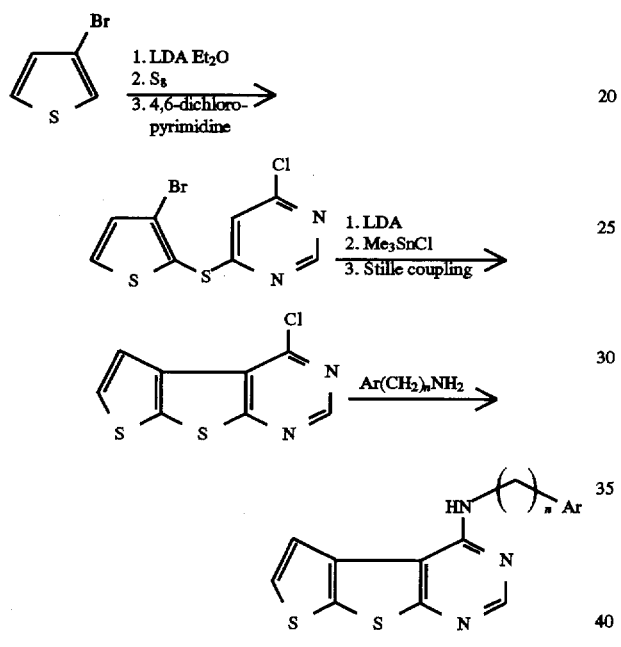
Scheme 20. Synthesis of Preferred Group 44; [4',5':2,3][4,5-d] ring fusion
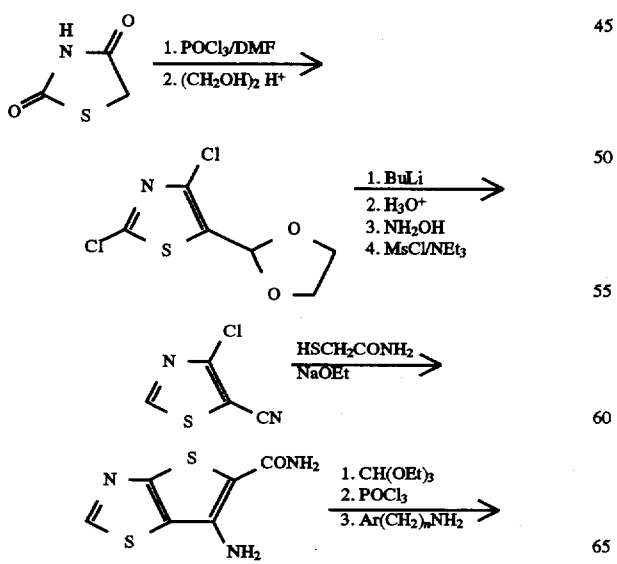
-continued
Scheme 20. Synthesis of Preferred Group 44; [4',5':2,3][4,5-d] ring fusion
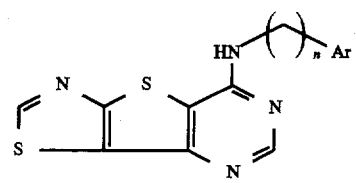
Scheme 21. Synthesis of Preferred Group 45; [4',5':2,3][4,5-d] ring fusion
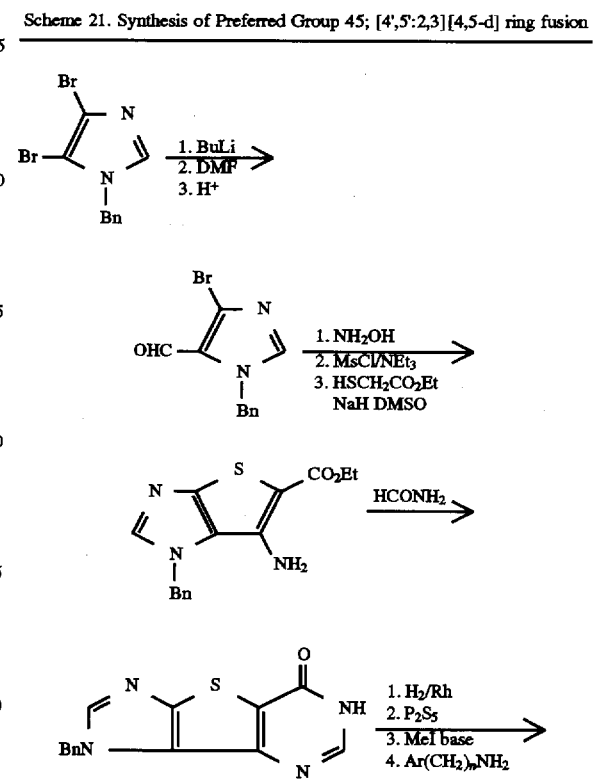
Scheme 22.
Synthesis of Preferred Group 49; [2',3': 2,3][4,5-d]ring fusion
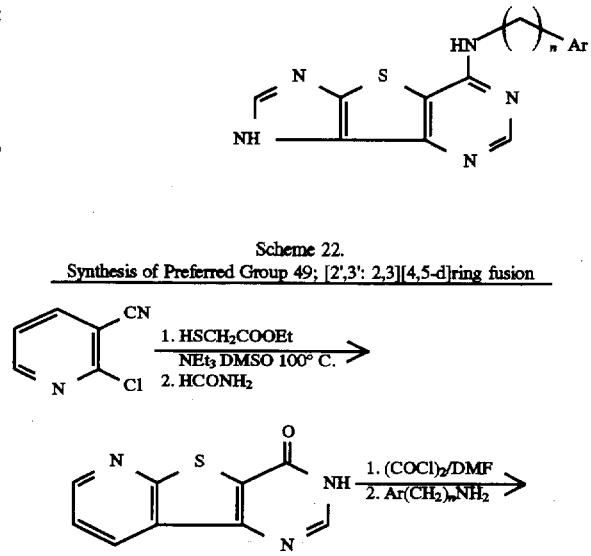

Scheme 22.
Synthesis of Preferred Group 49; [2',3': 2,3][4,5-d]ring fusion

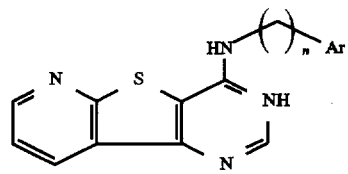

Scheme 23.
Synthesis of Preferred Group 50; [3,2-d]ring fusion

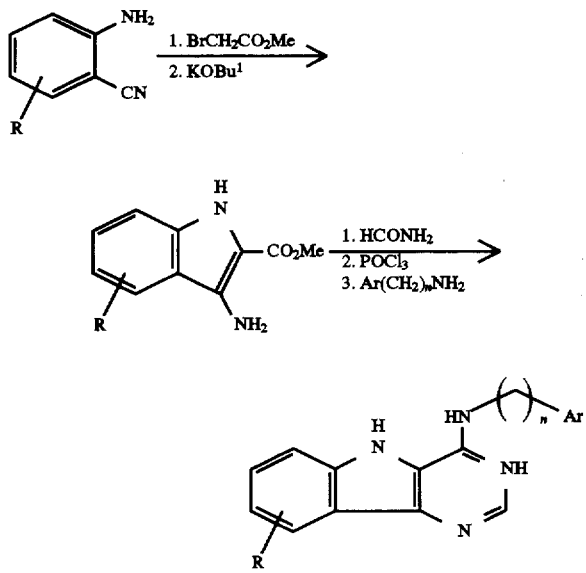

Scheme 24.
Synthesis of Preferred Group 50; [2,3-d]ring fusion

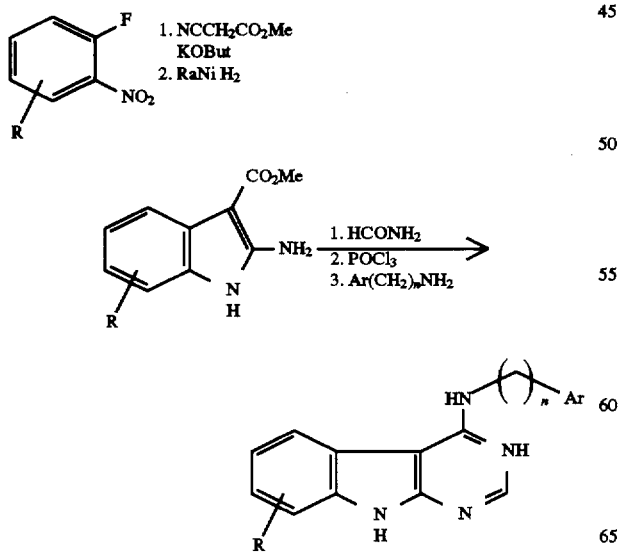

Scheme 25.
Synthesis of Preferred Group 61; [3,2-d]ring fusion

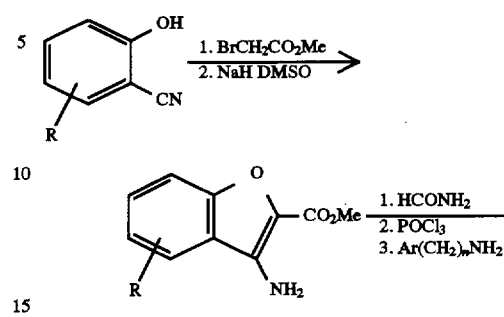

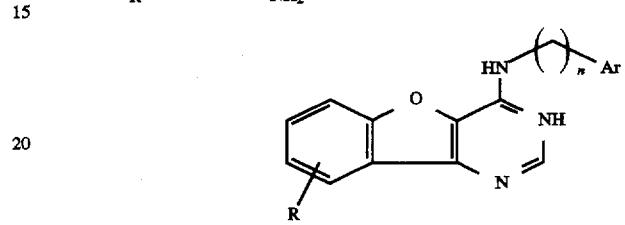

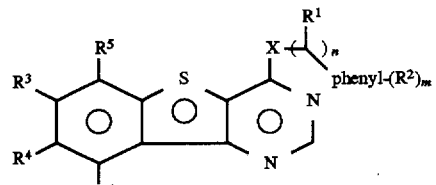

What is claimed is:

1. A compound of formula Ia or Ib

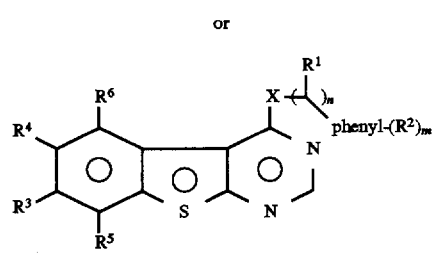

wherein X is NH or $NR^9$ wherein $R^9$ is selected from the group consisting of lower alkyl (1–4 carbon atoms), OH, $NH_2$, lower alkoxy (1–4 carbon atoms) and lower monoalkylamino (1–4 carbon atoms);

$R^1$ is H or lower alkyl;

n is 0, 1 or 2; if n is 2, $R^3$ is independently H or lower alkyl (1–4 carbon atoms) on either linking carbon atom, and both R and S stereocentres on either linker are included;

$R^2$ is selected from the group consisting of lower alkyl (1–4 carbon atoms), cycloalkyl (3–8 carbon atoms), lower alkoxy (1–4 carbon atoms), cycloalkoxy (3–8 carbon atoms), nitro, halo, lower perfluoroalkyl (1–4 carbon atoms), lower acyloxy (1–4 carbon atoms; —O—C(O)—R), amino, lower mono or dialkylamino (1–4 carbon atoms), lower mono or dicycloalkylamino (3–8 carbon atoms), lower acyl (1–4 carbon atoms; —C(O)R), cyano, lower thioalkyl (1–4 carbon atoms), lower sulfinylalkyl (1–4 carbon atoms), lower sulfonylalkyl (1–4 carbon atoms), thiocycloalkyl (3–8 carbon atoms), sulfinylcycloalkyl (3–8 carbon atoms), sulfonylcycloalkyl (3–8 carbon atoms), lower alkoxycarbonyl (1–4 carbon atoms), cycloalkoxycarbonyl (3–8 carbon atoms), lower alkenyl (2–4 carbon atoms), cycloalkenyl (4–8 carbon atoms), lower alkynyl (2–4 carbon atoms), and two $R^2$ taken together form a carbocyclic ring of 5–7 members;

m is 1–3;

$R^3$, $R^4$, $R^5$ and $R^6$ are independently selected from the group consisting of H, lower alkyl (1–4 carbon atoms), cycloalkyl (3–8 carbon atoms), lower alkoxy (1–4 carbon atoms), cycloalkoxy (3–8 carbon atoms), hydroxy, lower acyloxy (1–4 carbon atoms), amino, lower mono or dialkylamino (1–4 carbon atoms), lower mono or dicycloalkylamino (3–8 carbon atoms), carbonato (—OC(O)OR) where R is alkyl of from 1–4 carbon atoms or cycloalkyl of from 3–8 carbon atoms;

ureido or thioureido or N— or O— linked urethane any one of which is optionally substituted by mono or di-lower alkyl (1–4 carbon atoms) or cycloalkyl (3–8 carbon atoms);

lower thioalkyl (1–4 carbon atoms), thiocycloalkyl (3–8 carbon atoms), mercapto, lower alkenyl (2–4 carbon atoms), hydrazino, N'-lower alkylhydrazino (1–4 carbon atoms), lower acylamino (1–4 carbon atoms), hydroxylamino, and lower O-alkylhydroxylamino (1–4 carbon atoms), any lower alkyl group substituent on any of the substituents in $R^3$–$R^6$ which moiety is optionally substituted with one or more groups selected from the group consisting of hydroxy, amino, lower monoalkylamino, lower dialkylamino, N-pyrrolidyl, N-piperidinyl, N-pyridinium, N-morpholino, N-thiomorpholino and N-piperazino groups;

optionally if any of the substituents $R^1$, $R^2$, $R^3$ or $R^4$ have chiral centers, then all stereoisomers thereof both separately and as racemic and/or diastereoisomeric mixtures are included; or a pharmaceutical salt or hydrate thereof.

2. The compound of claim 1 wherein the compound is selected from the group consisting of:

4-(3-Bromoanilino)benzothieno[3,2-d]pyrimidine; 4-(3-bromoanilino)-8-nitrobenzothieno[3,2-d]pyrimidine; 8-amino-4-(3-bromoanilino)benzothieno[3,2-d]pyrimidine; and 4-(3-bromoanilino)-8-methoxybenzothieno[3,2-d]pyrimidine.

* * * * *

UNITED STATES PATENT AND TRADEMARK OFFICE
CERTIFICATE OF CORRECTION

PATENT NO. : 5,679,683
DATED : October 21, 1997
INVENTOR(S) : Bridges et al

It is certified that error appears in the above-identified patent and that said Letters Patent is hereby corrected as shown below:

Column 60, line 51, $R^3$ should be $R^1$

Signed and Sealed this

Fifth Day of January, 1999

Attest:

*Attesting Officer*  *Acting Commissioner of Patents and Trademarks*